US009631028B2

(12) United States Patent
Fass et al.

(10) Patent No.: US 9,631,028 B2
(45) Date of Patent: Apr. 25, 2017

(54) COMPOSITIONS FOR INHIBITION OF QUIESCIN SULFHYDRYL OXIDASE (QSOX1) AND USES OF SAME

(71) Applicant: Yeda Research and Development Co. Ltd., Rehovot (IL)

(72) Inventors: Deborah Fass, Rehovot (IL); Iris Grossman, Rehovot (IL); Tal Ilani, Rehovot (IL); Assaf Alon, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 256 days.

(21) Appl. No.: 14/383,571

(22) PCT Filed: Mar. 7, 2013

(86) PCT No.: PCT/IL2013/050209
§ 371 (c)(1),
(2) Date: Sep. 8, 2014

(87) PCT Pub. No.: WO2013/132495
PCT Pub. Date: Sep. 12, 2013

(65) Prior Publication Data
US 2015/0110786 A1 Apr. 23, 2015

Related U.S. Application Data

(60) Provisional application No. 61/665,365, filed on Jun. 28, 2012, provisional application No. 61/607,696, filed on Mar. 7, 2012.

(51) Int. Cl.
*C07K 16/00* (2006.01)
*C07K 16/40* (2006.01)
*A61K 39/00* (2006.01)

(52) U.S. Cl.
CPC ........ *C07K 16/40* (2013.01); *A61K 2039/505* (2013.01); *C07K 2299/00* (2013.01); *C07K 2317/33* (2013.01); *C07K 2317/55* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| CN | 101503679 | 8/2009 |
|---|---|---|
| WO | WO 02/06315 | 1/2002 |
| WO | WO 2010/071787 | 6/2010 |
| WO | WO 2010/077921 | 7/2010 |
| WO | WO 2012/040095 | 3/2012 |
| WO | WO2012040095 | * 3/2012 |
| WO | WO 2013/132495 | 9/2013 |

OTHER PUBLICATIONS

International Preliminary Report on Patentability Dated Sep. 18, 2014 From the International Bureau of WIPO Re. Application No. PCT/IL2013/050209.
International Search Report and the Written Opinion Dated Jun. 5, 2013 From the International Searching Authority Re. Application No. PCT/IL2013/050209.
Amiot et al. "Expression of the Secreted FAD-Dependent Sulfydryl Oxidase (QSOX) in the Guinea Pig Central Nervous System", Molecular Brain Research, 125: 13-21, 2004.
Antwi et al. "Analysis of the Plasma Peptidome From Pancreas Cancer Patients Connects a Peptide in Plasma to Overexpression of the Parent Protein in Tumors", Journal of Proteome Research, 8: 4722-4731, 2009.
Coppock et al. "Preferential Gene Expression in Quiescent Human Lung Fibroblasts", Cell Growth & Differentiation, 4: 483-493, Jun. 1993.
Coppock et al. "Regulation of the Quiescence-Induced Genes: Quiescin Q6, Decorin, and Ribosomal Protein S29", Biochemical and Biophysical Research Communications, 269: 604-610, 2000.
Janolino et al. "Isolation and Characterization of Sulfhydryl Oxidase From Bovine Milk", The Journal of Biological Chemistry, 250(7): 2532-2538, Apr. 10, 1975.
Katchman et al. "Quiescin Sulfhydryl Oxidase 1 Promotes Invasion of Pancreatic Tumor Cells Mediated by Matrix Metalloproteinases", Molecular Cancer Research, XP002697583, 9(12): 1621-1631, Oct. 11, 2011. p. 1626, Para 'Role of QSOX1 in Tumour Cell Invasion'.
Lake et al. (Geltosky) "QSOX1 as an Anti-Neoplastic Drug Target. AzTE Case #M11-003", AzTE Arizona Technology Enterprises, Arizona State University, XP055011559, 1 P., Aug. 30, 2011.
Musard et al. "Identification and Expression of a New Sulfhydryl Oxidase SOx-3 During the Cell Cycle and the Estrus Cycle in Uterine Cells", Biochemical and Biophysical Research Communications, 287: 83-91, 2001.
Ouyang et al. "Loss-of-Function of Nkx3.1 Promotes Increased Oxidative Damage in Prostate Carcinogenesis", Cancer Research, 65: 6773-6779, Aug. 1, 2005.
Portes et al. "Tissue Distribution of Quiescin Q6/Sulfhydryl Oxidase (QSOX) in Developing Mouse", Journal of Molecular Histology, 39: 217-225, 2008.
Song et al. "Loss of Nkx3.1 Leads to the Activation of Discrete Downstream Target Genes During Prostate Tumorigenesis", Oncogene, 28: 3307-3319, Jul. 13, 2009.
Tury et al. "Cell-Specific Localization of the Sulphydryl Oxidase QSOX in Rat Peripheral Tissues", Cell and Tissue Research, 323: 91-103, 2006.
Communication Pursuant to Article 94(3) EPC Dated Aug. 29, 2016 From the European Patent Office Re. Application No. 13716846.4.
Office Action and Search Report Dated Mar. 4, 2016 From the State Intellectual Property Office of the People's Republic of China Re. Application No. 201380024279.0 and Its Translation Into English.
Office Action Dated Apr. 17, 2016 From the Israel Patent Office Re. Application No. 234483.
Communication Pursuant to Article 94(3) EPC Dated Oct. 16, 2015 From the European Patent Office Re. Application No. 13716846.4.

\* cited by examiner

*Primary Examiner* — Lei Yao

(57) ABSTRACT

A method of inhibiting or preventing laminin assembly in a basement membrane is disclosed. The method comprising contacting a tissue with an agent which inhibits QSOX1 activity or expression, thereby inhibiting or preventing laminin assembly in the basement membrane.

3 Claims, 38 Drawing Sheets
(25 of 38 Drawing Sheet(s) Filed in Color)

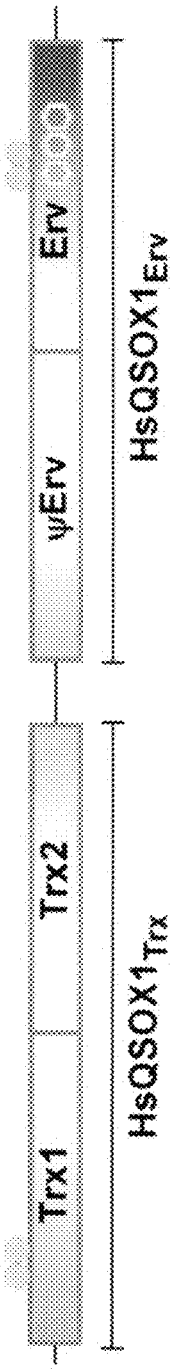
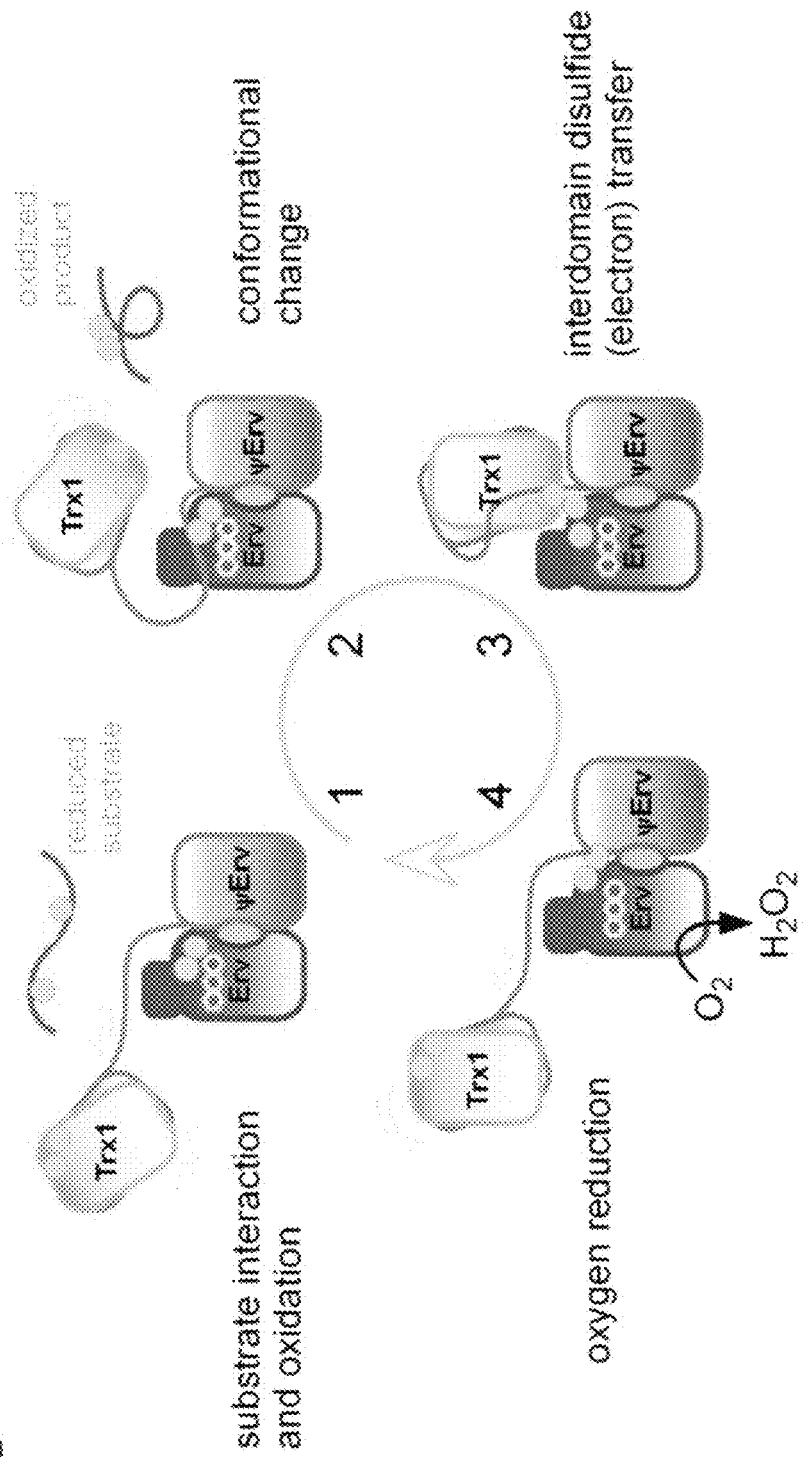
FIG. 1A
FIG. 1B

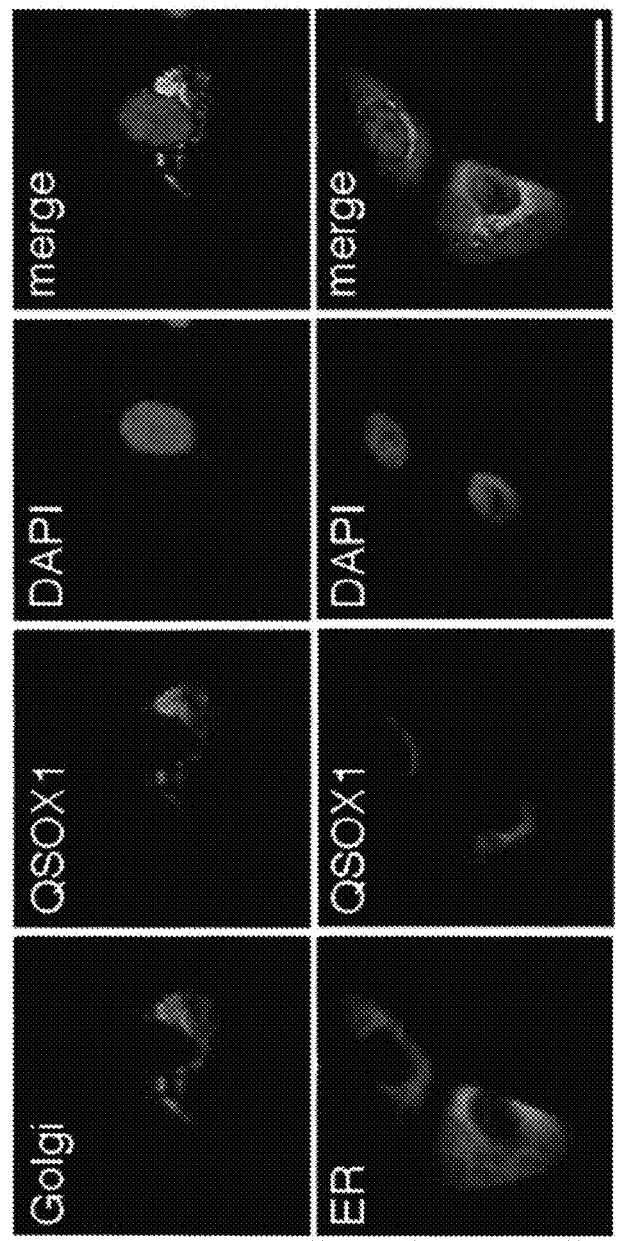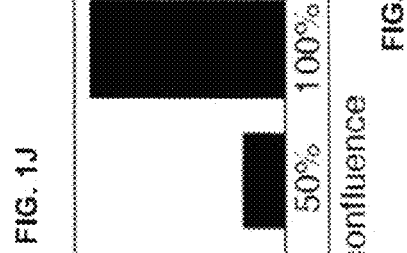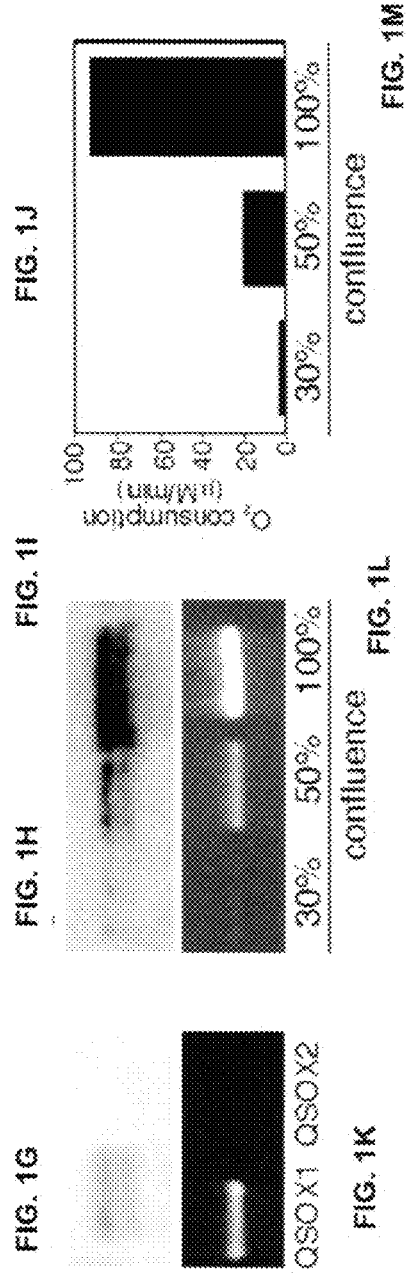

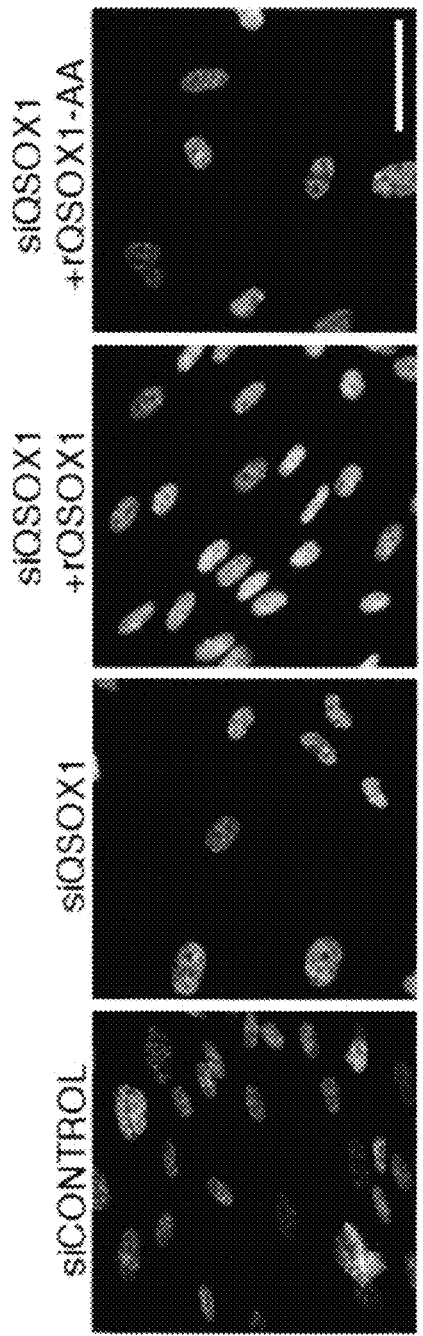
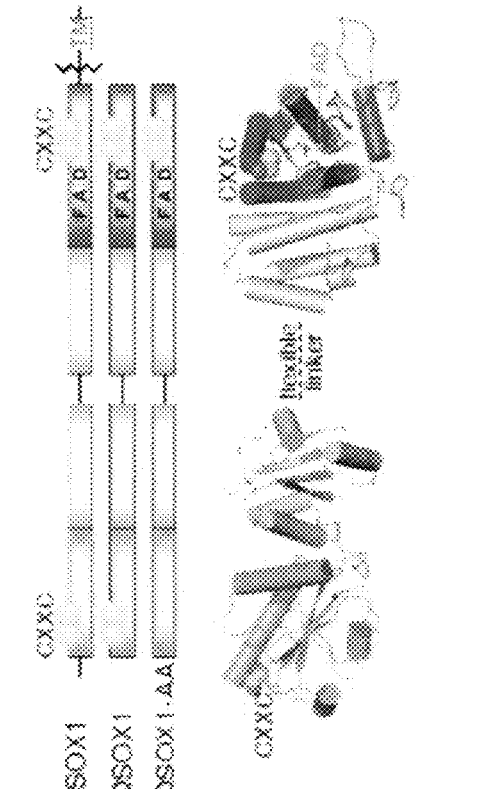
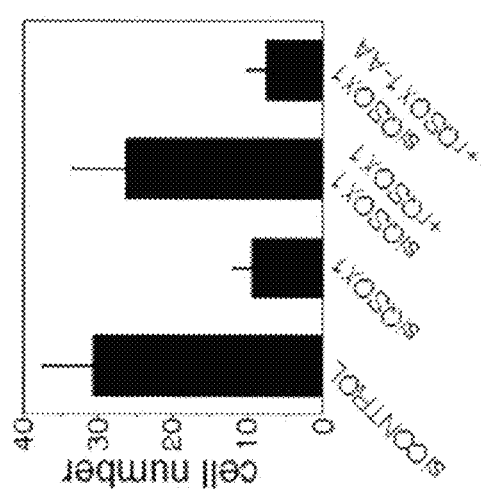

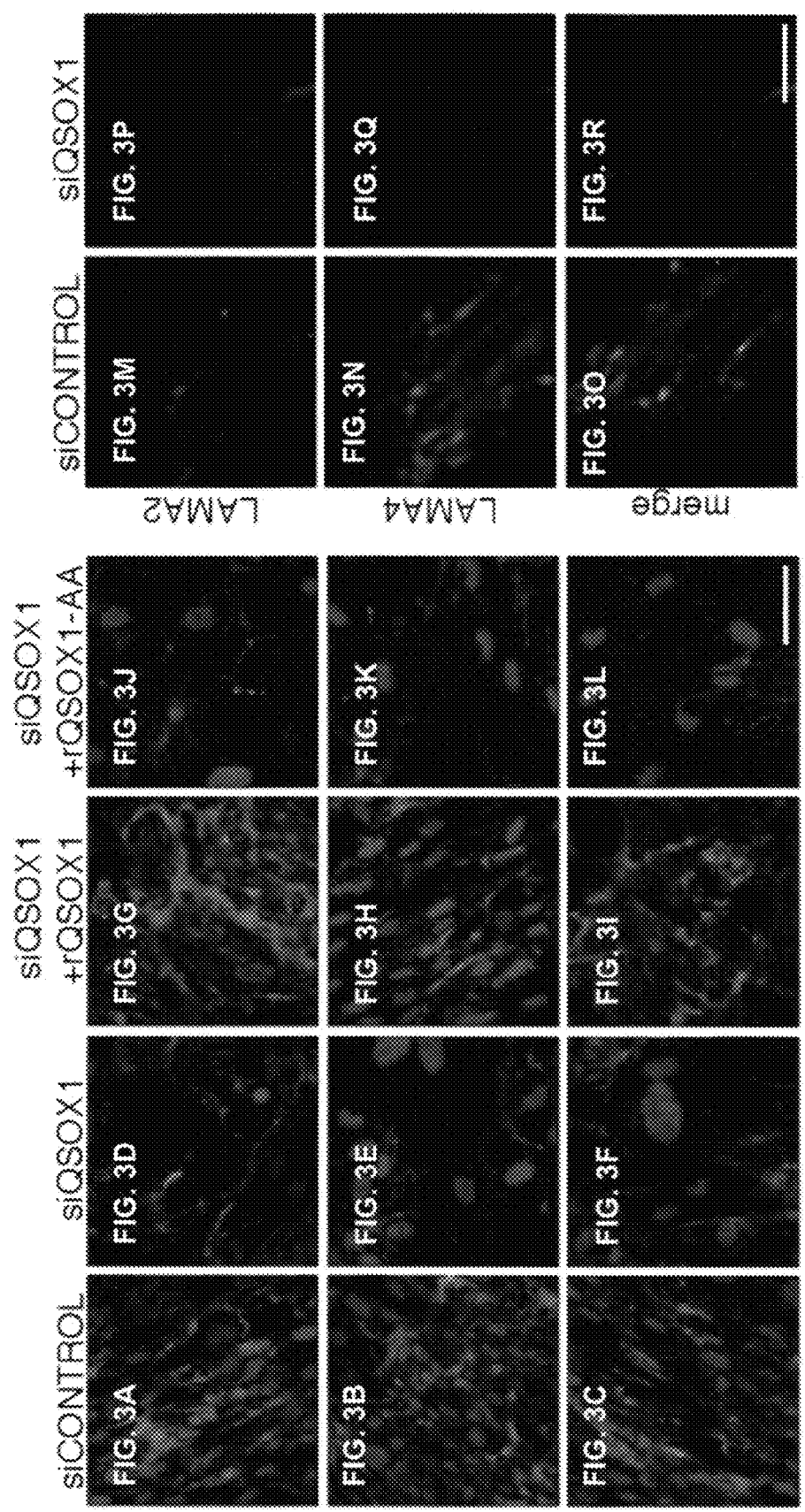

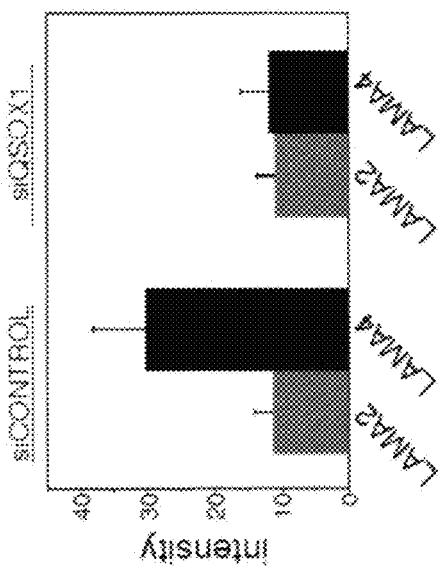
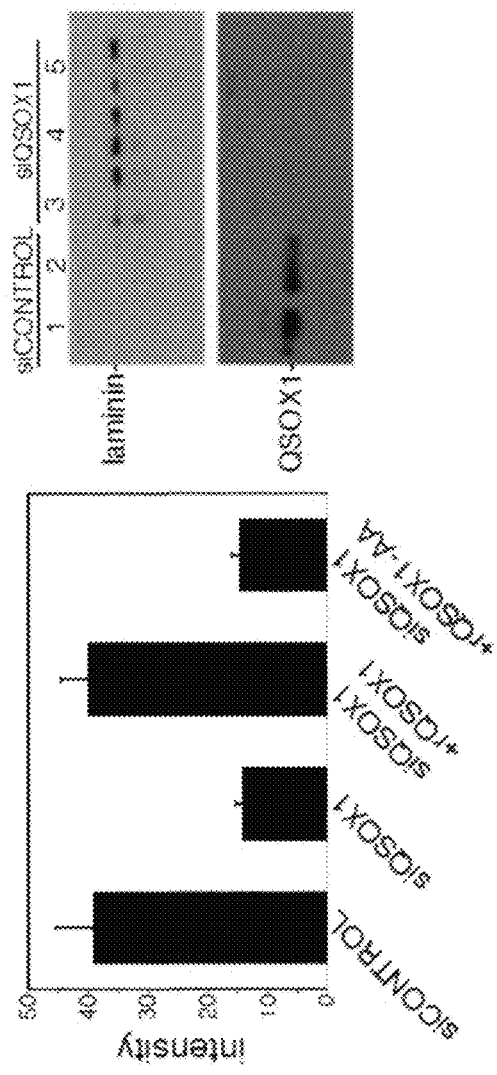
FIG. 4A
FIG. 4B
FIG. 4C

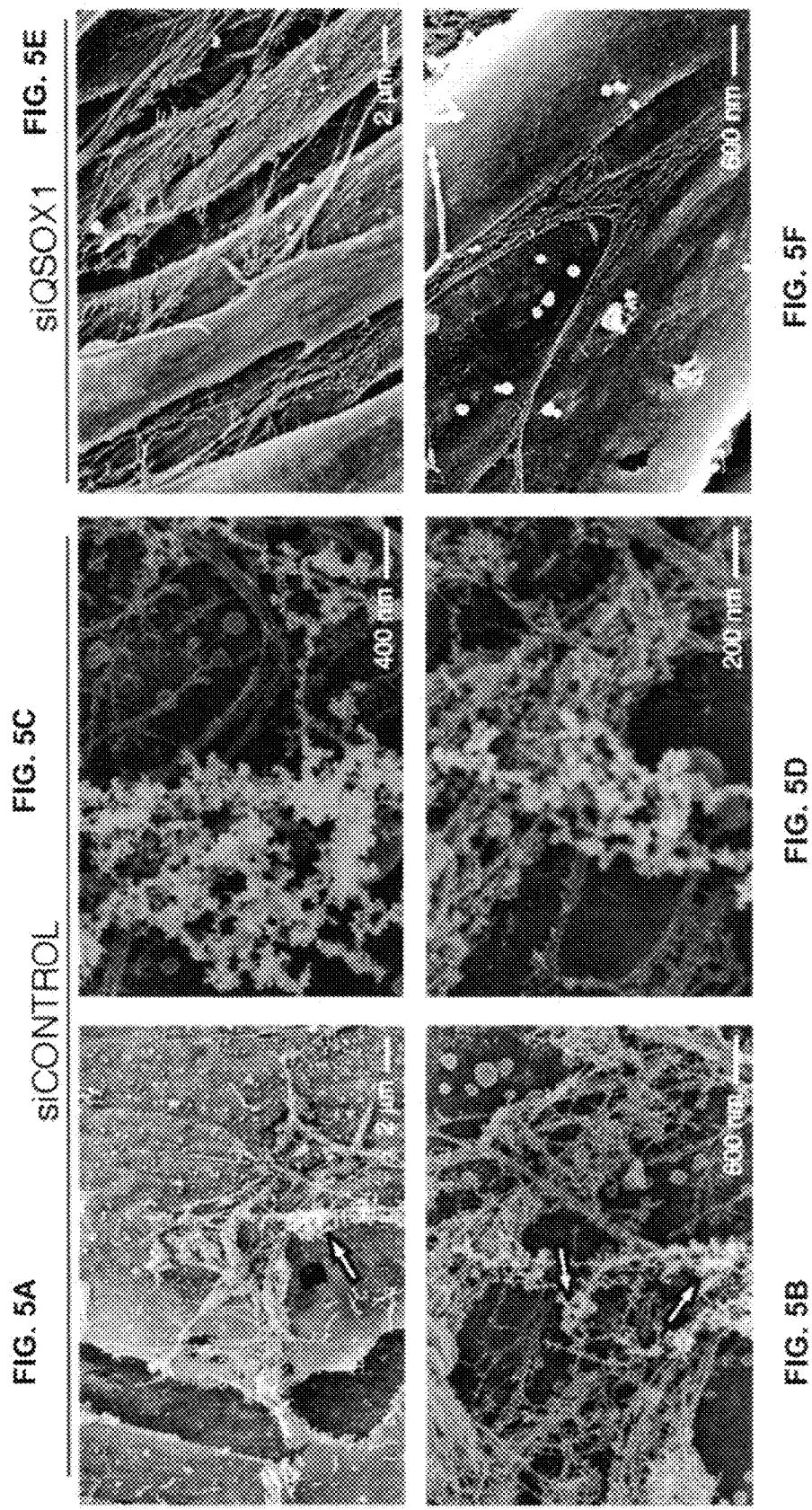

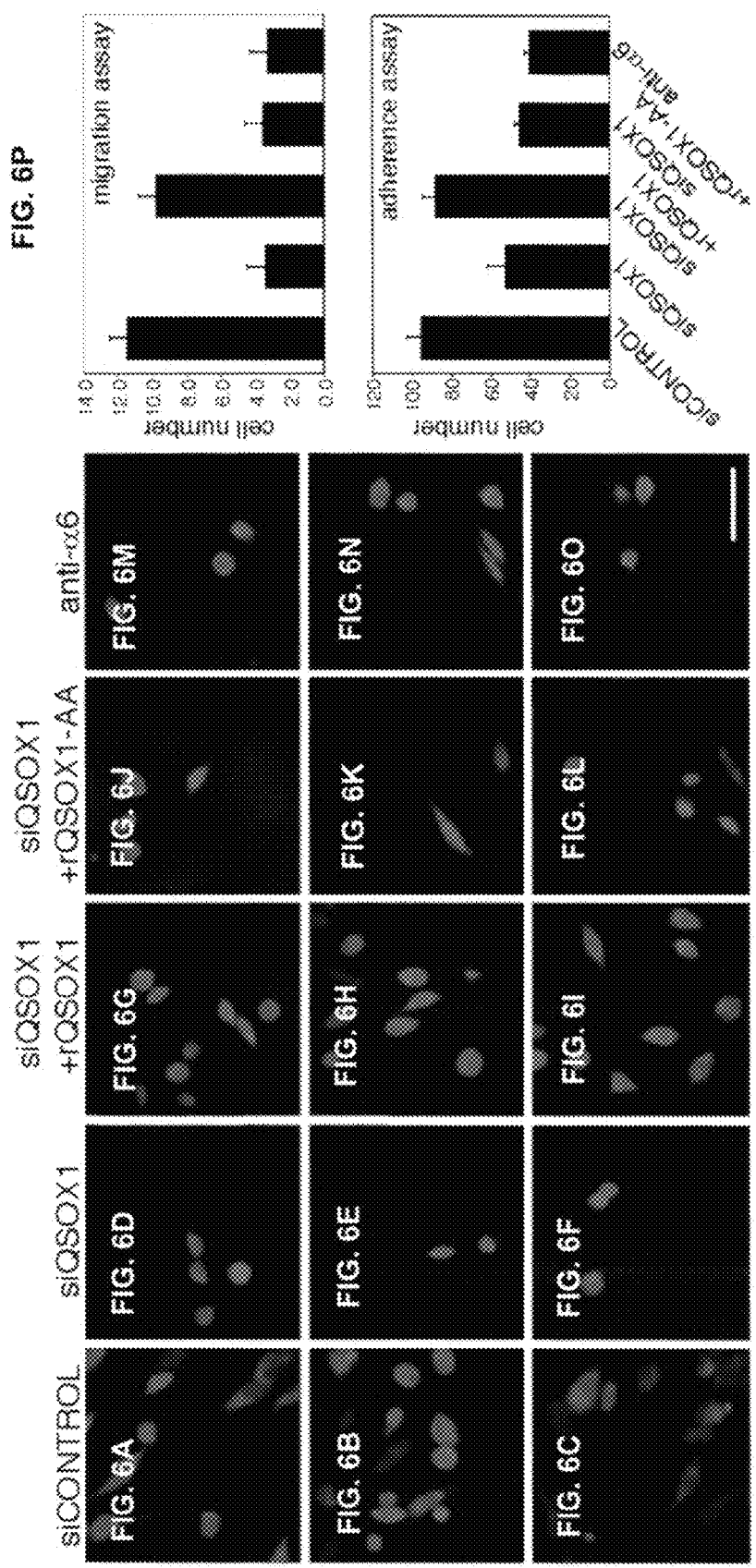

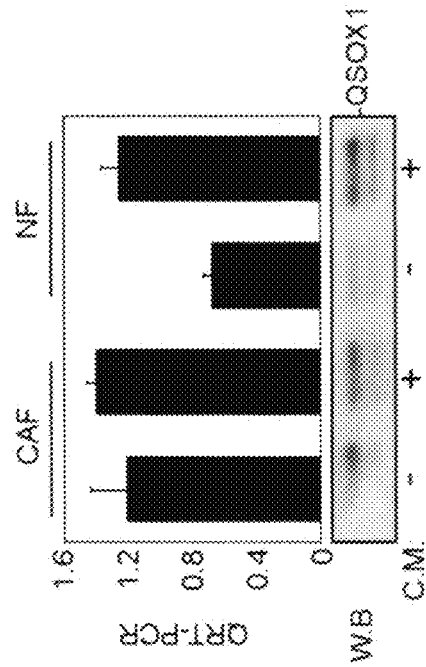
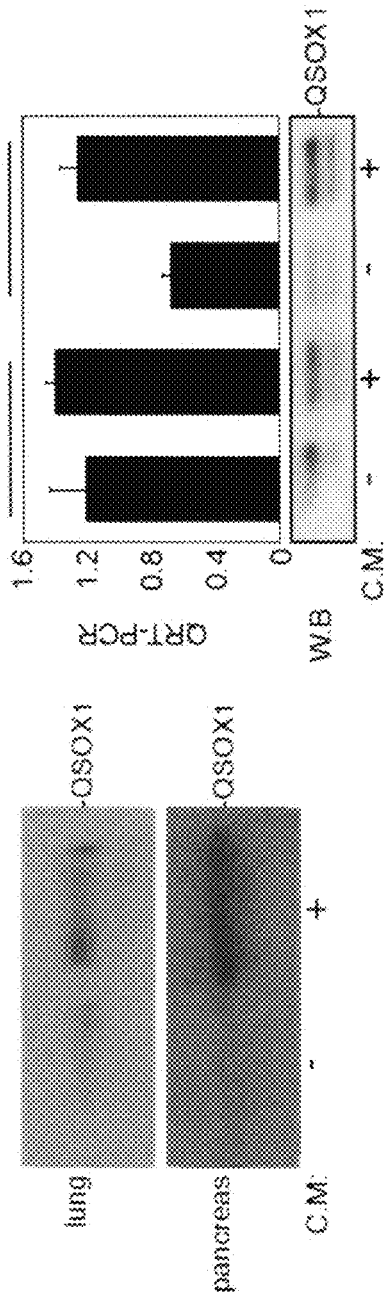
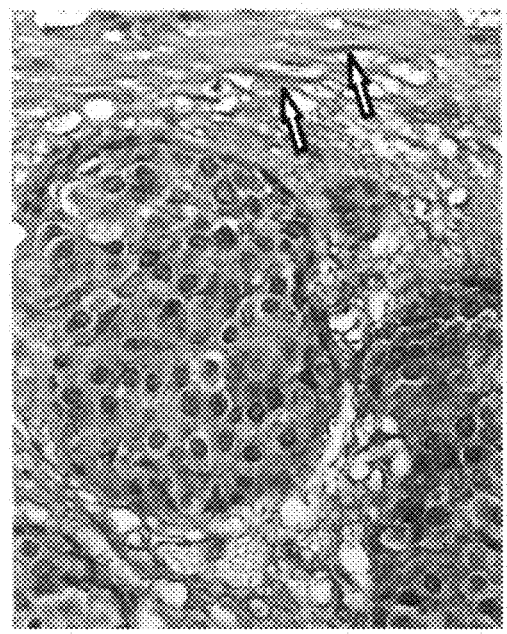
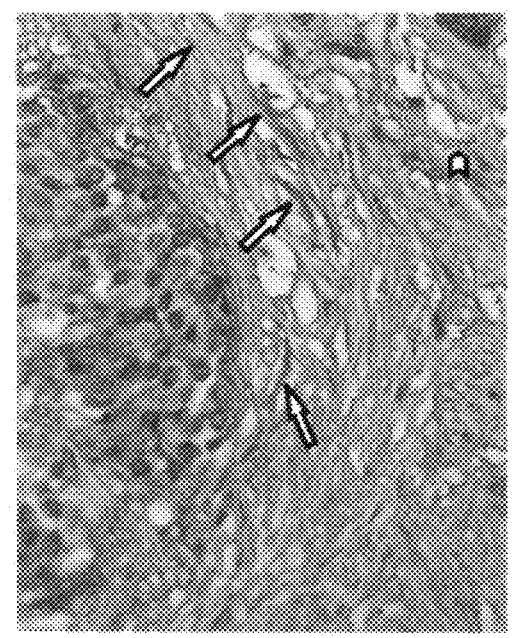

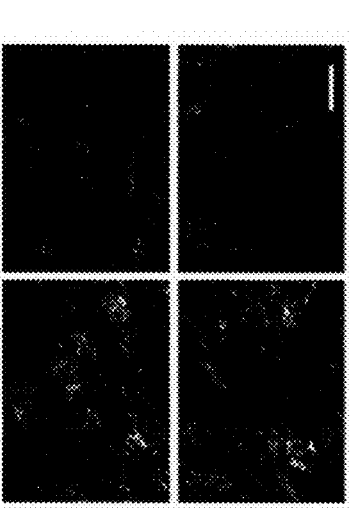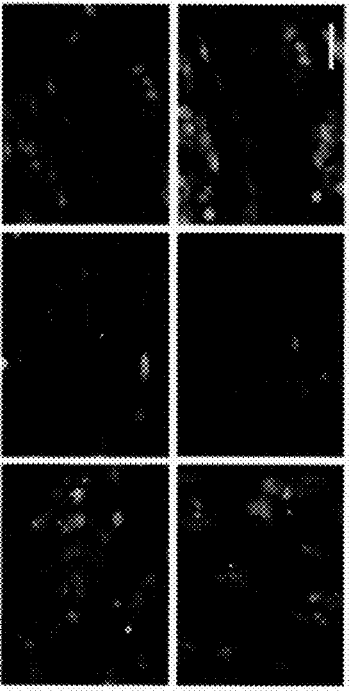

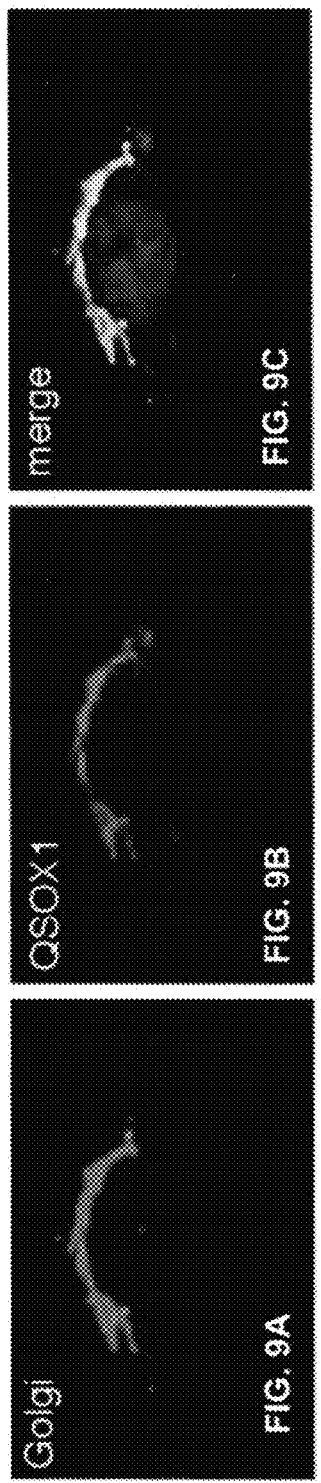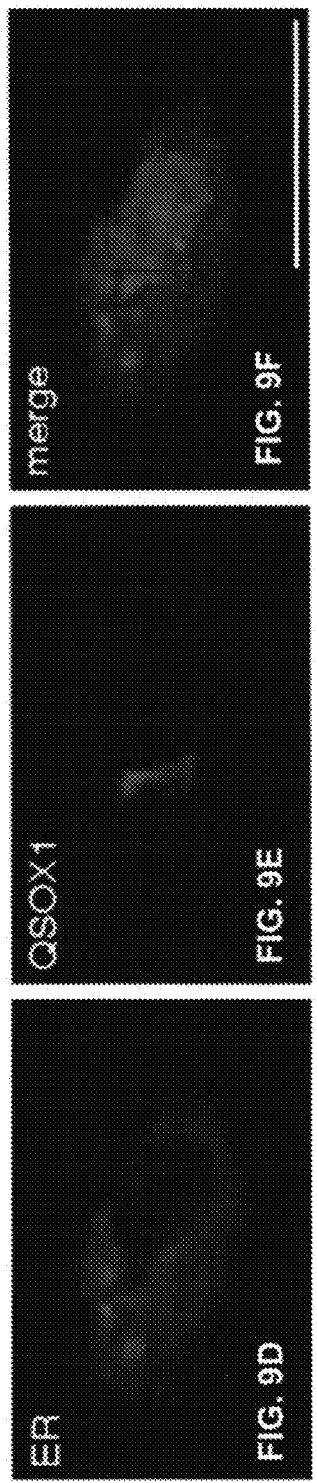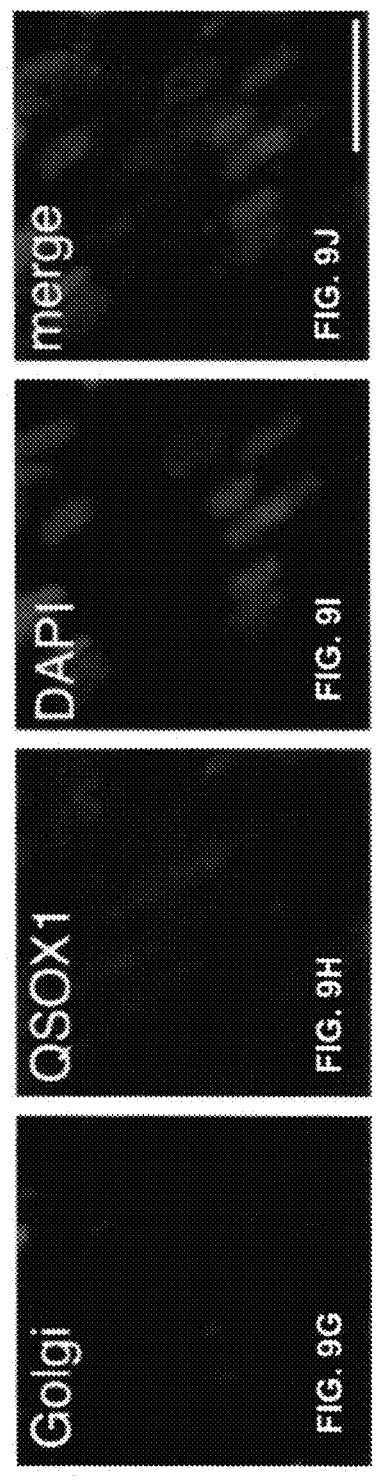

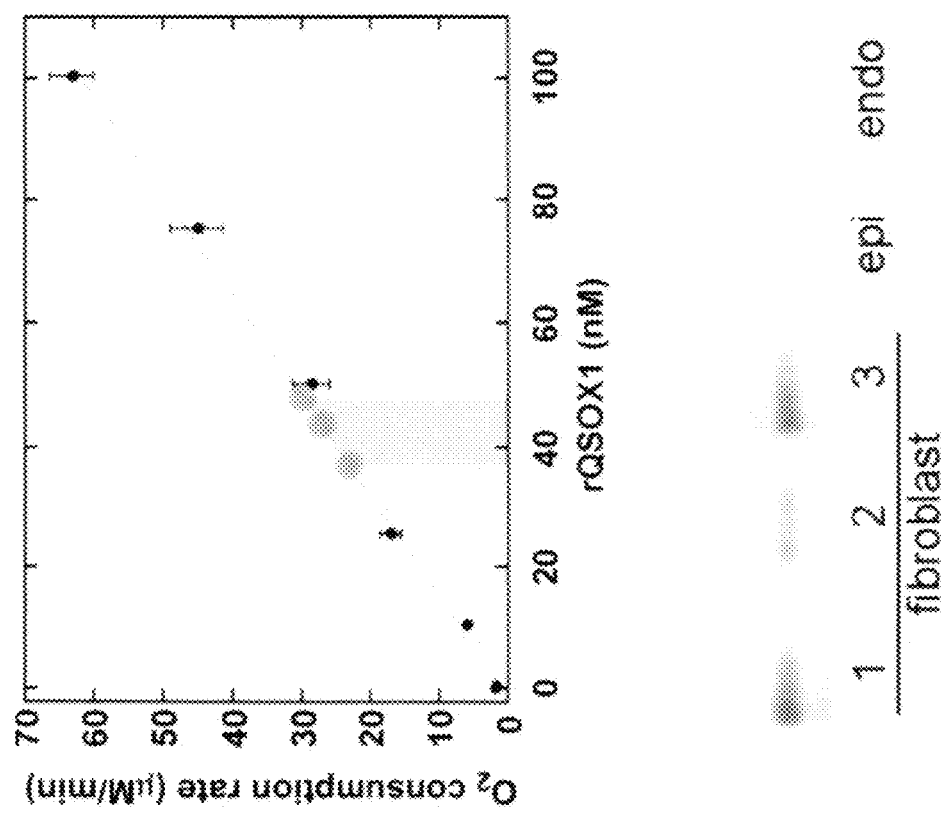

FIG. 10A

QSOX1 lower band trypsin cleavage

```
  1  MRRCNSGSGPPPSLLLLLWLLAVPGANAAPRSALY............LQQYY
 51  .GAVLGSR......................ALAEDVK...........LD
101  ..............................FFK................
151  ......................GVAVR..................MGSVSRV.
201  ..............................TREAAQTTVAPTTANKIAPTVWKLADRSKI.
251  ..........................VAL..YFFPGRPLVQNF
301  ..............................
351  LHSVNEWLKRQKR.....................................
401  RGFPCSLWVLFHFLTVQAARQNVDHSQEAAK...................
451  ...........................................VNARL.................
501  .................................................
551  .R.................................NSTLDFGKPEMMKSPT.T.PHVPAEG-PELI(604)
601  PEASRPPKLHPGLRAAPGQEPPEHMAELQRNEQEQPLGQWHLSKRDTGAA
651  LLAESRAERNRLWGPLEVRAVGRSSKQLVDIPEGQLEARAGRGRGQWLQV
701  LGGGFSYLDISLCVGLYSLSFMGLLAMYTYFQAKIRALKGHAGHPAA(747)
```

SEQ ID NO: 35

FIG. 10B

QSOX1 lower band chymotrypsin cleavage

```
  1  MRRCNSGSGPPPSLLLLLWLLAVPGANAAPRSALY............LQQYY
 51  .........AVEFFASW.................ALA.........RERL
101  ...............................................LLG
151  IDALESHHDTWPPACPPLEPARLEEIDGFF..............LLFRNGSVSRVP
201  REVALD.........................................
251  VLMESRSFY.............VALKKFVAVLAKIYFPGRPL.V.
301  .................................................
351  LKRQKRNKIPY......................................
401  ....VLFHFLTVQAARQNVDHSQEAAKAKEVLPAIRGYVHY......
451  EQMAAASMHRVGSPMAAVLWLWSSHNRVNARL.................
501  .................................................
551  .................ELESR..STLDFGKPEMMKSPT.T.PHVPAEG-PELI(604)
601  PEASRPPKLHPGLRAAPGQEPPEHMAELQRNEQEQPLGQWHLSKRDTGAA
651  LLAESRAERNRLWGPLEVRRVGRSSKQLVDIPEGQLEARAGRGRGQWLQV
701  LGGGFSYLDISLCVGLYSLSFMGLLAMYTYFQAKIRALKGHAGHPAA(747)
```

SEQ ID NO: 36

FIG. 10C

QSOX1 upper band trypsin cleavage

```
  1  MRRCNSGSGPPPSLLLLLWLLAVPGANAAPR........ALAEDVR............L
 51  ........................TAP....WRALTLALD
101  ...........CDENIPGEPTVRFFK........AV.PVA.DVQTLERLL
151  IDALESHHDTWPPACPPLEPAKL.........META.......
201  ......GVAVR..................L
251  .........QRLSGLTREAAQTTVAPTTANKIAPTVWKLADRSK..
301  ............................LVALK.VAVLAKYFFGRPLVQNF
351  LHSVNEWLKRQKR.............
401  GFPCSLMVLFHFLTVQAARQNVDHSQEAAK.........
451  .........VNARLA.........
501  ..........................
551  ..................NSTLDPGKPEMMKSPTNTTPHVPAEG--PELI (604)
601  PEASRPPKLHPGLRA.........NEQBQPLGQWHLSKR.......
651  ...AEKNRL.PLE.RVGRSSKQLVDIPEGQLEARAGRGRGQWLQV
701  LGGGFSYLDISLCVGLYSLSPMGLLAMYTTFQAKIRALKGHAGHPAA (747)
```

SEQ ID NO: 37

FIG. 10D

QSOX1 upper band chymotrypsin cleavage

```
  1  MRRCNSGSGPPPSLLLLLWLLAVPGANAAPRSALY.........D
 51  ....AVEFFASW.......TAP....WRALTLALD
101  ...........AV.PVA.DVQTLRERL
151  IDALESHHDTWPPACPPLEPAKLEEIDGF.........KAFT.......
201  ......CLLFRMGSVSRVP
251  VLMESSRSFY.............
301  TREAAQTTVAPTTANKIAPTVWKLADRSKIY
351  ..................VALKKFVAVLAKYFFGRPL.....
401  .........LKRQKRMKIPY..............AKKVRW
451  EQMAAASMHRVGSPNAAVLWLW..............
501  ..........................
551  ................ELESRMSTLDPGKPEMMKSPTNTTPHVPAEG--PELI (604)
601  PEASRPPKLHPGLRA.........HLSKRDTGAA
651  L..........EVRRVGRSSKQLVDIPEGQLEARAGRGRGQWLQV
701  LGGGFSYLDISLCVGLYSLSPMGLLAMYTTFQAKIRALKGHAGHPAA (747)
```

SEQ ID NO: 38

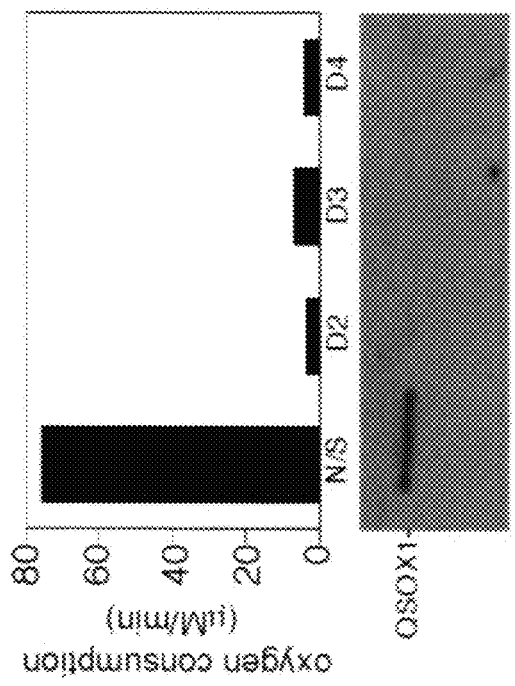
FIG. 11A
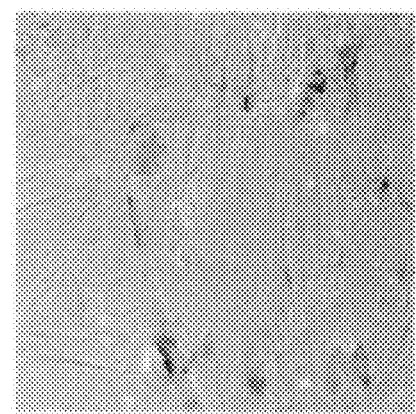
FIG. 11B
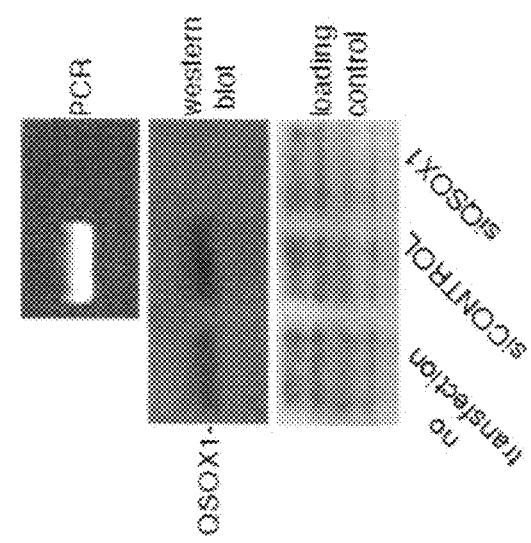
FIG. 11C sICONTROL
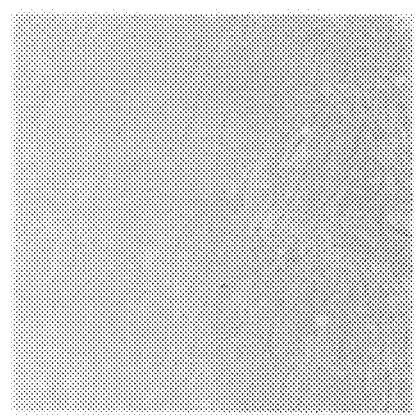
FIG. 11D siQSOX1
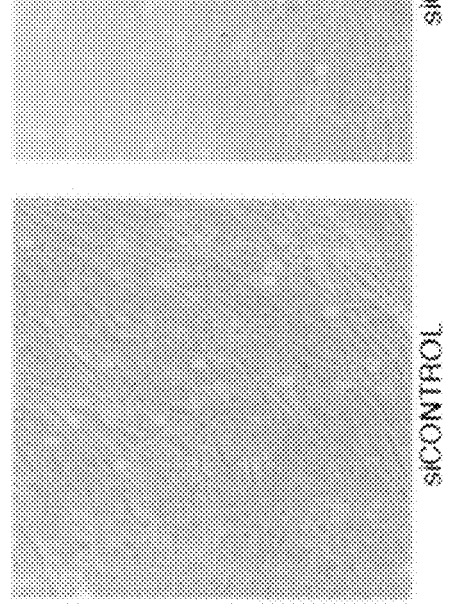
FIG. 11E senescent cells

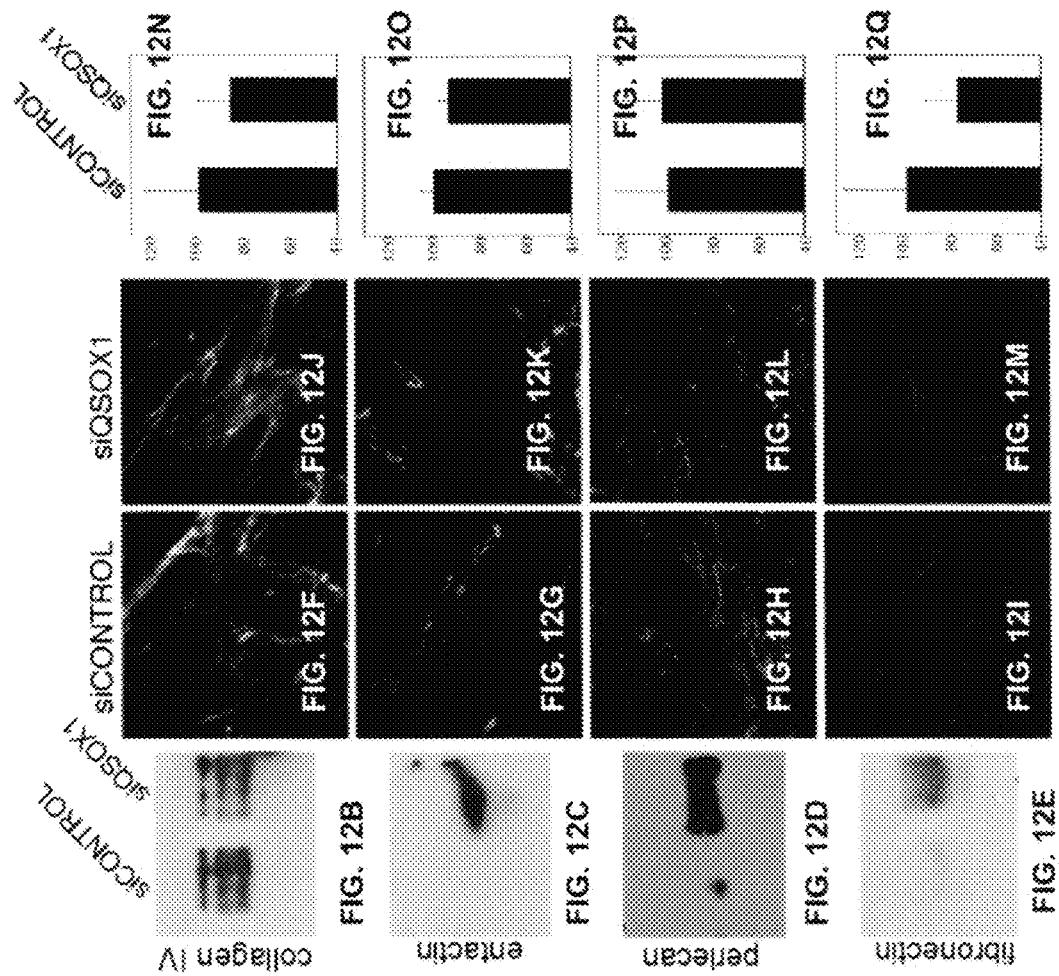
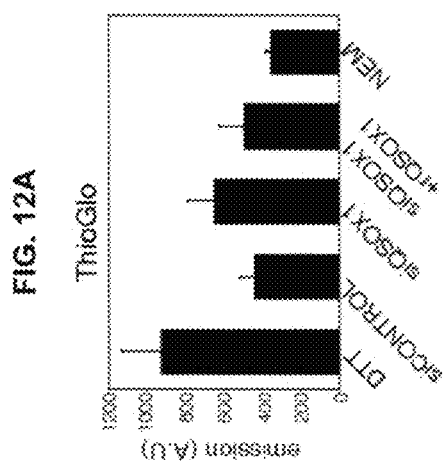

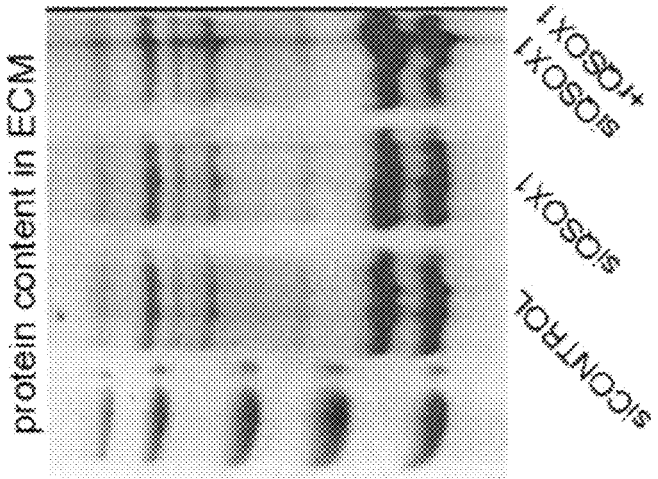
FIG. 13F
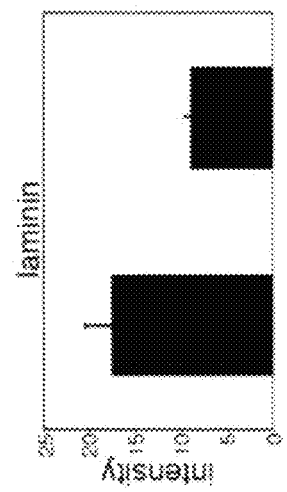
FIG. 13A
FIG. 13B
FIG. 13C
FIG. 13D
FIG. 13E

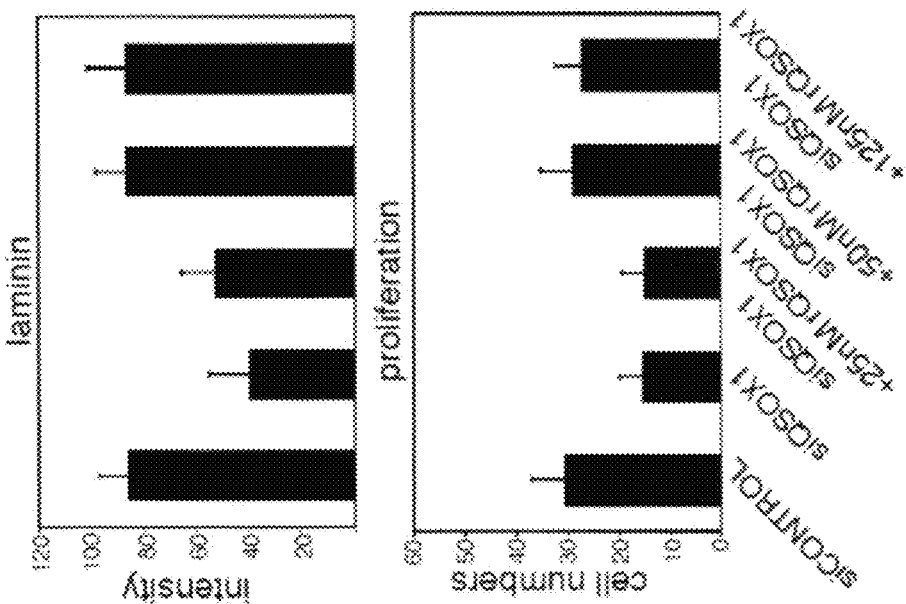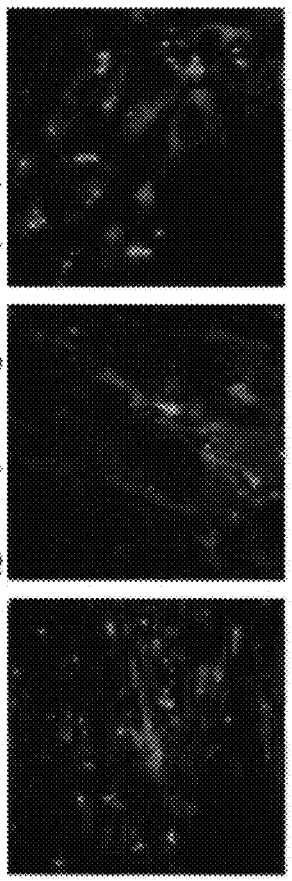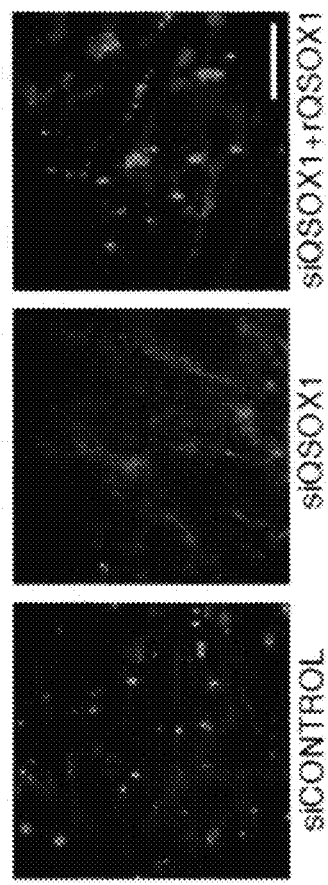

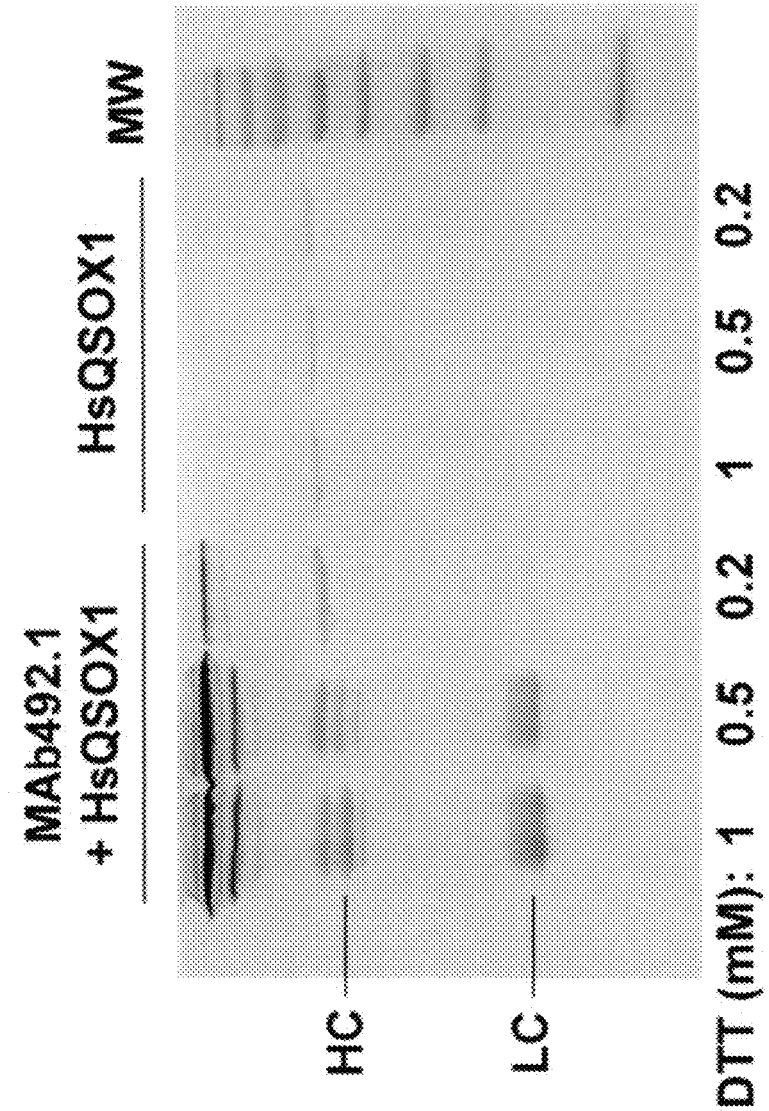

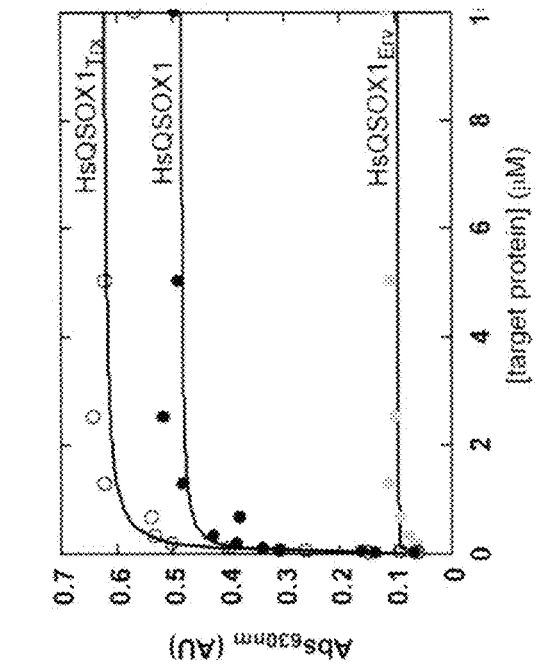
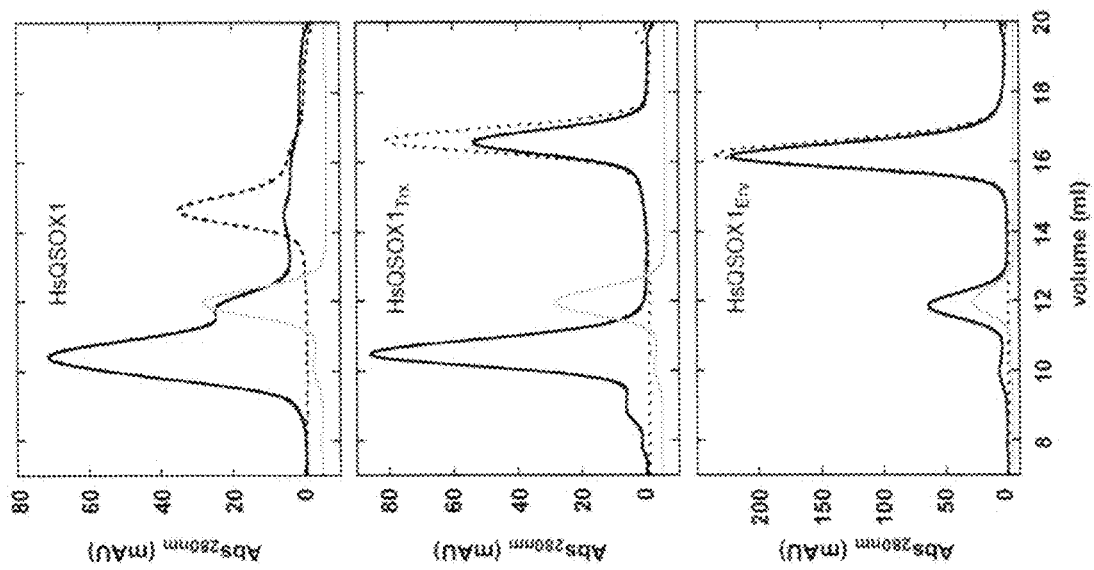
FIG. 16A
FIG. 16B
FIG. 16C
FIG. 16D

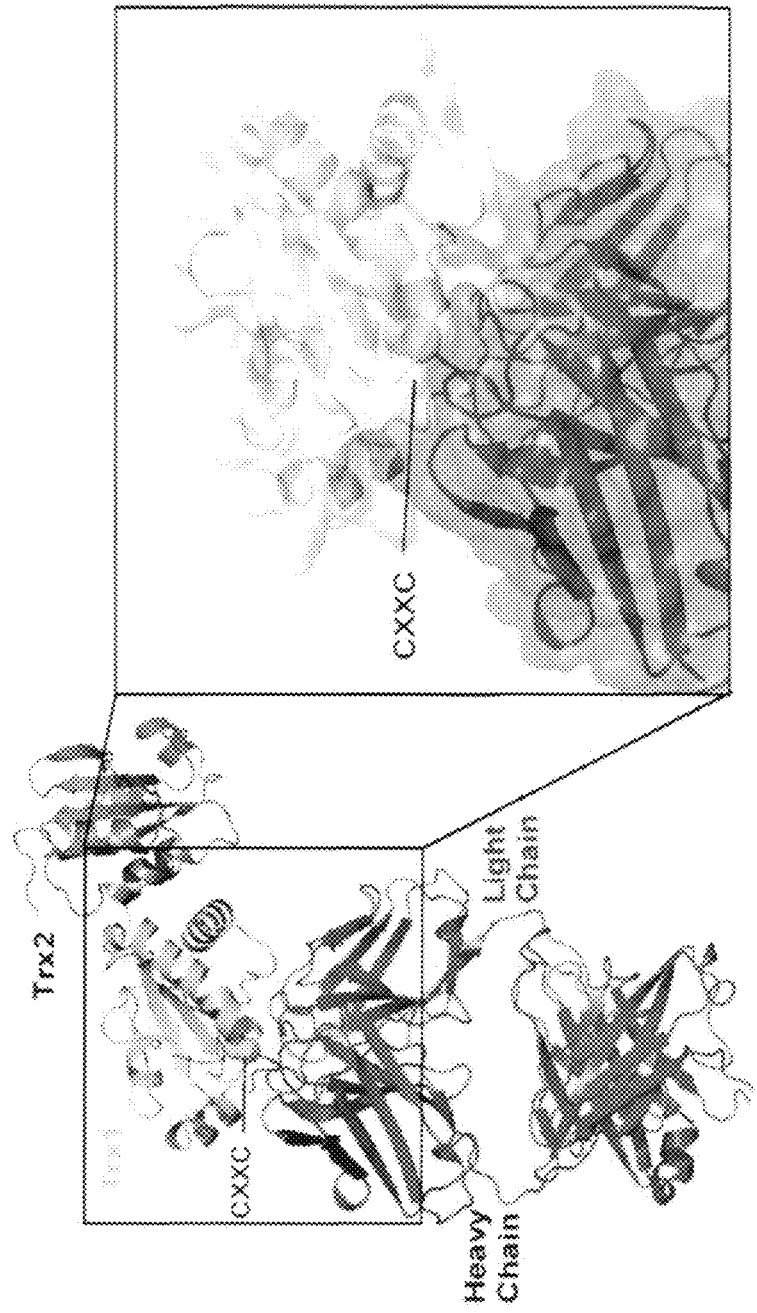

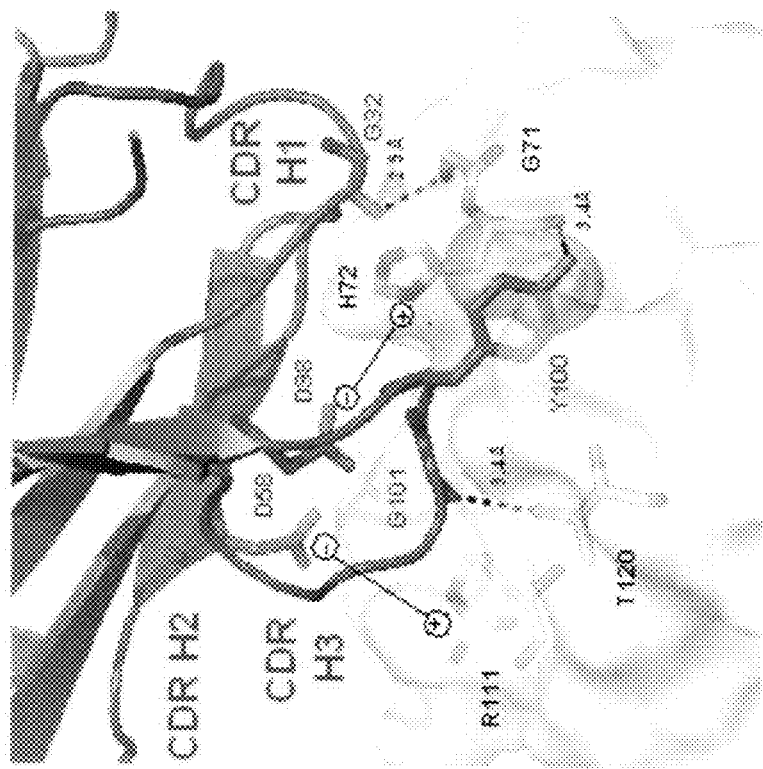
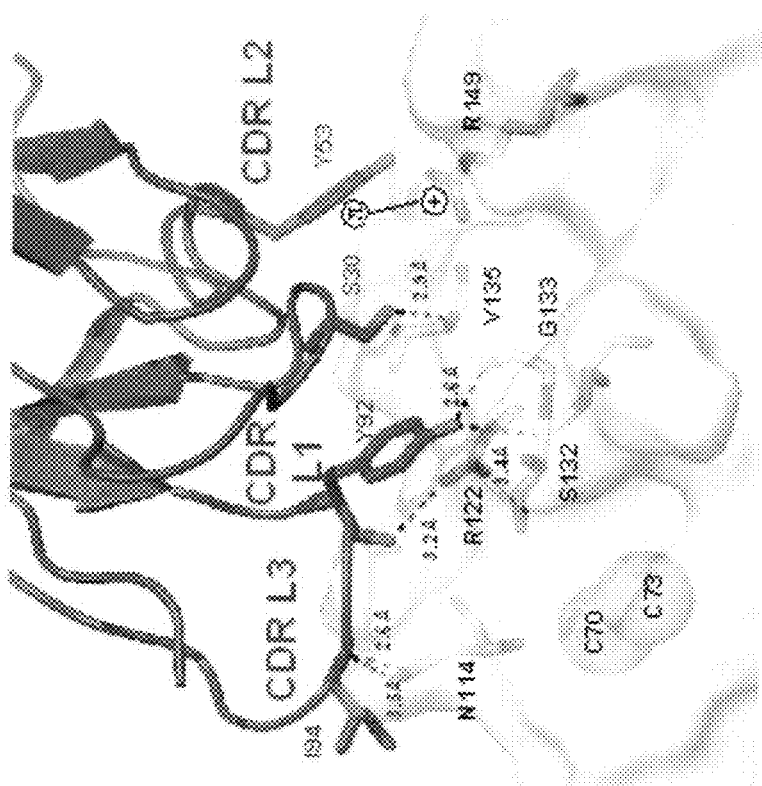
FIG. 20B
FIG. 20A

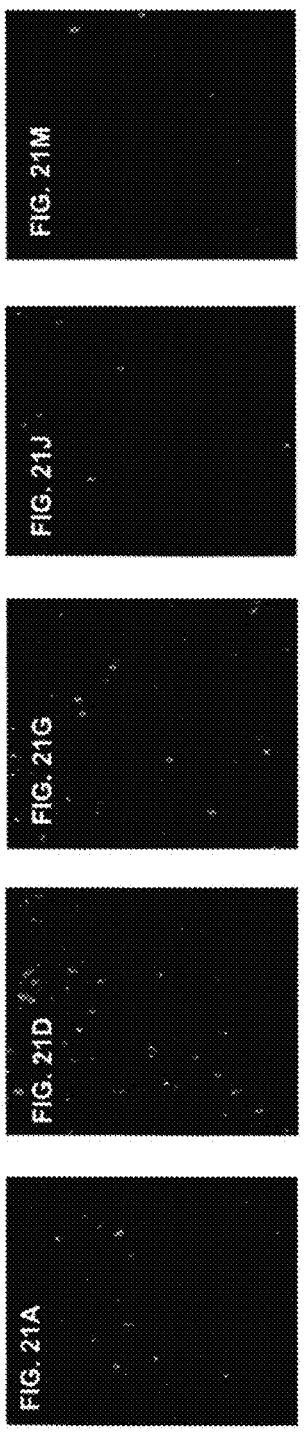

FIG. 25

|  |  |  |  | SEQ ID NO: |
|---|---|---|---|---|
| Human | 69 WCGHCIAFAPT | 79..108 | AVCRDFNIPGFPTVRFFKAFTKNGSGAVFPVAGADVQTLRER | 149 3 |
| Guinea pig | 69 WCGHCIAFAPT | 80..109 | AVCRDFNIAGFPSVRFFKAFSNNSTGTTLPVAGANVQMLRER | 150 41 |
| Rat | 69 WCGHCIAFAPT | 82..111 | AVCRDFNIAGFPTVRFFKAFSKNGTGTALPAAGANVQTLRMR | 152 42 |
| Mouse | 69 WCGHCIAFAPT | 82..111 | AVCRDFNIAGFPTVRFFQAFTKNGSGATPGAGANVQTLRER | 152 43 |

SEQUENCE LISTING

```
<160> NUMBER OF SEQ ID NOS: 43

<210> SEQ ID NO 1
<211> LENGTH: 3316
<212> TYPE: DNA
<213> ORGANISM: Homo sapiens

<400> SEQUENCE: 1
ggaggcaggc ggtgccgcgg cgccgggacc cgactcatcc ggtgcttgcg tgtggtggtg      60
agcgcagcgc cgaggatgag gaggtgcaac agcggctccg ggccgccgcc gtcgctgctg     120
ctgctgctgc tgtggctgct cgcggttccc ggcgctaacg cggccccgcg gtcggcgctc     180
tattcgcctt ccgacccgct gacgctgctg caggcggaca cggtgcgcgg cgcggtgctg     240
ggctcccgca gcgcctgggc cgtggagttc ttcgcctcct ggtgcggcca ctgcatcgcc     300
ttcgccccga cgtggaaggc gctggccgaa gacgtcaaag cctggaggcc ggccctgtat     360
ctcgccgccc tggactgtgc tgaggagacc aacagtgcag tctgcagaga cttcaacatc     420
cctggcttcc cgactgtgag gttcttcaag gcctttacca agaacggctc gggagcagta     480
tttccagtgg ctggtgctga cgtgcagaca ctgcgggaga ggctcattga cgccctggag     540
tcccatcatg acacgtggcc cccagcctgt cccccactgg agcctgccaa gctggaggag     600
attgatggat tctttgcgag aaataacgaa gagtacctgg ctctgatctt tgaaaaggga     660
ggctcctacc tgggtagaga ggtggctctg gacctgtccc agcacaaagg cgtggcggtg     720
cgcagggtgc tgaacacaga ggccaatgtg gtgagaaagt ttggtgtcac cgacttcccc     780
tcttgctacc tgctgttccg gaatggctct gtctcccgag tccccgtgct catggaatcc     840
aggtccttct ataccgctta cctgcagaga ctctctgggc tcaccaggga ggctgcccag     900
```

```
accacagttg caccaaccac tgctaacaag atagctccca ctgtttggaa attggcagat    960
cgctccaaga tctacatggc tgacctggaa tctgcactgc actacatcct gcggatagaa   1020
gtgggcaggt tcccggtcct ggaagggcag cgcctggtgg ccctgaaaaa gtttgtggca   1080
gtgctggcca agtatttccc tggccggccc ttagtccaga acttcctgca ctccgtgaat   1140
gaatggctca agaggcagaa gagaaataaa attccctaca gtttctttaa aactgccctg   1200
gacgacagga aagagggtgc cgttcttgcc aagaaggtga actggattgg ctgccagggg   1260
agtgagccgc atttccgggg cttccctgc tccctgtggg tcctcttcca cttcttgact    1320
gtgcaggcag ctcggcaaaa tgtagaccac tcacaggaag cagccaaggc caaggaggtc   1380
ctcccagcca tccgaggcta cgtgcactac ttcttcggct gccgagactg cgctagccac   1440
ttcgagcaga tggctgctgc ctccatgcac cgggtgggga gtcccaacgc cgctgtcctc   1500
tggctctggt ctagccacaa cagggtcaat gctcgccttg caggtgcccc cagcgaggac   1560
ccccagttcc ccaaggtgca gtggccaccc cgtgaacttt gttctgcctg ccacaatgaa   1620
cgcctggatg tgcccgtgtg ggacgtggaa gccaccctca acttcctcaa ggcccacttc   1680
tccccaagca acatcatcct ggacttccct gcagctgggt cagctgcccg agggatgtg    1740 cagaatgtgg cagccgcccc agagctggcg atgggagccc tggagctgga aagccggaat   1800
tcaactctgg accctgggaa gcctgagatg atgaagtccc ccacaaacac caccccacat   1860
gtgccggctg agggacctga ggcaagtcga ccccgaagc tgcaccctgg cctcagagct    1920
gcaccaggcc aggagcctcc tgagcacatg gcagagcttc agaggaatga gcaggagcag   1980
ccgcttgggc agtggcactt gagcaagcga gacacagggg ctgcattgct ggctgagtcc   2040
agggctgaga agaaccgcct ctggggccct ttggaggtca ggcgcgtggg ccgcagctcc   2100
aagcagctgg tcgacatccc tgagggccag ctggaggccc gagctggacg gggccgaggc   2160
cagtggctgc aggtgctggg aggggcttc tcttacctgg acatcagcct ctgtgtgggg    2220
ctctattccc tgtccttcat gggcctgctg gccatgtaca cctacttcca ggccaagata   2280
agggccctga gggccatgc tggccaccct gcagcctgaa ccactggggg aggaggcggg    2340
agagggagct gccatctcta ggcacctcaa gcccctgac cccattccct cccctcccac    2400
cccttgctcc ttgtctggcc tagaagtgtg ggaaattcag gaaaacgagt tgctccagtg   2460
aagcttcttg gggttgctag acagagagc tcctttgaca caaaagacag gagcagggtc    2520
caggttcccc tgctgtgcag ggagggcagc cccgggcagt gggcataggg cagctcagtc   2580
cctggcctct tagcaccaca ttcctgtttt tcagcttatt tgaagtcctg cctcattctc   2640 actgagcct cagtctctcc tgcttggtct tggccctcaa ctggggcaag tgaagccaga    2700
ggagggtccc ccagctgggt gggctggaat ggaactcctc actagctgct ggggctccgc   2760
ccaccctgct cccttccgga caatgaagaa gcctttgcac cctgggagga aggaccaccc   2820
cgggccctct atgcctggcc agcctccagc tcctcagacc tcctgggtgg ggtttggctt   2880
cagggtgggg tttggaagct tctggaagtc gtgctggtct cccaggtgag gcaagccatg   2940
gttgctgggc tgtagggtga gtggcttgct tggtgggacc tgacgagttg gtggcatggg   3000
aaggatgtgg gtctctagtg ccttgccctg gcttagctgc aggagaagat ggctgctttc   3060
acttcccccc attgagctct gctccctctg agcctggtct tttgtccttt tttattttgg   3120
tctccaagat gaatgctcat ctttggaggg tgccaggtag aagctaggga ggggagtgtc   3180
ttctctctcc aggtttcacc ttccagtgtg cagaagttag aagggtctgg cgggggcagt   3240
```

```
gccttacaca tgcttgattc ccacgctacc ccctgccttg ggaggtgtgt ggaataaatt    3300
atttttgtta aggcaa                                                    3316

<210> SEQ ID NO 2
<211> LENGTH: 2583
<212> TYPE: DNA
<213> ORGANISM: Homo sapiens

<400> SEQUENCE: 2
ggaggcaggc ggtgccgcgg cgccgggacc cgactcatcc ggtgcttgcg tgtggtggtg      60
agcgcagcgc cgaggatgag gaggtgcaac agcggctccg ggccgccgcc gtcgctgctg     120
ctgctgctgc tgtggctgct cgcggttccc ggcgctaacg cggcccgcg gtcggcgctc      180 tattcgcctt ccgacccgct gacgctgctg caggcggaca cggtgcgcgg cgcggtgctg     240
ggctcccgca gcgcctgggc cgtggagttc ttcgcctcct ggtgcggcca ctgcatcgcc     300
ttcgccccga cgtggaaggc gctggccgaa gacgtcaaag cctggaggcc ggccctgtat     360
ctcgccgccc tggactgtgc tgaggagacc aacagtgcag tctgcagaga cttcaacatc     420
cctggcttcc cgactgtgag gttcttcaag gcctttacca agaacggctc gggagcagta     480
tttccagtgg ctggtgctga cgtgcagaca ctgcgggaga ggctcattga cgccctggag     540
tcccatcatg acacgtggcc cccagcctgt cccccactgg agcctgccaa gctggaggag     600
attgatggat tcttttgcgag aaataacgaa gagtacctgg ctctgatctt tgaaaaggga     660
ggctcctacc tgggtagaga ggtggctctg gacctgtccc agcacaaagg cgtggcggtg     720
cgcagggtgc tgaacacaga ggccaatgtg gtgagaaagt ttggtgtcac cgacttcccc     780
tcttgctacc tgctgttccg gaatggctct gtctcccgag tccccgtgct catggaatcc     840
aggtccttct ataccgctta cctgcagaga ctctctgggc tcaccaggga ggctgcccag     900
accacagttg caccaaccac tgctaacaag atagctccca ctgtttggaa attggcagat     960
cgctccaaga tctacatggc tgacctggaa tctgcactgc actacatcct gcggatagaa    1020
gtgggcaggt tcccggtcct ggaagggcag cgcctggtgg ccctgaaaaa gtttgtggca    1080
gtgctggcca gtatttccc tggccggccc ttagtccaga acttcctgca ctccgtgaat    1140
gaatggctca agaggcagaa gagaaataaa attccctaca gtttctttaa aactgccctg    1200
gacgacagga aagagggtgc cgttcttgcc aagaaggtga actggattgg ctgccagggg    1260
agtgagccgc atttccgggg cttttccctgc tccctgtggg tcctcttcca cttcttgact    1320
gtgcaggcag ctcggcaaaa tgtagaccac tcacaggaag cagccaaggc caaggaggtc    1380
ctcccagcca tccgaggcta cgtgcactac ttcttcggct gccgagactg cgctagccac    1440
ttcgagcaga tggctgctgc ctccatgcac cgggtgggga gtcccaacgc cgctgtcctc    1500
tggctctggt ctagccacaa cagggtcaat gctcgccttg caggtgcccc cagcgaggac    1560
ccccagttcc ccaaggtgca gtggccaccc cgtgaacttt gttctgcctg ccacaatgaa    1620
cgcctggatg tgcccgtgtg ggacgtggaa gccaccctca acttcctcaa ggcccacttc    1680
tccccaagca acatcatcct ggacttccct gcagctgggt cagctgcccg gagggatgtg    1740
cagaatgtgg cagccgcccc agagctgcgc atgggagccc tggagctgga aagcggaat    1800 tcaactctgg accctgggaa gctgagatg atgaagtccc ccacaaacac caccccacat    1860
gtgccggctg agggacctga gcttatttga agtcctgcct cattctcact ggagcctcag    1920
tctctcctgc ttggtcttgg ccctcaactg gggcaagtga agccagagga gggtcccca    1980 gctgggtggg ctggaatgga actcctcact agctgctggg gctccgccca ccctgctccc    2040
```

-continued

```
ttccggacaa tgaagaagcc tttgcaccct gggaggaagg accaccccgg gccctctatg    2100
cctggccagc ctccagctcc tcagacctcc tgggtgggt ttggcttcag ggtggggttt    2160
ggaagcttct ggaagtcgtg ctggtctccc aggtgaggca agccatggtt gctgggctgt    2220
agggtgagtg gcttgcttgg tgggacctga cgagttggtg gcatgggaag gatgtgggtc    2280
tctagtgcct tgccctggct tagctgcagg agaagatggc tgctttcact tccccccatt    2340
gagctctgct ccctctgagc ctggtctttt gtccttttt atttggtct ccaagatgaa    2400 tgctcatctt tggagggtgc caggtagaag ctagggaggg gagtgtcttc tctctccagg    2460
tttcaccttc cagtgtgcag aagttagaag ggtctggcgg gggcagtgcc ttacacatgc    2520
ttgattccca cgctaccccc tgccttggga ggtgtgtgga ataaattatt tttgttaagg    2580
caa                                                                 2583
```

```
<210> SEQ ID NO 3
<211> LENGTH: 747
<212> TYPE: PRT
<213> ORGANISM: Homo sapiens

<400> SEQUENCE: 3

Met Arg Arg Cys Asn Ser Gly Ser Gly Pro Pro Ser Leu Leu Leu
1               5                   10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Leu Gln Ala Asp
        35                  40                  45

Thr Val Arg Gly Ala Val Leu Gly Ser Arg Ser Ala Trp Ala Val Glu
    50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
        115                 120                 125

Lys Asn Gly Ser Gly Ala Val Phe Pro Val Ala Gly Ala Asp Val Gln
    130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
        195                 200                 205

Gln His Lys Gly Val Ala Val Arg Arg Val Leu Asn Thr Glu Ala Asn
    210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270
```

```
Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
        290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
        355                 360                 365

Ser Phe Phe Lys Thr Ala Leu Asp Asp Arg Lys Glu Gly Ala Val Leu
370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
        435                 440                 445

Cys Arg Asp Cys Ala Ser His Phe Glu Gln Met Ala Ala Ala Ser Met
450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Arg Glu Leu Cys Ser Ala Cys
            500                 505                 510

His Asn Glu Arg Leu Asp Val Pro Val Trp Asp Val Glu Ala Thr Leu
        515                 520                 525

Asn Phe Leu Lys Ala His Phe Ser Pro Ser Asn Ile Ile Leu Asp Phe
530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
            565                 570                 575

Thr Leu Asp Pro Gly Lys Pro Glu Met Met Lys Ser Pro Thr Asn Thr
        580                 585                 590

Thr Pro His Val Pro Ala Glu Gly Pro Glu Ala Ser Arg Pro Pro Lys
595                 600                 605

Leu His Pro Gly Leu Arg Ala Ala Pro Gly Gln Glu Pro Pro Glu His
            610                 615                 620

Met Ala Glu Leu Gln Arg Asn Glu Gln Glu Gln Pro Leu Gly Gln Trp
625                 630                 635                 640

His Leu Ser Lys Arg Asp Thr Gly Ala Ala Leu Leu Ala Glu Ser Arg
                645                 650                 655

Ala Glu Lys Asn Arg Leu Trp Gly Pro Leu Glu Val Arg Arg Val Gly
            660                 665                 670

Arg Ser Ser Lys Gln Leu Val Asp Ile Pro Glu Gly Gln Leu Glu Ala
        675                 680                 685
```

```
Arg Ala Gly Arg Gly Arg Gly Gln Trp Leu Gln Val Leu Gly Gly Gly
    690             695                 700
Phe Ser Tyr Leu Asp Ile Ser Leu Cys Val Gly Leu Tyr Ser Leu Ser
705             710                 715                 720
Phe Met Gly Leu Leu Ala Met Tyr Thr Tyr Phe Gln Ala Lys Ile Arg
            725                 730                 735
Ala Leu Lys Gly His Ala Gly His Pro Ala Ala
            740                 745
```

<210> SEQ ID NO 4
<211> LENGTH: 604
<212> TYPE: PRT
<213> ORGANISM: Homo sapiens

<400> SEQUENCE: 4

```
Met Arg Arg Cys Asn Ser Gly Ser Gly Pro Pro Ser Leu Leu Leu
1               5                   10                  15
Leu Leu Leu Trp Leu Leu Ala Val Pro Gly Ala Asn Ala Ala Pro Arg
            20                  25                  30
Ser Ala Leu Tyr Ser Pro Ser Asp Pro Leu Thr Leu Leu Gln Ala Asp
            35                  40                  45
Thr Val Arg Gly Ala Val Leu Gly Ser Arg Ser Ala Trp Ala Val Glu
50                  55                  60
Phe Phe Ala Ser Trp Cys Gly His Cys Ile Ala Phe Ala Pro Thr Trp
65                  70                  75                  80
Lys Ala Leu Ala Glu Asp Val Lys Ala Trp Arg Pro Ala Leu Tyr Leu
                85                  90                  95
Ala Ala Leu Asp Cys Ala Glu Glu Thr Asn Ser Ala Val Cys Arg Asp
                100                 105                 110
Phe Asn Ile Pro Gly Phe Pro Thr Val Arg Phe Phe Lys Ala Phe Thr
            115                 120                 125
Lys Asn Gly Ser Gly Ala Val Phe Pro Val Ala Gly Ala Asp Val Gln
            130                 135                 140
Thr Leu Arg Glu Arg Leu Ile Asp Ala Leu Glu Ser His His Asp Thr
145                 150                 155                 160
Trp Pro Pro Ala Cys Pro Pro Leu Glu Pro Ala Lys Leu Glu Glu Ile
                165                 170                 175
Asp Gly Phe Phe Ala Arg Asn Asn Glu Glu Tyr Leu Ala Leu Ile Phe
            180                 185                 190
Glu Lys Gly Gly Ser Tyr Leu Gly Arg Glu Val Ala Leu Asp Leu Ser
            195                 200                 205
Gln His Lys Gly Val Ala Val Arg Arg Val Leu Asn Thr Glu Ala Asn
            210                 215                 220
Val Val Arg Lys Phe Gly Val Thr Asp Phe Pro Ser Cys Tyr Leu Leu
225                 230                 235                 240
Phe Arg Asn Gly Ser Val Ser Arg Val Pro Val Leu Met Glu Ser Arg
                245                 250                 255
Ser Phe Tyr Thr Ala Tyr Leu Gln Arg Leu Ser Gly Leu Thr Arg Glu
            260                 265                 270
Ala Ala Gln Thr Thr Val Ala Pro Thr Thr Ala Asn Lys Ile Ala Pro
            275                 280                 285
Thr Val Trp Lys Leu Ala Asp Arg Ser Lys Ile Tyr Met Ala Asp Leu
            290                 295                 300
Glu Ser Ala Leu His Tyr Ile Leu Arg Ile Glu Val Gly Arg Phe Pro
305                 310                 315                 320
```

```
Val Leu Glu Gly Gln Arg Leu Val Ala Leu Lys Lys Phe Val Ala Val
            325                 330                 335

Leu Ala Lys Tyr Phe Pro Gly Arg Pro Leu Val Gln Asn Phe Leu His
        340                 345                 350

Ser Val Asn Glu Trp Leu Lys Arg Gln Lys Arg Asn Lys Ile Pro Tyr
    355                 360                 365

Ser Phe Phe Lys Thr Ala Leu Asp Asp Arg Lys Glu Gly Ala Val Leu
370                 375                 380

Ala Lys Lys Val Asn Trp Ile Gly Cys Gln Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
        435                 440                 445

Cys Arg Asp Cys Ala Ser His Phe Glu Gln Met Ala Ala Ala Ser Met
    450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Pro Arg Glu Leu Cys Ser Ala Cys
            500                 505                 510

His Asn Glu Arg Leu Asp Val Pro Val Trp Asp Val Glu Ala Thr Leu
        515                 520                 525

Asn Phe Leu Lys Ala His Phe Ser Pro Ser Asn Ile Ile Leu Asp Phe
530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
                565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Leu Ile
        595                 600

<210> SEQ ID NO 5
<211> LENGTH: 1576
<212> TYPE: DNA
<213> ORGANISM: Artificial sequence
<220> FEATURE:
<223> OTHER INFORMATION: Nucleic acid sequence of human QSOX (133-546)

<400> SEQUENCE: 5
atgggccatc atcaccacca tcaccatatg tcggcgctct attcgccttc cgacccgctg      60
acgctgctgc aggcggacac ggtgcgcggc cggtgctgg gctcccgcag cgcctgggcc     120
gtggagttct tcgcctcctg gtgcggccac tgcatcgcct cgccccgac gtggaaggcg     180 ctggccgaag acgtcaaagc ctggaggccg ccctgtatc tcgccgccct ggactgtgct     240
gaggagacca cagtgcagt ctgcagagac ttcaacatcc ctggcttccc gactgtgagg     300
ttcttcaagg cctttaccaa gaacggctca ggagcagtat ttccagtggc tggtgctgac     360
gtgcagacgc tgcgggagag gctcattgac gccctggagt cccatcatga cacgtggccc     420
ccagcctgtc ccccactgga gcctgccaag ctggaggaga ttgatggatt ctttgcgaga     480
```

```
aataacgaag agtacctggc tctgatcttt gaaaagggag gctcctacct ggctagagag     540
gtggctctgg acctgtccca gcacaaaggc gtggcggtgc gcagggtgct gaacacagag     600
gccaatgtgg tgagaaagtt tggtgtcacc gacttcccct cttgctacct gctgttccgg     660
aatggctctg tctcccgagt ccccgtgctc atggaatcca ggtccttcta taccgcttac     720
ctgcagagac tctctgggct aaccagggag gctgcccaga ccacagttgc accaaccact     780
gctaacaaga tagctcccac tgtttggaaa ttggcagatc gctccaagat ctacatggct     840
gacctggaat ctgcactgca ctacatcctg cggatagaag tgggcaggtt cccggtcctg     900
gaagggcagc gcctggtggc cctgaaaaag tttgtggcag tgctggccaa gtatttccct     960
ggccggccct tagtccagaa cttcctgcac tccgtgaatg aatggctcaa gaggcagaag    1020
agaaataaaa ttccctacag tttctttaaa actgccctgg acgacaggaa agagggtgcc    1080
gttctcgcca agaaggtgaa ctggattggc tgccagggga gtgagccgca tttccggggc    1140
tttccctgct ccctgtgggt tctttttcac ttcttgactg tgcaggcagc tcggcaaaat    1200
gtagaccact cacaggaagc agccaaggcc aaggaggtcc tcccagccat ccgaggctac    1260
gtgcactact tcttcggctg ccgagactgc gctagccact tcgagcagat ggctgctgcc    1320
tccatgcacc gggtggggag tcccaacgcc gctgtcctct ggctctggtc tagccacaac    1380
agggtcaatg ctcgccttgc aggtgccccc agcgaggacc cccagttccc caaggtgcag    1440
tggccacccc gtgaactttg ttctgcctgc acaatgaac gcctggatgt gcccgtgtgg    1500
gacgtggaag ccaccctcaa cttcctcaag gcccacttct ccccaagcaa catcatcctg    1560
gacttccctg cataag                                                    1576
```

<210> SEQ ID NO 6
<211> LENGTH: 524
<212> TYPE: PRT
<213> ORGANISM: Artificial sequence
<220> FEATURE:
<223> OTHER INFORMATION: Amino acid sequence of human QSOX (133-546)

<400> SEQUENCE: 6

```
Met Gly His His His His His His Met Ser Ala Leu Tyr Ser Pro
1               5                   10                  15

Ser Asp Pro Leu Thr Leu Leu Gln Ala Asp Thr Val Arg Gly Ala Val
            20                  25                  30

Leu Gly Ser Arg Ser Ala Trp Ala Val Glu Phe Phe Ala Ser Trp Cys
        35                  40                  45

Gly His Cys Ile Ala Phe Ala Pro Thr Trp Lys Ala Leu Ala Glu Asp
    50                  55                  60

Val Lys Ala Trp Arg Pro Ala Leu Tyr Leu Ala Leu Asp Cys Ala
65                  70                  75                  80

Glu Glu Thr Asn Ser Ala Val Cys Arg Asp Phe Asn Ile Pro Gly Phe
                85                  90                  95

Pro Thr Val Arg Phe Phe Lys Ala Phe Thr Lys Asn Gly Ser Gly Ala
            100                 105                 110

Val Phe Pro Val Ala Gly Ala Asp Val Gln Thr Leu Arg Glu Arg Leu
        115                 120                 125

Ile Asp Ala Leu Glu Ser His His Asp Thr Trp Pro Pro Ala Cys Pro
    130                 135                 140

Pro Leu Glu Pro Ala Lys Leu Glu Glu Ile Asp Gly Phe Phe Ala Arg
145                 150                 155                 160
```

```
Asn Asn Glu Glu Tyr Leu Ala Leu Ile Phe Glu Lys Gly Gly Ser Tyr
            165                 170                 175
Leu Ala Arg Glu Val Ala Leu Asp Leu Ser Gln His Lys Gly Val Ala
        180                 185                 190
Val Arg Arg Val Leu Asn Thr Glu Ala Asn Val Val Arg Lys Phe Gly
    195                 200                 205
Val Thr Asp Phe Pro Ser Cys Tyr Leu Leu Phe Arg Asn Gly Ser Val
210                 215                 220
Ser Arg Val Pro Val Leu Met Glu Ser Arg Ser Phe Tyr Thr Ala Tyr
225                 230                 235                 240
Leu Gln Arg Leu Ser Gly Leu Thr Arg Glu Ala Ala Gln Thr Thr Val
            245                 250                 255
Ala Pro Thr Thr Ala Asn Lys Ile Ala Pro Thr Val Trp Lys Leu Ala
        260                 265                 270
Asp Arg Ser Lys Ile Tyr Met Ala Asp Leu Glu Ser Ala Leu His Tyr
    275                 280                 285
Ile Leu Arg Ile Glu Val Gly Arg Phe Pro Val Leu Glu Gly Gln Arg
290                 295                 300
Leu Val Ala Leu Lys Lys Phe Val Ala Val Leu Ala Lys Tyr Phe Pro
305                 310                 315                 320
Gly Arg Pro Leu Val Gln Asn Phe Leu His Ser Val Asn Glu Trp Leu
            325                 330                 335
Lys Arg Gln Lys Arg Asn Lys Ile Pro Tyr Ser Phe Phe Lys Thr Ala
        340                 345                 350
Leu Asp Asp Arg Lys Glu Gly Ala Val Leu Ala Lys Lys Val Asn Trp
    355                 360                 365
Ile Gly Cys Gln Gly Ser Glu Pro His Phe Arg Gly Phe Pro Cys Ser
370                 375                 380
Leu Trp Val Leu Phe His Phe Leu Thr Val Gln Ala Ala Arg Gln Asn
385                 390                 395                 400
Val Asp His Ser Gln Glu Ala Ala Lys Ala Lys Glu Val Leu Pro Ala
            405                 410                 415
Ile Arg Gly Tyr Val His Tyr Phe Phe Gly Cys Arg Asp Cys Ala Ser
        420                 425                 430
His Phe Glu Gln Met Ala Ala Ser Met His Arg Val Gly Ser Pro
    435                 440                 445
Asn Ala Ala Val Leu Trp Leu Trp Ser Ser His Asn Arg Val Asn Ala
450                 455                 460
Arg Leu Ala Gly Ala Pro Ser Glu Asp Pro Gln Phe Pro Lys Val Gln
465                 470                 475                 480
Trp Pro Pro Arg Glu Leu Cys Ser Ala Cys His Asn Glu Arg Leu Asp
            485                 490                 495
Val Pro Val Trp Asp Val Glu Ala Thr Leu Asn Phe Leu Lys Ala His
        500                 505                 510
Phe Ser Pro Ser Asn Ile Ile Leu Asp Phe Pro Ala
    515                 520

<210> SEQ ID NO 7
<211> LENGTH: 107
<212> TYPE: PRT
<213> ORGANISM: Artificial sequence
<220> FEATURE:
<223> OTHER INFORMATION: MAb492.1 variable light amino acid sequence
```

<400> SEQUENCE: 7

Asp Val Val Met Thr Gln Thr His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Ser Gly Gln Ser Pro Lys Leu Leu Ile
        35                  40                  45

His Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ile Pro Leu
                85                  90                  95

Thr Phe Gly Ala Gly Thr Lys Leu Glu Leu Lys
            100                 105

<210> SEQ ID NO 8
<211> LENGTH: 118
<212> TYPE: PRT
<213> ORGANISM: Artificial sequence
<220> FEATURE:
<223> OTHER INFORMATION: MAb492.1 variable heavy amino acid sequence

<400> SEQUENCE: 8

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Ser Pro Gly Lys Gly Leu Glu Trp Leu
        35                  40                  45

Gly Met Ile Trp Gly Asp Gly Arg Thr Asp Tyr Lys Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Arg Tyr Phe Cys Ala
                85                  90                  95

Ser Asp Tyr Tyr Gly Ser Gly Ser Phe Ala Tyr Trp Gly Gln Gly Thr
            100                 105                 110

Leu Val Thr Val Ser Ala
        115

<210> SEQ ID NO 9
<211> LENGTH: 18
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 9

Asp Val Val Met Thr Gln Thr His Lys Phe Met Ser Thr Ser Val Gly
1               5                   10                  15

Asp Arg

<210> SEQ ID NO 10
<211> LENGTH: 24
<212> TYPE: PRT
<213> ORGANISM: Artificial sequence

```
<220> FEATURE:
<223> OTHER INFORMATION: MAb492.1 representative peptide detected by
      LC-MS/MS

<400> SEQUENCE: 10

Asp Val Val Met Thr Gln Thr His Lys Phe Met Ser Thr Ser Val Gly
1               5                   10                  15

Asp Arg Val Ser Thr Ile Cys Lys
            20

<210> SEQ ID NO 11
<211> LENGTH: 15
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 11

Phe Met Ser Thr Ser Val Gly Asp Arg Val Ser Ile Thr Cys Lys
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 12

Ala Ser Gln Asp Val Ser Thr Ala Val Ala Trp Tyr Gln Gln Lys
1               5                   10                  15

<210> SEQ ID NO 13
<211> LENGTH: 9
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 13

Leu Leu Ile His Ser Ala Ser Tyr Arg
1               5

<210> SEQ ID NO 14
<211> LENGTH: 16
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 14

Asp Val Val Met Thr Gln Thr His Lys Phe Met Ser Thr Ser Val Gly
1               5                   10                  15

<210> SEQ ID NO 15
<211> LENGTH: 17
<212> TYPE: PRT
<213> ORGANISM: Artificial sequence
<220> FEATURE:
<223> OTHER INFORMATION: MAb492.1 representative peptide detected by
      LC-MS/MS
```

-continued

```
<400> SEQUENCE: 15

Met Ser Thr Ser Val Gly Asp Arg Val Ser Ile Thr Cys Lys Ala Ser
1               5                   10                  15

Gln

<210> SEQ ID NO 16
<211> LENGTH: 17
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 16

Gln Gln Lys Ser Gly Gln Ser Pro Lys Leu Leu Ile His Ser Ala Ser
1               5                   10                  15

Tyr

<210> SEQ ID NO 17
<211> LENGTH: 11
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 17

Thr Gly Ser Gly Ser Gly Thr Asp Phe Thr Phe
1               5                   10

<210> SEQ ID NO 18
<211> LENGTH: 12
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 18

Ser Ile Pro Leu Thr Phe Gly Ala Gly Thr Lys Leu
1               5                   10

<210> SEQ ID NO 19
<211> LENGTH: 9
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 19

Ser Leu Thr Gly Tyr Gly Val Asn Trp
1               5

<210> SEQ ID NO 20
<211> LENGTH: 15
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 20

Gly Val Asn Trp Val Arg Gln Ser Pro Gly Lys Gly Leu Glu Trp
1               5                   10                  15
```

-continued

```
<210> SEQ ID NO 21
<211> LENGTH: 10
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 21

Asp Tyr Lys Ser Ala Leu Lys Ser Arg Leu
1               5                   10

<210> SEQ ID NO 22
<211> LENGTH: 16
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 22

Lys Ser Arg Leu Ser Ile Thr Lys Asp Asn Ser Lys Ser Gln Val Phe
1               5                   10                  15

<210> SEQ ID NO 23
<211> LENGTH: 18
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 23

Gln Ser Pro Gly Lys Gly Leu Glu Trp Leu Gly Met Ile Trp Gly Asp
1               5                   10                  15

Gly Arg

<210> SEQ ID NO 24
<211> LENGTH: 13
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 24

Gly Leu Glu Trp Leu Gly Met Ile Trp Gly Asp Gly Arg
1               5                   10

<210> SEQ ID NO 25
<211> LENGTH: 17
<212> TYPE: PRT
<213> ORGANISM: Artificial sequence
<220> FEATURE:
<223> OTHER INFORMATION: MAb492.1 representative peptide detected by
      LC-MS/MS

<400> SEQUENCE: 25

Gly Leu Glu Trp Leu Gly Met Ile Trp Gly Asp Gly Arg Thr Asp Tyr
1               5                   10                  15

Lys

<210> SEQ ID NO 26
<211> LENGTH: 11
<212> TYPE: PRT
<213> ORGANISM: Artificial sequence
```

```
<220> FEATURE:
<223> OTHER INFORMATION: MAb492.1 representative peptide detected by
      LC-MS/MS

<400> SEQUENCE: 26

Met Asn Ser Leu Gln Thr Asp Asp Thr Ala Arg
1               5                   10

<210> SEQ ID NO 27
<211> LENGTH: 214
<212> TYPE: PRT
<213> ORGANISM: Artificial sequence
<220> FEATURE:
<223> OTHER INFORMATION: MAb492.1 light chain amino acid sequence

<400> SEQUENCE: 27

Asp Val Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Ser Gly Gln Ser Pro Lys Leu Leu Ile
        35                  40                  45

His Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ile Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 28
<211> LENGTH: 484
<212> TYPE: PRT
<213> ORGANISM: Artificial sequence
<220> FEATURE:
<223> OTHER INFORMATION: MAb492.1 heavy chain amino acid sequence

<400> SEQUENCE: 28

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Ser Pro Gly Lys Gly Leu Glu Trp Leu
        35                  40                  45
```

-continued

```
Gly Met Ile Trp Gly Asp Gly Arg Thr Asp Tyr Lys Ser Ala Leu Lys
 50                  55                  60

Ser Arg Leu Ser Ile Thr Lys Asp Asn Ser Lys Ser Gln Val Phe Leu
 65                  70                  75                  80

Lys Met Asn Ser Leu Gln Thr Asp Asp Thr Ala Arg Tyr Phe Cys Ala
                 85                  90                  95

Ser Asp Tyr Tyr Gly Ser Gly Ser Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Glu
                165                 170                 175

Ser Asp Leu Tyr Thr Leu Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asn Thr Asn Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys Gln Leu Asp Glu Thr Cys
        435                 440                 445

Ala Glu Ala Gln Asp Gly Glu Leu Asp Gly Leu Trp Thr Thr Ile Thr
    450                 455                 460
```

```
Ile Phe Ile Ser Leu Phe Leu Leu Ser Val Cys Tyr Ser Ala Ala Val
465                 470                 475                 480

Thr Leu Phe Lys

<210> SEQ ID NO 29
<211> LENGTH: 6
<212> TYPE: PRT
<213> ORGANISM: Artificial sequence
<220> FEATURE:
<223> OTHER INFORMATION: MAb492.1 light chain CDR1 amino acid sequence

<400> SEQUENCE: 29

Gln Asp Val Ser Thr Ala
1               5

<210> SEQ ID NO 30
<211> LENGTH: 3
<212> TYPE: PRT
<213> ORGANISM: Artificial sequence
<220> FEATURE:
<223> OTHER INFORMATION: MAb492.1 light chain CDR2 amino acid sequence

<400> SEQUENCE: 30

Ser Ala Ser
1

<210> SEQ ID NO 31
<211> LENGTH: 9
<212> TYPE: PRT
<213> ORGANISM: Artificial sequence
<220> FEATURE:
<223> OTHER INFORMATION: MAb492.1 light chain CDR3 amino acid sequence

<400> SEQUENCE: 31

Gln Gln His Tyr Ser Ile Pro Leu Thr
1               5

<210> SEQ ID NO 32
<211> LENGTH: 8
<212> TYPE: PRT
<213> ORGANISM: Artificial sequence
<220> FEATURE:
<223> OTHER INFORMATION: MAb492.1 heavy chain CDR1 amino acid sequence

<400> SEQUENCE: 32

Gly Phe Ser Leu Thr Gly Tyr Gly
1               5

<210> SEQ ID NO 33
<211> LENGTH: 7
<212> TYPE: PRT
<213> ORGANISM: Artificial sequence
<220> FEATURE:
<223> OTHER INFORMATION: MAb492.1 heavy chain CDR2 amino acid sequence

<400> SEQUENCE: 33

Ile Trp Gly Asp Gly Arg Thr
1               5

<210> SEQ ID NO 34
<211> LENGTH: 12
<212> TYPE: PRT
<213> ORGANISM: Artificial sequence
<220> FEATURE:
<223> OTHER INFORMATION: MAb492.1 heavy chain CDR3 amino acid sequence
```

```
<400> SEQUENCE: 34

Ala Ser Asp Tyr Tyr Gly Ser Gly Ser Phe Ala Tyr
1               5                   10

<210> SEQ ID NO 35
<211> LENGTH: 747
<212> TYPE: PRT
<213> ORGANISM: Artificial sequence
<220> FEATURE:
<223> OTHER INFORMATION: QSOX1 trypsin cleavage product (Lower band)

<400> SEQUENCE: 35

Met Arg Arg Cys Asn Ser Gly Ser Gly Pro Pro Ser Leu Leu Leu
1               5                   10                  15

Leu Leu Leu Trp Leu Leu Ala Val Pro Gly Ala Asn Ala Ala Pro Arg
                20                  25                  30

Ser Ala Leu Tyr Ser Pro Ser Asp Pro Leu Thr Leu Leu Gln Ala Asp
            35                  40                  45

Thr Val Arg Gly Ala Val Leu Gly Ser Arg Ser Ala Trp Ala Val Glu
        50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
        115                 120                 125

Lys Asn Gly Ser Gly Ala Val Phe Pro Val Ala Gly Ala Asp Val Gln
    130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
        195                 200                 205

Gln His Lys Gly Val Ala Val Arg Arg Val Leu Asn Thr Glu Ala Asn
    210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
        275                 280                 285

Thr Val Trp Lys Leu Ala Asp Arg Ser Lys Ile Tyr Met Ala Asp Leu
    290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335
```

```
Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
        355                 360                 365

Ser Phe Phe Lys Thr Ala Leu Asp Asp Arg Lys Glu Gly Ala Val Leu
    370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
                420                 425                 430

Lys Glu Val Leu Pro Ala Ile Arg Gly Tyr Val His Tyr Phe Phe Gly
                435                 440                 445

Cys Arg Asp Cys Ala Ser His Phe Glu Gln Met Ala Ala Ala Ser Met
            450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Pro Arg Glu Leu Cys Ser Ala Cys
                500                 505                 510

His Asn Glu Arg Leu Asp Val Pro Val Trp Asp Val Glu Ala Thr Leu
            515                 520                 525

Asn Phe Leu Lys Ala His Phe Ser Pro Ser Asn Ile Ile Leu Asp Phe
530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
                565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Ala Ser Arg Pro Pro Lys
        595                 600                 605

Leu His Pro Gly Leu Arg Ala Ala Pro Gly Gln Glu Pro Pro Glu His
    610                 615                 620

Met Ala Glu Leu Gln Arg Asn Glu Gln Gln Pro Leu Gly Gln Trp
625                 630                 635                 640

His Leu Ser Lys Arg Asp Thr Gly Ala Ala Leu Leu Ala Glu Ser Arg
                645                 650                 655

Ala Glu Lys Asn Arg Leu Trp Gly Pro Leu Glu Val Arg Arg Val Gly
                660                 665                 670

Arg Ser Ser Lys Gln Leu Val Asp Ile Pro Glu Gly Gln Leu Glu Ala
            675                 680                 685

Arg Ala Gly Arg Gly Arg Gly Gln Trp Leu Gln Val Leu Gly Gly Gly
        690                 695                 700

Phe Ser Tyr Leu Asp Ile Ser Leu Cys Val Gly Leu Tyr Ser Leu Ser
705                 710                 715                 720

Phe Met Gly Leu Leu Ala Met Tyr Thr Tyr Phe Gln Ala Lys Ile Arg
                725                 730                 735

Ala Leu Lys Gly His Ala Gly His Pro Ala Ala
            740                 745
```

<210> SEQ ID NO 36
<211> LENGTH: 747
<212> TYPE: PRT
<213> ORGANISM: Artificial sequence
<220> FEATURE:
<223> OTHER INFORMATION: QSOX1 chemotrypsin cleavage product (Lower band)

<400> SEQUENCE: 36

```
Met Arg Arg Cys Asn Ser Gly Ser Gly Pro Pro Ser Leu Leu Leu
1               5                   10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Gln Ala Asp
            35                  40                  45

Thr Val Arg Gly Ala Val Leu Gly Ser Arg Ser Ala Trp Ala Val Glu
    50                  55                  60

Phe Phe Ala Ser Trp Cys Gly His Cys Ile Ala Phe Ala Pro Thr Trp
65              70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
    130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
    195                 200                 205

Gln His Lys Gly Val Ala Val Arg Arg Val Leu Asn Thr Glu Ala Asn
210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
    275                 280                 285

Thr Val Trp Lys Leu Ala Asp Arg Ser Lys Ile Tyr Met Ala Asp Leu
290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
    355                 360                 365
```

```
Ser Phe Phe Lys Thr Ala Leu Asp Asp Arg Lys Glu Gly Ala Val Leu
    370                 375                 380
Ala Lys Lys Val Asn Trp Ile Gly Cys Gln Gly Ser Glu Pro His Phe
385                 390                 395                 400
Arg Gly Phe Pro Cys Ser Leu Trp Val Leu Phe His Phe Leu Thr Val
                405                 410                 415
Gln Ala Ala Arg Gln Asn Val Asp His Ser Gln Glu Ala Ala Lys Ala
        420                 425                 430
Lys Glu Val Leu Pro Ala Ile Arg Gly Tyr Val His Tyr Phe Phe Gly
            435                 440                 445
Cys Arg Asp Cys Ala Ser His Phe Glu Gln Met Ala Ala Ala Ser Met
    450                 455                 460
His Arg Val Gly Ser Pro Asn Ala Ala Val Leu Trp Leu Trp Ser Ser
465                 470                 475                 480
His Asn Arg Val Asn Ala Arg Leu Ala Gly Ala Pro Ser Glu Asp Pro
                485                 490                 495
Gln Phe Pro Lys Val Gln Trp Pro Pro Arg Glu Leu Cys Ser Ala Cys
        500                 505                 510
His Asn Glu Arg Leu Asp Val Pro Val Trp Asp Val Glu Ala Thr Leu
            515                 520                 525
Asn Phe Leu Lys Ala His Phe Ser Pro Ser Asn Ile Ile Leu Asp Phe
    530                 535                 540
Pro Ala Ala Gly Ser Ala Ala Arg Arg Asp Val Gln Asn Val Ala Ala
545                 550                 555                 560
Ala Pro Glu Leu Ala Met Gly Ala Leu Glu Leu Glu Ser Arg Asn Ser
                565                 570                 575
Thr Leu Asp Pro Gly Lys Pro Glu Met Met Lys Ser Pro Thr Asn Thr
        580                 585                 590
Thr Pro His Val Pro Ala Glu Gly Pro Glu Ala Ser Arg Pro Pro Lys
            595                 600                 605
Leu His Pro Gly Leu Arg Ala Ala Pro Gly Gln Glu Pro Pro Glu His
    610                 615                 620
Met Ala Glu Leu Gln Arg Asn Glu Gln Glu Gln Pro Leu Gly Gln Trp
625                 630                 635                 640
His Leu Ser Lys Arg Asp Thr Gly Ala Ala Leu Leu Ala Glu Ser Arg
                645                 650                 655
Ala Glu Lys Asn Arg Leu Trp Gly Pro Leu Glu Val Arg Arg Val Gly
        660                 665                 670
Arg Ser Ser Lys Gln Leu Val Asp Ile Pro Glu Gly Gln Leu Glu Ala
            675                 680                 685
Arg Ala Gly Arg Gly Arg Gly Gln Trp Leu Gln Val Leu Gly Gly Gly
    690                 695                 700
Phe Ser Tyr Leu Asp Ile Ser Leu Cys Val Gly Leu Tyr Ser Leu Ser
705                 710                 715                 720
Phe Met Gly Leu Leu Ala Met Tyr Thr Tyr Phe Gln Ala Lys Ile Arg
                725                 730                 735
Ala Leu Lys Gly His Ala Gly His Pro Ala Ala
        740                 745

<210> SEQ ID NO 37
<211> LENGTH: 747
<212> TYPE: PRT
<213> ORGANISM: Artificial sequence
<220> FEATURE:
<223> OTHER INFORMATION: QSOX1 trypsin cleavage product (Upper band)
```

<400> SEQUENCE: 37

```
Met Arg Arg Cys Asn Ser Gly Ser Gly Pro Pro Ser Leu Leu Leu
1               5                   10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Gln Ala Asp
            35                  40                  45

Thr Val Arg Gly Ala Val Leu Gly Ser Arg Ser Ala Trp Ala Val Glu
    50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
                115                 120                 125

Lys Asn Gly Ser Gly Ala Val Phe Pro Val Ala Gly Ala Asp Val Gln
                130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
                180                 185                 190

Glu Lys Gly Gly Ser Tyr Leu Gly Arg Glu Val Ala Leu Asp Leu Ser
                195                 200                 205

Gln His Lys Gly Val Ala Val Arg Val Leu Asn Thr Glu Ala Asn
                210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
                260                 265                 270

Ala Ala Gln Thr Thr Val Ala Pro Thr Thr Ala Asn Lys Ile Ala Pro
                275                 280                 285

Thr Val Trp Lys Leu Ala Asp Arg Ser Lys Ile Tyr Met Ala Asp Leu
                290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
                340                 345                 350

Ser Val Asn Glu Trp Leu Lys Arg Gln Lys Arg Asn Lys Ile Pro Tyr
                355                 360                 365

Ser Phe Phe Lys Thr Ala Leu Asp Asp Arg Lys Glu Gly Ala Val Leu
                370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415
```

```
Gln Ala Ala Arg Gln Asn Val Asp His Ser Gln Glu Ala Ala Lys Ala
                420                 425                 430

Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Pro Arg Glu Leu Cys Ser Ala Cys
            500                 505                 510

His Asn Glu Arg Leu Asp Val Pro Val Trp Asp Val Glu Ala Thr Leu
        515                 520                 525

Asn Phe Leu Lys Ala His Phe Ser Pro Ser Asn Ile Ile Leu Asp Phe
530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
                565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Ala Ser Arg Pro Pro Lys
        595                 600                 605

Leu His Pro Gly Leu Arg Ala Ala Pro Gly Gln Glu Pro Pro Glu His
610                 615                 620

Met Ala Glu Leu Gln Arg Asn Glu Gln Glu Gln Pro Leu Gly Gln Trp
625                 630                 635                 640

His Leu Ser Lys Arg Asp Thr Gly Ala Ala Leu Leu Ala Glu Ser Arg
                645                 650                 655

Ala Glu Lys Asn Arg Leu Trp Gly Pro Leu Glu Val Arg Arg Val Gly
            660                 665                 670

Arg Ser Ser Lys Gln Leu Val Asp Ile Pro Glu Gly Gln Leu Glu Ala
        675                 680                 685

Arg Ala Gly Arg Gly Arg Gly Gln Trp Leu Gln Val Leu Gly Gly Gly
690                 695                 700

Phe Ser Tyr Leu Asp Ile Ser Leu Cys Val Gly Leu Tyr Ser Leu Ser
705                 710                 715                 720

Phe Met Gly Leu Leu Ala Met Tyr Thr Tyr Phe Gln Ala Lys Ile Arg
                725                 730                 735

Ala Leu Lys Gly His Ala Gly His Pro Ala Ala
            740                 745

<210> SEQ ID NO 38
<211> LENGTH: 747
<212> TYPE: PRT
<213> ORGANISM: Artificial sequence
<220> FEATURE:
<223> OTHER INFORMATION: QSOX1 chemotrypsin cleavage product (Upper
      band)

<400> SEQUENCE: 38

Met Arg Arg Cys Asn Ser Gly Ser Gly Pro Pro Pro Ser Leu Leu Leu
1               5                   10                  15

Leu Leu Leu Trp Leu Leu Ala Val Pro Gly Ala Asn Ala Ala Pro Arg
            20                  25                  30
```

```
Ser Ala Leu Tyr Ser Pro Ser Asp Pro Leu Thr Leu Leu Gln Ala Asp
             35                  40                  45

Thr Val Arg Gly Ala Val Leu Gly Ser Arg Ser Ala Trp Ala Val Glu
 50                  55                  60

Phe Phe Ala Ser Trp Cys Gly His Cys Ile Ala Phe Ala Pro Thr Trp
 65                  70                  75                  80

Lys Ala Leu Ala Glu Asp Val Lys Ala Trp Arg Pro Ala Leu Tyr Leu
                 85                  90                  95

Ala Ala Leu Asp Cys Ala Glu Glu Thr Asn Ser Ala Val Cys Arg Asp
                100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
            130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
            195                 200                 205

Gln His Lys Gly Val Ala Val Arg Arg Val Leu Asn Thr Glu Ala Asn
            210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
            290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
                325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
                405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
            435                 440                 445
```

Cys Arg Asp Cys Ala Ser His Phe Glu Gln Met Ala Ala Ser Met
            450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
                485                 490                 495

Gln Phe Pro Lys Val Gln Trp Pro Arg Glu Leu Cys Ser Ala Cys
            500                 505                 510

His Asn Glu Arg Leu Asp Val Pro Val Trp Asp Val Glu Ala Thr Leu
            515                 520                 525

Asn Phe Leu Lys Ala His Phe Ser Pro Ser Asn Ile Ile Leu Asp Phe
530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
            565                 570                 575

Thr Leu Asp Pro Gly Lys Pro Glu Met Met Lys Ser Pro Thr Asn Thr
            580                 585                 590

Thr Pro His Val Pro Ala Glu Gly Pro Glu Ala Ser Arg Pro Pro Lys
            595                 600                 605

Leu His Pro Gly Leu Arg Ala Ala Pro Gly Gln Glu Pro Pro Glu His
610                 615                 620

Met Ala Glu Leu Gln Arg Asn Glu Gln Glu Gln Pro Leu Gly Gln Trp
625                 630                 635                 640

His Leu Ser Lys Arg Asp Thr Gly Ala Ala Leu Leu Ala Glu Ser Arg
            645                 650                 655

Ala Glu Lys Asn Arg Leu Trp Gly Pro Leu Glu Val Arg Arg Val Gly
            660                 665                 670

Arg Ser Ser Lys Gln Leu Val Asp Ile Pro Glu Gly Gln Leu Glu Ala
            675                 680                 685

Arg Ala Gly Arg Gly Arg Gly Gln Trp Leu Gln Val Leu Gly Gly Gly
690                 695                 700

Phe Ser Tyr Leu Asp Ile Ser Leu Cys Val Gly Leu Tyr Ser Leu Ser
705                 710                 715                 720

Phe Met Gly Leu Leu Ala Met Tyr Thr Tyr Phe Gln Ala Lys Ile Arg
            725                 730                 735

Ala Leu Lys Gly His Ala Gly His Pro Ala Ala
            740                 745

<210> SEQ ID NO 39
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 39
ggtcagtaca tatgtcggcg ctctattcgc cttccg                36

<210> SEQ ID NO 40
<211> LENGTH: 38
<212> TYPE: DNA
<213> ORGANISM: Artificial sequence
<220> FEATURE:
<223> OTHER INFORMATION: Single strand DNA oligonucleotide

```
<400> SEQUENCE: 40
tatgtggatc cttatgcagg gaagtccagg atgatgtt                                    38

<210> SEQ ID NO 41
<211> LENGTH: 613
<212> TYPE: PRT
<213> ORGANISM: Cavia porcellus

<400> SEQUENCE: 41
```

| Met<br>1 | Thr | Gly | Cys | Gly<br>5 | Arg | Arg | Ser | Gly | Trp<br>10 | Leu | Pro | Pro | Leu | Arg<br>15 | Leu |
|---|---|---|---|---|---|---|---|---|---|---|---|---|---|---|---|
| Leu | Leu | Leu | Pro<br>20 | Leu | Leu | Leu | Gly | Gly<br>25 | Pro | Gly | Val | Gly | Ala<br>30 | Ala | Gln |
| Leu | Ala | Ala<br>35 | Leu | Tyr | Ser | Ala | Ser<br>40 | Asp | Pro | Leu | Thr | Leu<br>45 | Leu | Gln | Ala |
| Asp | Thr<br>50 | Val | Arg | Ser | Thr | Val<br>55 | Leu | Asn | Ser | Pro | Ser<br>60 | Ala | Trp | Ala | Val |
| Glu<br>65 | Phe | Phe | Ala | Ser | Trp<br>70 | Cys | Gly | His | Cys | Ile<br>75 | Ala | Phe | Ala | Pro | Thr<br>80 |
| Trp | Lys | Ala | Leu | Ala<br>85 | Lys | Asp | Ile | Lys | Asp<br>90 | Trp | Arg | Pro | Ala | Leu<br>95 | Asn |
| Leu | Ala | Ala | Leu<br>100 | Asn | Cys | Ala | Asp | Glu<br>105 | Thr | Asn | Asn | Ala | Val<br>110 | Cys | Arg |
| Asp | Phe | Asn<br>115 | Ile | Ala | Gly | Phe | Pro<br>120 | Ser | Val | Arg | Phe | Phe<br>125 | Lys | Ala | Phe |
| Ser | Lys<br>130 | Asn | Ser | Thr | Gly | Thr<br>135 | Thr | Leu | Pro | Val | Ala<br>140 | Gly | Ala | Asn | Val |
| Gln<br>145 | Met | Leu | Arg | Glu | Arg<br>150 | Leu | Ile | Asp | Ala | Leu<br>155 | Glu | Ser | His | His | Asp<br>160 |
| Thr | Trp | Pro | Ser | Ala<br>165 | Cys | Pro | Pro | Leu | Glu<br>170 | Pro | Val | Lys | Pro | Lys<br>175 | Glu |
| Ile | Asp | Thr | Phe<br>180 | Phe | Ala | Arg | Asn | Asn<br>185 | Gln | Glu | Tyr | Leu | Val<br>190 | Leu | Ile |
| Phe | Glu | Gln<br>195 | Glu | Asn | Ser | Tyr | Leu<br>200 | Gly | Arg | Glu | Val | Thr<br>205 | Leu | Asp | Leu |
| Ser | Gln<br>210 | His | His | Asp | Leu | Val<br>215 | Val | Arg | Arg | Val | Leu<br>220 | Ser | Thr | Glu | Ala |
| Asn<br>225 | Val | Val | Arg | Lys | Phe<br>230 | Gly | Val | Ala | Asp | Phe<br>235 | Pro | Ser | Cys | Tyr | Leu<br>240 |
| Leu | Phe | Arg | Asn | Gly<br>245 | Ser | Val | Ser | Arg | Val<br>250 | Pro | Val | Leu | Val | Glu<br>255 | Ser |
| Arg | Arg | Phe | Tyr<br>260 | Thr | Ala | Tyr | Leu | Gln<br>265 | Arg | Leu | Ser | Glu | Val<br>270 | Thr | Arg |
| Glu | Gly | Thr<br>275 | Pro | Thr | Pro | Ala | Val<br>280 | Pro | Thr | Ile | Ser | Asp<br>285 | Gln | Ile | Ala |
| Pro | Thr<br>290 | Val | Trp | Lys | Phe | Ala<br>295 | Asp | Arg | Ser | Lys | Ile<br>300 | Tyr | Met | Ala | Asp |
| Leu<br>305 | Glu | Ser | Ala | Leu | His<br>310 | Tyr | Ile | Leu | Arg | Val<br>315 | Glu | Val | Gly | Arg | Phe<br>320 |
| Ser | Val | Leu | Glu | Gly<br>325 | Gln | Arg | Leu | Met | Ala<br>330 | Leu | Lys | Lys | Phe | Val<br>335 | Thr |
| Val | Leu | Thr | Lys<br>340 | Tyr | Phe | Pro | Gly | Gln<br>345 | Pro | Leu | Val | Arg | Asn<br>350 | Phe | Leu |

```
Gln Ser Thr Asn Glu Trp Leu Lys Arg Gln His Lys Lys Lys Met Pro
            355                 360                 365

Tyr Ser Phe Phe Lys Thr Ala Met Asp Ser Arg Asn Glu Glu Ala Val
    370                 375                 380

Ile Thr Lys Glu Val Asn Trp Val Gly Cys Gln Gly Ser Glu Ser His
385                 390                 395                 400

Phe Arg Gly Phe Pro Cys Ser Leu Trp Ile Leu Phe His Phe Leu Thr
                405                 410                 415

Val Gln Ala Ser Gln Lys Asn Ala Glu Ser Ser Gln Lys Pro Ala Asn
            420                 425                 430

Gly Gln Glu Val Leu Gln Ala Ile Arg Asn Tyr Val Arg Phe Phe Phe
            435                 440                 445

Gly Cys Arg Asp Cys Ala Asn His Phe Glu Gln Met Ala Ala Gly Ser
            450                 455                 460

Met His Arg Val Lys Ser Pro Asn Asp Ala Val Leu Trp Leu Trp Thr
465                 470                 475                 480

Ser His Asn Arg Val Asn Ala Arg Leu Ala Gly Ala Pro Ser Glu Asp
                485                 490                 495

Pro Gln Phe Pro Lys Val Gln Trp Pro Pro Glu Leu Cys Ser Ala
            500                 505                 510

Cys His Asn Glu Leu Ser Gly Glu Pro Val Trp Asp Val Asp Ala Thr
            515                 520                 525

Leu Arg Phe Leu Lys Thr His Phe Ser Pro Ser Asn Ile Val Leu Asn
            530                 535                 540

Phe Pro Pro Ala Glu Pro Ala Ser Arg Ser Ser Val His Ser Trp Gly
545                 550                 555                 560

Ala Thr Pro His Leu Glu Leu Asp Ala Leu Gly Leu Val Thr Arg Asn
            565                 570                 575

Ser Ala Leu Ala Leu Glu Arg Ala Glu Ile Ser Glu Ser Pro Gly Ser
            580                 585                 590

Asn Ala Met Pro Asn Ile Pro Ala Glu Arg Pro Glu Leu Phe Glu Ala
595                 600                 605

Leu Ser His Ser Arg
610

<210> SEQ ID NO 42
<211> LENGTH: 750
<212> TYPE: PRT
<213> ORGANISM: Rattus norvegicus

<400> SEQUENCE: 42

Met Arg Arg Cys Gly Arg His Ser Gly Pro Pro Ser Leu Leu Leu Leu
1                5                  10                 15

Leu Leu Leu Pro Pro Leu Leu Leu Ser Val Pro Gly Ala Tyr Ala
            20                  25                 30

Ala Arg Leu Ser Val Leu Tyr Ser Ser Asp Pro Leu Thr Leu Leu
        35                  40                  45

Asp Ala Asp Thr Val Arg Pro Ala Val Leu Gly Ser Ser Ala Trp
    50                  55                  60

Ala Val Glu Phe Phe Ala Ser Trp Cys Gly His Cys Ile Ala Phe Ala
65                  70                  75                  80

Pro Thr Trp Lys Glu Leu Ala Asn Asp Val Lys Asp Trp Arg Pro Ala
                85                  90                  95

Leu Asn Leu Ala Val Leu Asp Cys Ala Asp Glu Thr Asn Ser Ala Val
                100                 105                 110
```

-continued

```
Cys Arg Glu Phe Asn Ile Ala Gly Phe Pro Thr Val Arg Phe Phe Lys
            115                 120                 125
Ala Phe Ser Lys Asn Gly Thr Gly Thr Ala Leu Pro Ala Ala Gly Ala
130                 135                 140
Asn Val Gln Thr Leu Arg Met Arg Leu Ile Asp Ala Leu Glu Ser His
145                 150                 155                 160
Arg Asp Thr Trp Pro Pro Ala Cys Pro Pro Leu Glu Pro Ala Lys Leu
                165                 170                 175
Lys Asp Ile Asn Glu Phe Phe Thr Arg Ser Lys Ala Glu Tyr Leu Ala
            180                 185                 190
Leu Ile Phe Glu Arg Glu Asp Ser Tyr Leu Gly Arg Glu Val Thr Leu
        195                 200                 205
Asp Leu Ser Gln Phe His Ala Val Ala Val Arg Arg Val Leu Asn Ser
210                 215                 220
Glu Ser Asp Val Val Ser Lys Phe Ala Val Thr Asp Phe Pro Ser Cys
225                 230                 235                 240
Tyr Leu Leu Leu Arg Asn Gly Ser Val Ser Arg Val Pro Val Leu Val
                245                 250                 255
Glu Ser Arg Pro Phe Tyr Thr Ser Tyr Leu Arg Gly Leu Pro Gly Leu
            260                 265                 270
Thr Arg Glu Ala Pro Pro Thr Thr Ala Ala Pro Val Thr Pro Asp Lys
        275                 280                 285
Ile Ala Pro Thr Val Trp Lys Phe Ala Asp Arg Ser Lys Ile Tyr Met
290                 295                 300
Ala Asp Leu Glu Ser Ala Leu His Tyr Ile Leu Arg Val Glu Val Gly
305                 310                 315                 320
Lys Phe Ser Val Leu Glu Gly Gln Arg Leu Val Ala Leu Lys Lys Phe
                325                 330                 335
Val Ala Val Leu Ala Lys Tyr Phe Pro Gly Gln Pro Leu Val Gln Asn
            340                 345                 350
Phe Leu His Ser Ile Asn Asp Trp Leu Gln Lys Gln Lys Lys Lys
        355                 360                 365
Ile Pro Tyr Ser Tyr Phe Lys Ala Ala Leu Asp Ser Arg Lys Glu Asn
    370                 375                 380
Ala Val Leu Ala Glu Lys Val Asn Trp Ile Gly Cys Gln Gly Ser Glu
385                 390                 395                 400
Pro His Phe Arg Gly Phe Pro Cys Ser Leu Trp Val Leu Phe His Phe
                405                 410                 415
Leu Thr Val Gln Ala His Arg Tyr Ser Glu Ala His Pro Gln Glu Pro
            420                 425                 430
Ala Asp Gly Gln Glu Val Leu Gln Ala Met Arg Ser Tyr Val Gln Ser
        435                 440                 445
Phe Phe Gly Cys Arg Asp Cys Ala Asn His Phe Glu Gln Met Ala Ala
450                 455                 460
Ala Ser Met His Gln Val Lys Ser Pro Ser Asn Ala Val Leu Trp Leu
465                 470                 475                 480
Trp Thr Ser His Asn Arg Val Asn Ala Arg Leu Ser Gly Ala Leu Ser
                485                 490                 495
Glu Asp Pro Gln Phe Pro Lys Val Gln Trp Pro Pro Arg Glu Leu Cys
            500                 505                 510
Ser Ala Cys His Asn Glu Val Asn Gly Gln Val Pro Leu Trp Asp Leu
        515                 520                 525
```

```
Gly Ala Thr Leu Asn Phe Leu Lys Ala His Phe Ser Pro Ala Asn Ile
            530                 535                 540

Val Arg Asp Pro Pro Ala Pro Gly Pro Ala Ser Arg Arg Gly Thr Gln
545                 550                 555                 560

Asp Pro Glu Ala Ser Pro Asn Leu Val Met Asp Thr Leu Lys Leu Glu
                565                 570                 575

Thr Gly Asn Ser Val Leu Gly His Glu Gln Ala Ser Ala Ala Ser
            580                 585                 590

Pro Gly Ala Thr Ala Leu Asp Val Pro Ala Gly Lys Pro Glu Ala Ser
            595                 600                 605

Gly Pro Gln Glu Leu Asn Ala Gly Leu Ser Met Gly Gly Ala Ser Pro
            610                 615                 620

Gly Gln Gly Pro Pro Glu His Thr Glu Glu Leu Leu Arg Asp Val Gln
625                 630                 635                 640

Glu Asn Ala Gln Gly Gln His Leu Ser Lys Arg Asp Thr Glu Ala
                645                 650                 655

Leu Leu Leu Pro Glu Val Asn His Leu Gln Gly Pro Leu Ala Pro Arg
            660                 665                 670

Arg Gly Gly His Ser Pro Lys Gln Leu Ala Ser Ile Leu Glu Gly Glu
            675                 680                 685

Pro Glu Ala Leu Ala Ile Gln Gly Arg Arg Gln Trp Leu Gln Val Leu
            690                 695                 700

Gly Gly Gly Val Ser Phe Leu Asp Ile Ser Leu Cys Val Gly Leu Tyr
705                 710                 715                 720

Ser Val Ser Phe Met Gly Leu Leu Ala Met Tyr Thr Tyr Phe Arg Ala
                725                 730                 735

Arg Met Arg Thr Pro Lys Gly His Val Ser Tyr Pro Thr Ala
            740                 745                 750

<210> SEQ ID NO 43
<211> LENGTH: 748
<212> TYPE: PRT
<213> ORGANISM: Mus musculus

<400> SEQUENCE: 43

Met Arg Arg Cys Gly Arg Leu Ser Gly Pro Pro Ser Leu Leu Leu Leu
1               5                   10                  15

Leu Leu Leu Leu Ser Pro Leu Leu Phe Ser Gly Pro Gly Ala Tyr Ala
            20                  25                  30

Ala Arg Leu Ser Val Leu Tyr Ser Ser Ser Asp Pro Leu Thr Leu Leu
            35                  40                  45

Asp Ala Asp Ser Val Arg Pro Thr Val Leu Gly Ser Ser Ser Ala Trp
50                  55                  60

Ala Val Glu Phe Phe Ala Ser Trp Cys Gly His Cys Ile Ala Phe Ala
65                  70                  75                  80

Pro Thr Trp Lys Glu Leu Ala Asn Asp Val Lys Asp Trp Arg Pro Ala
                85                  90                  95

Leu Asn Leu Ala Val Leu Asp Cys Ala Glu Glu Thr Asn Ser Ala Val
            100                 105                 110

Cys Arg Glu Phe Asn Ile Ala Gly Phe Pro Thr Val Arg Phe Phe Gln
            115                 120                 125

Ala Phe Thr Lys Asn Gly Ser Gly Ala Thr Leu Pro Gly Ala Gly Ala
            130                 135                 140

Asn Val Gln Thr Leu Arg Met Arg Leu Ile Asp Ala Leu Glu Ser His
145                 150                 155                 160
```

-continued

```
Arg Asp Thr Trp Pro Pro Ala Cys Pro Pro Leu Glu Pro Ala Lys Leu
                165                 170                 175
Asn Asp Ile Asp Gly Phe Phe Thr Arg Asn Lys Ala Asp Tyr Leu Ala
            180                 185                 190
Leu Val Phe Glu Arg Glu Asp Ser Tyr Leu Gly Arg Glu Val Thr Leu
        195                 200                 205
Asp Leu Ser Gln Tyr His Ala Val Ala Val Arg Arg Val Leu Asn Thr
    210                 215                 220
Glu Ser Asp Leu Val Asn Lys Phe Gly Val Thr Asp Phe Pro Ser Cys
225                 230                 235                 240
Tyr Leu Leu Arg Asn Gly Ser Val Ser Arg Val Pro Val Leu Val
                245                 250                 255
Glu Ser Arg Ser Phe Tyr Thr Ser Tyr Leu Arg Gly Leu Pro Gly Leu
                260                 265                 270
Thr Arg Asp Ala Pro Pro Thr Thr Ala Thr Pro Val Thr Ala Asp Lys
                275                 280                 285
Ile Ala Pro Thr Val Trp Lys Phe Ala Asp Arg Ser Lys Ile Tyr Met
            290                 295                 300
Ala Asp Leu Glu Ser Ala Leu His Tyr Ile Leu Arg Val Glu Val Gly
305                 310                 315                 320
Lys Phe Ser Val Leu Glu Gly Gln Arg Leu Val Ala Leu Lys Lys Phe
                325                 330                 335
Val Ala Val Leu Ala Lys Tyr Phe Pro Gly Gln Pro Leu Val Gln Asn
                340                 345                 350
Phe Leu His Ser Ile Asn Asp Trp Leu Gln Lys Gln Lys Lys Arg
            355                 360                 365
Ile Pro Tyr Ser Phe Phe Lys Ala Ala Leu Asp Ser Arg Lys Glu Asp
            370                 375                 380
Ala Val Leu Thr Glu Lys Val Asn Trp Val Gly Cys Gln Gly Ser Glu
385                 390                 395                 400
Pro His Phe Arg Gly Phe Pro Cys Ser Leu Trp Val Leu Phe His Phe
                405                 410                 415
Leu Thr Val Gln Ala Asn Arg Tyr Ser Glu Ala His Pro Gln Glu Pro
            420                 425                 430
Ala Asp Gly Gln Glu Val Leu Gln Ala Met Arg Ser Tyr Val Gln Phe
            435                 440                 445
Phe Phe Gly Cys Arg Asp Cys Ala Asp His Phe Glu Gln Met Ala Ala
            450                 455                 460
Ala Ser Met His Gln Val Arg Ser Pro Ser Asn Ala Ile Leu Trp Leu
465                 470                 475                 480
Trp Thr Ser His Asn Arg Val Asn Ala Arg Leu Ser Gly Ala Leu Ser
                485                 490                 495
Glu Asp Pro His Phe Pro Lys Val Gln Trp Pro Pro Arg Glu Leu Cys
                500                 505                 510
Ser Ala Cys His Asn Glu Leu Asn Gly Gln Val Pro Leu Trp Asp Leu
            515                 520                 525
Gly Ala Thr Leu Asn Phe Leu Lys Ala His Phe Ser Pro Ala Asn Ile
            530                 535                 540
Val Ile Asp Ser Ser Ala Ser Arg His Thr Gly Arg Arg Gly Ser Pro
545                 550                 555                 560
Glu Ala Thr Pro Glu Leu Val Met Asp Thr Leu Lys Leu Glu Ser Arg
                565                 570                 575
```

```
Asn Ser Val Leu Gly His Glu Gln Ala Ala Ser Ala Glu Ser Pro Gly
            580                 585                 590

Ala Thr Ala Leu Asp Val Pro Ala Glu Lys Pro Glu Ala Ser Gly Pro
        595                 600                 605

Gln Glu Leu Tyr Thr Gly Leu Arg Met Gly Gly Ala Ser Pro Gly Gln
        610                 615                 620

Gly Pro Pro Glu Arg Met Glu Asp His Gln Arg Asp Met Gln Glu Asn
625                 630                 635                 640

Ala Pro Gly Gln Gln His Leu Ser Lys Arg Asp Thr Glu Ala Leu Phe
                645                 650                 655

Leu Pro Glu Val Asn His Leu Gln Gly Pro Leu Glu Leu Arg Arg Gly
            660                 665                 670

Gly Arg Ser Pro Lys Gln Leu Ala Pro Ile Leu Glu Glu Glu Pro Glu
        675                 680                 685

Ala Leu Ala Ile Gln Gly Gln Gly Gln Trp Leu Gln Val Leu Gly Gly
        690                 695                 700

Gly Ile Ser His Leu Asp Ile Ser Leu Cys Val Gly Leu Tyr Ser Val
705                 710                 715                 720

Ser Phe Met Gly Leu Leu Ala Met Tyr Thr Tyr Phe Arg Ala Arg Leu
            725                 730                 735

Arg Thr Pro Lys Gly His Ala Ser Tyr Pro Thr Ala
            740                 745
```

COMPOSITIONS FOR INHIBITION OF QUIESCIN SULFHYDRYL OXIDASE (QSOX1) AND USES OF SAME

RELATED APPLICATIONS

This application is a National Phase of PCT Patent Application No. PCT/IL2013/050209 having International filing date of Mar. 7, 2013, which claims the benefit of priority under 35 USC §119(e) of U.S. Provisional Patent Application No. 61/665,365 filed on Jun. 28, 2012 and 61/607,696 filed on Mar. 7, 2012. The contents of the above applications are all incorporated by reference as if fully set forth herein in their entirety.

FIELD AND BACKGROUND OF THE INVENTION

Sequence Listing Statement

The ASCII file, entitled 60175SequenceListing.txt, created on Aug. 11, 2014, comprising 85,987 bytes, submitted concurrently with the filing of this application is incorporated herein by reference.

The present invention, in some embodiments thereof, relates to QSOX1 inhibiting agents and, more particularly, but not exclusively, to the use of same for treating laminin-related diseases.

Quiescin sulfhydryl oxidase 1 (QSOX1) is an enzyme that uses a bound flavin adenine dinucleotide (FAD) co-factor to mediate transfer of electrons from pairs of thiol groups in substrate proteins to molecular oxygen, generating hydrogen peroxide as a byproduct. QSOX1 shares this fundamental catalytic activity of disulfide formation with a number of other enzymes that function in early-stage protein folding in the endoplasmic reticulum (ER) and with enzymes that mediate folding and retention of proteins in the mitochondrial intermembrane space. However, QSOX1 is the only disulfide catalyst known to be localized primarily to organelles downstream of the ER in the secretory pathway and to undergo regulated secretion from cells. QSOX1 is a multi-domain protein that undergoes a series of dithiol/disulfide exchange steps to pass electrons from substrate thiols to its FAD cofactor. The two main redox-active domains of the enzyme, the first of which interacts with the protein thiol-containing substrate and the second of which catalyzes reduction of molecular oxygen, must change their relative orientations during the reaction cycle. In particular, the redox-active di-cysteine motif in the amino-terminal, thioredoxin-fold (Trx) domain (FIGS. 1A-B) must be sufficiently solvent-exposed to accept electrons from substrate proteins. The Trx domain must then bury itself against the redox-active di-cysteine motif of the disulfide-generating ERV-fold (Erv) domain to transfer the electrons further (FIGS. 1A-B). A set of crystal structures of QSOXs from mammals and from a trypanosomal parasite illustrated the nature of the conformational changes exhibited by QSOX enzymes and identified the flexible linker that permits such rearrangements.

QSOX1 was initially discovered as a catalyst of disulfide bond formation in milk and mammalian seminal vesicle secretions [Janolino V. G. and Swaisgood H. E. (1975) J. Biol. Chem. 250, 2532-2538]. The QSOX1 transcript was later identified via its induction in cultured lung fibroblasts as they reached confluence and entered the quiescent state [Coppock D. L. et al. (1993) Cell Growth Differ. 4, 483-493]. QSOX1 expression has been observed in vivo during embryonic development [Portes K. F. et al. (2008) J. Mol. Histol. 39, 217-225] as well as in many adult organs and tissue types. QSOX1 levels are particularly high in organs with high secretory capacity such as lung, ovary, and endometrium [Musard J. F. et al. (2001) Biochem. Biophys. Res. Comm 287, 83-91], and in the superficial epithelial layer of the stomach, bronchioli, salivary glands, esophagus, islets of Langherans, urinary bladder, and both the male and female reproductive systems [Tury A. et al. (2006) Cell Tissue Res. 323, 91-103]. QSOX1 also shows a spatially and temporally complex expression pattern in the developing brain [Amiot C. et al., (2004) Brain Res. Mol. Brain Res. 125, 13-21]. QSOX1 produced by quiescent fibroblasts was shown to be secreted [Coppock D. et al., (2000) Biochem. Biophys. Res. Comm 269, 604-610], and sulfhydryl oxidase activity in various body fluids suggests QSOX1 secretion from other cell types as well [Janolino V. G. and Swaisgood, supra].

The purpose of an extracellular or late-secretory disulfide catalyst has remained a major open question, and native substrates of QSOX1 have yet to be identified.

Recently several researchers have linked between QSOX1 and cancer.

According to the teachings of Antwi et al. [Antwi K. et al. (2009) J. Proteome Res. 8, 4722-4731], increased QSOX1 protein levels were seen in ductal adenocarcinomas of the pancreas (DAP) and associated micrometastases in human patients. Furthermore, mass spectrometric studies of the serum peptidome of DAP patients revealed high levels of a peptide derived, apparently proteolytically, from QSOX1 [Antwi et al. (2009), supra]. Katchman et al. teach that QSOX1 promotes invasion of pancreatic tumor cells mediated by matrix metalloproteinases [Katchman et al. (2011) Mol Cancer Res; 9(12) 1621-31]. Moreover, in a mouse model for prostate cancer, loss of function of the Nkx3.1 tumor suppressor resulted in increased production of QSOX1 [Ouyang X. et al. (2005) Cancer Res. 65, 6773-6779]. QSOX1 was particularly highly expressed in prostatic hyperplasia and interepithelial neoplasia, early events in prostate tumorigenesis [Song H. et al. (2009) Oncogene 28, 3307-3319].

Additional background art includes PCT Application Nos. WO 2010/077921 and WO 2010/071787.

SUMMARY OF THE INVENTION

According to an aspect of some embodiments of the present invention there is provided a method of inhibiting or preventing laminin assembly in a basement membrane, the method comprising contacting a tissue with an agent which inhibits QSOX1 activity or expression, thereby inhibiting or preventing laminin assembly in the basement membrane.

According to an aspect of some embodiments of the present invention there is provided a method of inhibiting cell migration via a laminin-comprising basement membrane, the method comprising contacting a tissue with an agent which inhibits QSOX1 activity or expression, thereby inhibiting the cell migration via the laminin-comprising basement membrane.

According to an aspect of some embodiments of the present invention there is provided a method of treating a laminin-associated disease or condition in a subject in need thereof the method comprising administering to the subject a therapeutically effective amount of an agent which inhibits QSOX1 activity or expression, thereby treating the laminin-associated disease or condition in the subject.

According to an aspect of some embodiments of the present invention there is provided a use of a therapeutically effective amount of an agent which inhibits QSOX1 activity or expression for the manufacture of a medicament identified for treating a laminin-associated disease or condition in a subject in need thereof.

According to an aspect of some embodiments of the present invention there is provided an isolated antibody comprising an antigen recognition domain which specifically binds QSOX1 and inhibits a QSOX1 activity in mediating basement membrane assembly that supports cell migration.

According to an aspect of some embodiments of the present invention there is provided a pharmaceutical composition comprising as an active ingredient the isolated antibody of the present invention and a pharmaceutically acceptable carrier.

According to an aspect of some embodiments of the present invention there is provided an isolated polynucleotide encoding the antibody of the present invention.

According to an aspect of some embodiments of the present invention there is provided an isolated polynucleotide comprising a nucleic acid sequence encoding a complementarity determining region (CDR) containing polypeptide having the CDRs set forth in SEQ ID NOs: 29-34.

According to an aspect of some embodiments of the present invention there is provided a method of diagnosing a laminin-associated disease or condition in a subject comprising: (a) contacting a biological sample of the subject with the isolated polypeptide of the present invention under conditions suitable for immunocomplex formation between the isolated polypeptide and QSOX1 proteins; and (b) detecting formation of the immunocomplex, wherein a presence of the immunocomplex above a predetermined threshold is indicative of the laminin-associated disease thereby diagnosing the laminin-associated disease or condition in the subject.

According to an aspect of some embodiments of the present invention there is provided a kit for detecting a level of QSOX1 in a biological sample comprising the antibody of the present invention.

According to an aspect of some embodiments of the present invention there is provided a method of identifying a QSOX1 inhibitor, the method comprising culturing a tissue in the presence or absence of a test agent, wherein a decrease in functional basement membrane following the culturing with the test agent is indicative that the test agent is the QSOX1 inhibitor.

According to an aspect of some embodiments of the present invention there is provided an isolated polypeptide comprising an amino acid sequence of QSOX1, the peptide being less than 500 amino acids in length.

According to an aspect of some embodiments of the present invention there is provided an isolated polypeptide comprising an amino acid sequence of QSOX1 as set forth in SEQ ID NO: 6.

According to an aspect of some embodiments of the present invention there is provided a method for preventing or treating a laminin-associated disease or condition in a subject in need thereof, the method comprising administering to the subject a therapeutically effective amount of the pharmaceutical composition.

According to an aspect of some embodiments of the present invention there is provided a use of the isolated antibody for the manufacture of a medicament identified for preventing or treating a laminin-associated disease or condition in a subject in need thereof.

According to an aspect of some embodiments of the present invention there is provided an article of manufacture comprising the isolated antibody being packaged in a packaging material and identified in print, in or on the packaging material for use in the treatment of a laminin-associated disease or condition.

According to an aspect of some embodiments of the present invention there is provided a method of producing an antibody which comprises an antigen recognition domain which specifically binds QSOX1 and inhibits a QSOX1 activity in mediating basement membrane assembly that supports cell migration, the method comprising: (a) immunizing a mouse with a recombinant QSOX1 polypeptide; (b) generating hybridomas from spleen cells of the mouse of step (a) comprising fusing the spleen cells with myeloma cells; and (c) selecting positive hybridomas, thereby producing the antibody which comprises the antigen recognition domain which specifically binds the QSOX1.

According to some embodiments of the invention, the cell is a tumor cell.

According to some embodiments of the invention, the tissue is a tumor tissue.

According to some embodiments of the invention, the tissue comprises fibroblasts.

According to some embodiments of the invention, the method is performed in-vivo.

According to some embodiments of the invention, the laminin-associated disease or condition is a tumor.

According to some embodiments of the invention, the tumor is a metastasizing solid tumor.

According to some embodiments of the invention, the tumor is an adenocarcinoma.

According to some embodiments of the invention, the tumor is selected from the group consisting of a prostate cancer, a lung cancer, a breast cancer, a cervical cancer, an urachus cancer, a vaginal cancer, a colon cancer, an esophagus cancer, a pancreatic cancer, a throat cancer, a stomach cancer and a myeloid leukemia.

According to some embodiments of the invention, the laminin-associated disease or condition is associated with fibrosis.

According to some embodiments of the invention, the laminin comprises an alpha 4 chain.

According to some embodiments of the invention, the laminin is laminin-411 or laminin-421.

According to some embodiments of the invention, the agent is a polypeptide agent.

According to some embodiments of the invention, the polypeptide agent is selected from the group consisting of an antibody, an antibody fragment or a peptide.

According to some embodiments of the invention, the polypeptide agent is directed towards amino acid coordinates 34 to 266 of the QSOX1.

According to some embodiments of the invention, the antibody is MAb492.1 and comprises complementarity determining regions (CDRs) SEQ ID NOs: 29-34.

According to some embodiments of the invention, the antibody fragment is scFV492.1 and comprises complementarity determining regions (CDRs) SEQ ID NOs: 29-34.

According to some embodiments of the invention, the agent is a polynucleotide agent.

According to some embodiments of the invention, the polynucleotide agent is selected from the group consisting of an antisense, a siRNA, a microRNA, a Ribozyme and a DNAzyme.

According to some embodiments of the invention, the activity is assayed by at least one of an immunofluorescence (IF) staining assay of the extracellular matrix or Western blot assay detecting for soluble laminin.

According to some embodiments of the invention, the antibody is an antibody fragment.

According to some embodiments of the invention, the antibody is selected from the group consisting of a Fab fragment, an Fv fragment, a single chain antibody and a single domain antibody.

According to some embodiments of the invention, the antibody is a monoclonal antibody.

According to some embodiments of the invention, the monoclonal antibody is MAb492.1 and comprises complementarity determining regions (CDRs) SEQ ID NOs: 29-34.

According to some embodiments of the invention, the antibody is a single chain antibody.

According to some embodiments of the invention, the single chain antibody is scFV492.1 and comprises complementarity determining regions (CDRs) SEQ ID NOs: 29-34.

According to some embodiments of the invention, the antibody or antibody fragment is humanized.

According to some embodiments of the invention, the antibody is a chimeric antibody.

According to some embodiments of the invention, the antibody is immobilized to a solid support.

According to some embodiments of the invention, the antibody is attached to a detectable moiety.

According to some embodiments of the invention, the isolated antibody comprising an amino acid sequence as set forth in SEQ ID NOs: 7 and 8.

According to some embodiments of the invention, the isolated antibody comprising an amino acid sequence as set forth in SEQ ID NOs: 27 and 28.

According to some embodiments of the invention, the decrease in functional basement membrane comprises a decrease in laminin assembly in the basement membrane.

According to some embodiments of the invention, the decrease in laminin assembly comprises an increase in soluble laminin in the tissue.

According to some embodiments of the invention, the tissue comprises a tissue culture.

According to some embodiments of the invention, the method is performed in vivo.

According to some embodiments of the invention, the method further comprising a decrease in QSOX1 activity or expression level.

According to some embodiments of the invention, the QSOX1 is a human QSOX1.

According to some embodiments of the invention, the QSOX1 is a murine QSOX1.

According to some embodiments of the invention, the laminin-associated disease or condition is a tumor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B are schematic illustrations depicting domain organization and reaction cycle of HsQSOX1. FIG. 1A is a schematic diagram illustrating the four domains of HsQSOX1. The amino-terminal fragment, $HsQSOX1_{Trx}$, is composed of two Trx-fold domains. The carboxy-terminal fragment, $HsQSOX1_{Erv}$, is composed of two Erv-fold domains. The degenerate Erv-like sulfhydryl oxidase module that has lost its active-site cysteines and cofactor binding capability is designated as "ψErv". Yellow balls represent the CXXC motifs (redox-active disulfides). The three fused hexagons indicate the flavin adenine dinucleotide (FAD) cofactor, bound by the Erv domain; and FIG. 1B illustrates the steps in the reaction cycle of substrate oxidation and oxygen reduction by HsQSOX1. Domains are represented with the same names and colors as in A, with a gray line representing the linker between the Trx2 domain and the ψErv domain. Fused yellow balls represent disulfide bonds. Separated yellow balls indicate reduced cysteines.

FIGS. 1C-M depict that QSOX1 is Golgi-localized in sub-confluent fibroblasts and secreted by confluent fibroblasts. FIGS. 1C-J are photographs illustrating sub-confluent WI-38 fibroblasts immunostained with either a Golgi-specific (p115) or an ER-specific (GRASP65) antibody (red) and QSOX1 (green). DAPI staining (blue) indicates nuclei. Scale bar is 10 µm; FIG. 1K is a photograph illustrating a western blot of confluent WI-38 cell extracts (top) and RT-PCR (bottom) demonstrating expression of QSOX1 but not QSOX2 in these cells; FIG. 1L is a photograph illustrating a western blot of WI-38 culture supernatants (top) and RT-PCR (bottom) of cells as a function of confluence; and FIG. 1M is a bar graph illustrating sulfhydryl oxidase activity of cell culture supernatants measured by oxygen consumption upon addition of 5 mM DTT.

Figure 2H:
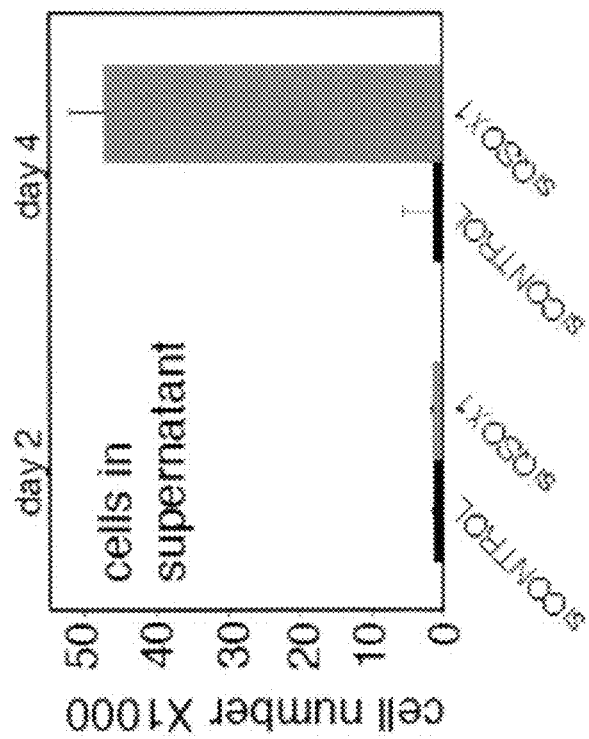
Figure 2G:
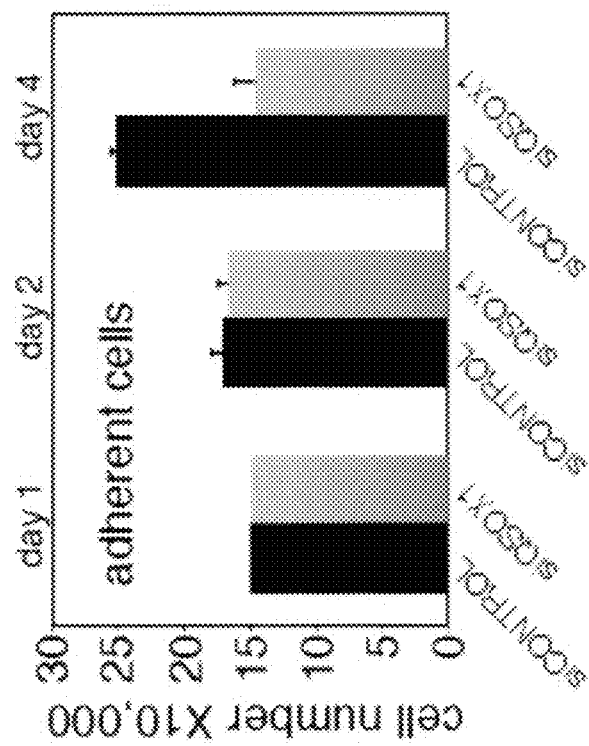

FIGS. 2A-H depict that active QSOX1 is required to form a dense fibroblast monolayer in culture. FIGS. 2A-D are photographs illustrating DAPI staining of WI-38 culture monolayers four days following transfection with control (siCONTROL) or QSOX1-specific (siQSOX1) siRNA. FIGS. 2C-D depict cultures treated with siQSOX1 which were supplemented with 50 nM recombinant QSOX1 (rQSOX1) or an inactive mutant (rQSOX1-AA) 24 hours after siRNA transfection. Scale bar is 10 µm; FIG. 2E is a bar graph illustrating quantification of cell numbers from fields as shown in FIGS. 2A-D; FIG. 2F is a schematic illustration of a diagram of domain organization and structure of QSOX1 with redox-active disulfides shown as paired yellow balls labeled "CXXC." The flavin adenine dinucleotide (FAD) cofactor is indicated by fused hexagons (above) or orange sticks (below). The jagged vertical line represents an alternative splicing event that generates either a soluble or a membrane-bound version of QSOX1. "TM" stands for transmembrane region. Recombinant QSOX1 spans all QSOX1 domains and redox-active sites. The rQSOX1-AA mutant lacks the amino-terminal redox-active cysteines and FIGS. 2G-H are bar graphs illustrating that QSOX1 knockdown causes cell detachment from the tissue culture plate.

FIG. 2G shows cell numbers, on control and QSOX1-knockdown plates, as reported for days 1, 2, and 4 following siRNA transfection. FIG. 2H displays the number of cells found detached and floating, but viable as indicated by trypan blue staining in culture supernatants.

FIGS. 3A-R are photographs depicting that QSOX1 is required for laminin incorporation into the basement membrane. FIGS. 3A-L illustrate laminin immunostaining using P1 polyclonal antibodies revealing a more substantial laminin matrix in control (siCONTROL, FIGS. 3A-C) compared to QSOX1-knockdown (siQSOX1, FIGS. 3D-F) WI-38 cultures. Supplementation of siQSOX1 cultures with recombinant QSOX1 (rQSOX1, FIGS. 3G-I), but not the rQSOX1-AA mutant (FIGS. 3J-L), 24 hours following siRNA transfection restores the thick laminin matrix. Scale bar is 10 µm; and FIGS. 3M-R illustrate immunostaining of control knockdown and siQSOX1-treated cell monolayers with laminin chain-specific antibodies. LAMA2 and LAMA4 indicate staining with antibodies recognizing the laminin $\alpha 2$ and $\alpha 4$ chains, respectively. Scale bar is 10 µm.

FIGS. 4A-C depict that QSOX1 is required for laminin incorporation into the basement membrane. FIG. 4A is a bar graph depicting quantification of laminin intensity from fields such as shown in FIGS. 3A-L. FIG. 4B is a photograph illustrating a western blot of laminin (upper panel) and QSOX1 (lower panel) in WI-38 cell culture supernatant samples. Lanes 1-2 correspond to supernatants from cells treated with control siRNA. Lanes 3-5 correspond to supernatants from cells treated with QSOX1-specific siRNA; and FIG. 4C is a bar graph depicting quantification of laminin chain intensity from fields such as shown in FIGS. 3M-R.

FIGS. 5A-F are photographs depicting that QSOX1 is required for laminin incorporation into the basement membrane. SEM images of WI-38 surfaces reveal a distinct clustered material, indicated by arrows in images taken at lower magnification. This material, presumed to be laminin containing the $\alpha 4$ chain, appeared only on cells treated with control siRNA and not on cells treated with siQSOX1.

Figure 5G:
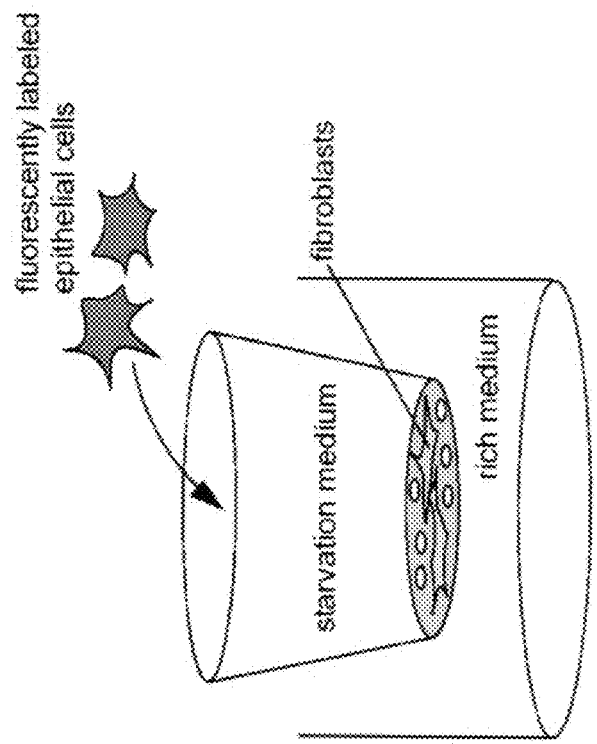
Figure 6R:
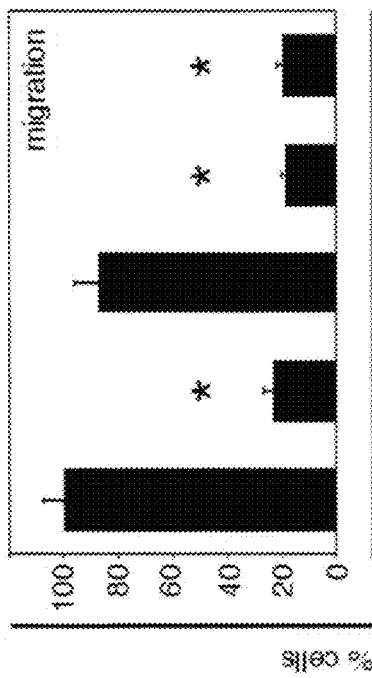

FIG. 5G is a schematic diagram of the migration assay used for FIGS. 6A-R. Fibroblasts were grown to confluence in the upper chamber before addition of fluorescently labeled tumor cells. Tumor cells that had penetrated the fibroblast/ECM layer, migrated through the porous membrane, and reached the bottom surface of the upper chamber were counted.

FIGS. 6A-Q depict that QSOX1 produced by fibroblasts promotes tumor epithelial cell adhesion and migration. FIGS. 6A-O are photographs depicting fluorescently labeled H460 human lung cancer cells that have migrated through a pre-formed stromal layer of WI-38 fibroblasts subjected to the indicated treatments. Recombinant enzymes (rQSOX1, FIGS. 6G-I, and rQSOX1-AA, FIGS. 6J-L) were added 24 hours following siRNA transfection of the fibroblasts (as in FIGS. 2A-H, 3A-R, 4A-C and 5A-F). For FIGS. 6M-O, labeled "anti-$\alpha 6$," the H460 cells were treated with antibodies against the $\alpha 6$ integrin subunit that block integrin activity prior to layering onto control transfected fibroblasts. Three representative fields are shown for each treatment; FIG. 6P is a bar graph depicting quantification of migratory cell numbers from panels such as shown in FIGS. 6A-O; and FIG. 6Q is a bar graph indicating the number of cells, in each of the samples, remaining adherent after subjection to force.

Figure 6S:
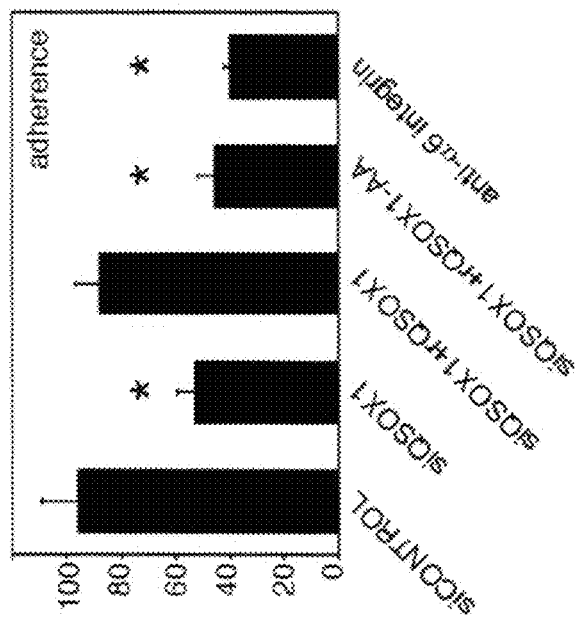

FIGS. 6R-S depict quantification of fluorescently labeled BxPC-3 pancreatic cancer cells that migrated through a pre-formed stromal layer of pancreatic fibroblasts (FIG. 6R), and H460 lung cancer cells remaining adherent to a lung fibroblast layer after subjection to force (FIG. 6S), shown as a percent of control (siCONTROL) values.

Figure 6T:
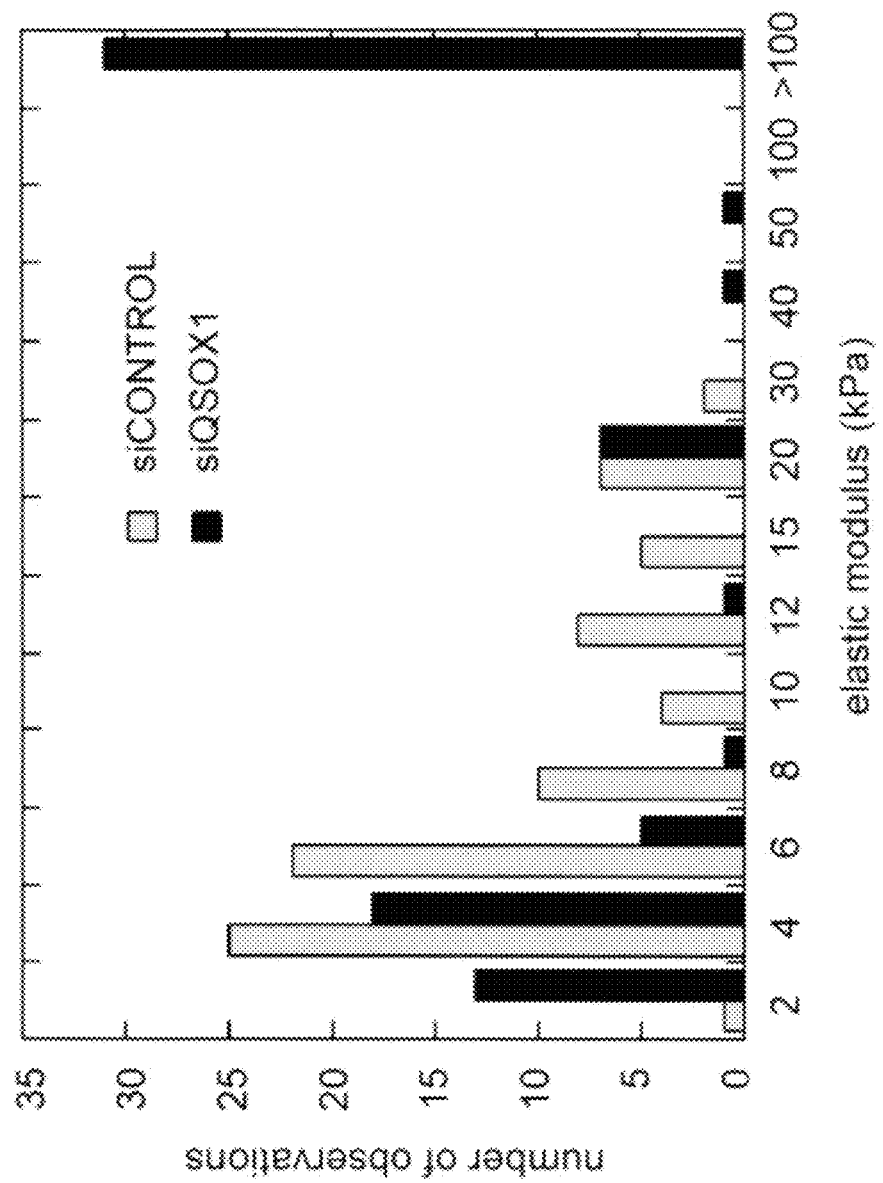

FIG. 6T depicts atomic force microscopy showing that control fibroblast cultures are stiffer than those produced in the absence of QSOX1. The mechanical properties of fibroblast cultures and associated ECM were altered as a result of QSOX1 depletion. Atomic force microscopy was used to measure the stiffness of confluent control or QSOX1-depleted WI-38 fibroblasts. Measured with a tip size and indentation depth chosen to optimize sensitivity to alterations in ECM, the distribution of elastic moduli for control fibroblast cultures peaked between 4 to 6 kPa, but a broad range of values up to 30 kPa were observed. This range of elastic moduli is consistent with a previous AFM study of cultured fibroblasts. The distribution for QSOX1-knockdown cultures showed a peak at lower stiffness values, 2 to 4 kPa, with a few scattered measurements between 8 kPa and 50 kPa. The substantial set of indentation curves yielding elastic moduli greater than 100 kPa obtained for QSOX1-knockdown but not for control cell cultures probably represents direct contact with the underlying petri dish support.

FIGS. 7A-D depict that QSOX1 is up-regulated in fibroblasts associated with tumors. FIG. 7A is a western blot of QSOX1 in supernatants of WI-38 cells cultured for two days in the absence or presence of conditioned media (C.M.) from H460 lung carcinoma cells; FIG. 7B is a bar graph depicting that cancer-associated fibroblast (CAF) cells cultured ex vivo show higher levels of QSOX1 compared to fibroblasts taken from tissue more distant from tumor growths (NF=normal fibroblasts). When exposed to conditioned media from H460 tumor cell cultures, NFs are induced to transcribe and secrete comparable levels of QSOX1 as produced by CAFs; and FIGS. 7C-D illustrate histological sections of breast ductal carcinoma stained with anti-QSOX1. Arrows indicate representative tumor-associated fibroblasts expressing high levels of QSOX1. The arrowhead indicates a fibroblast cell negative for QSOX1.

FIGS. 8A-K depict that inhibition of QSOX1 blocks tumor epithelial cell migration. FIGS. 8A-F are photographs illustrating fluorescently labeled H460 human lung cancer cells that have migrated through a pre-formed stromal layer of control, untreated WI-38 fibroblasts or WI-38 fibroblasts grown in the presence of either a QSOX1-specific monoclonal antibody (anti-QSOX1, FIGS. 8C-D) or a control antibody (anti-CD19, FIGS. 8E-F) in the culture medium. Two representative fields are shown in each case; FIG. 8G is a bar graph illustrating quantification of migratory cell numbers from panels such as shown in FIGS. 8A-F; and FIGS. 8H-K are photographs illustrating IF staining of laminin in BM from WI-38 cells grown in the absence or presence of QSOX1-specific monoclonal antibody. Two representative fields are shown.

FIGS. 9A-L depict characterization of QSOX1 from confluent fibroblasts. FIGS. 9A-F are photographs depicting HUVEC cells immunostained with Golgi-specific (p115) or ER-specific (GRASP65), and QSOX1 antibodies. DAPI staining (blue) indicates nuclei. Size bar represents 10 µm; FIGS. 9G-J are photographs depicting confluent WI-38 fibroblasts immunostained with Golgi marker p115 (red) and QSOX1 (green). DAPI staining (blue) indicates nuclei. Size bar represents 10 µm; FIG. 9K is a graph illustrating a calibration curve for QSOX1 activity on the model substrate dithiothreitol (DTT) as was generated using the indicated concentrations of rQSOX1. The zero point corresponds to background oxygen consumption in a solution containing DTT but no enzyme. The gray line is the best fit to the six data points. Pink circles indicate the oxygen consumption rates upon DTT addition observed for three supernatant samples from confluent WI-38 fibroblast cultures; and FIG. 9L is a photograph illustrating QSOX1 secretion from various fibroblasts detected by western blot (1=WI-38, 2=normal lung fibroblasts, 3=human foreskin fibroblasts (HFF)). Of note, QSOX1 was not secreted from confluent cultures of the pancreatic epithelial BxPC cell line (epi) or endothelial HUVEC cells (endo).

FIGS. 10A-D depict characterization of QSOX1 from confluent fibroblasts. Mass spectrometry fingerprinting of the two bands observed by SDS-PAGE upon immunoprecipitation of secreted QSOX1. The four residues (PELI) to the right of residue 600 are unique to the shorter QSOX1 splice variant. The 147 additional residues below are unique to the longer splice variant. Bands were digested in-gel with either trypsin or chymotrypsin. Red lettering indicates that an amino acid was observed by LC-MS/MS in at least one peptide. Potential N-linked glycosylation sites are on a gray background. The vertical black bars to the left of residues 601-747 in the right-hand panels indicate sequences found only in the longer QSOX1 splice variant. The presence of red amino acids in this region in both the trypsin and chymotrypsin samples indicates that the QSOX1 upper band must be derived from the longer splice variant.

FIGS. 11A-E depict knockdown of QSOX1. FIG. 11A is a photograph depicting the high effectiveness of knockdown of QSOX1 in WI-38 fibroblasts using siRNA as shown by PCR augmentation of QSOX1 transcript from total RNA and by western blot. The loading control used was Coomassie staining of the blot membrane; FIG. 11B illustrates that QSOX1 knockdown was maintained for at least 4 days following siRNA transfection and resulted in background levels of sulfhydryl oxidase activity in cell culture supernatants, as monitored by oxygen consumption upon addition of DTT. Correspondingly, QSOX1 protein was virtually undetectable in culture supernatants after knockdown; and FIGS. 11C-E are photographs illustrating that QSOX1 knockdown does not promote cellular senescence, as demonstrated by X-gal staining for senescence-associated β-galactosidase activity. Control senescent cells were obtained from a three-week-old culture of WI-38 cells from a high (higher than 32) passage number.

FIGS. 12A-Q depict the effects of QSOX1 knockdown on ECM. FIG. 12A is a bar graph depicting that QSOX1 knockdown leads to increased reactive thiol content in BM. WI-38 fibroblasts were subjected to the indicated siRNA transfection (the DTT and NEM samples were prepared from control transfected cells) and grown for a further four days. Cells were removed with ammonium hydroxide, and ThioGlo was applied to quantify free thiols. DTT and NEM samples were generated by applying 100 mM DTT or 100 mM NEM to control plates, washing out the DTT/NEM, and then treating with ThioGlo; FIGS. 12B-Q are western blotting and immunofluorescence demonstrating increased amounts of laminin-associated proteins in the cell culture supernatants of QSOX1-knockdown cells, but only minor changes in the quantities incorporated into the BM.

FIGS. 13A-N depict the effects of QSOX1 knockdown on ECM. FIGS. 13A-E illustrate laminin staining of fields containing equal numbers of cells showing significant differences in intensity already on day two after transfection; FIG. 13F is a photograph showing that total protein content of BM was not appreciably different for various treatments with siRNA and recombinant QSOX1 as indicated by Coomassie staining of BM samples; FIGS. 13G-L are photographs depicting two independent laminin meshworks with different stabilities co-exist in WI-38 BM. Standard IF staining procedures caused the appearance of large punctae containing laminin, which disappeared in siQSOX1-treated samples but were restored by addition of rQSOX1; FIGS. 13M-N are bar graphs depicting that 50 nM rQSOX1 added one day post-transfection was sufficient to restore normal cell numbers and laminin composition to QSOX1-knockdown cells.

Figure 14:
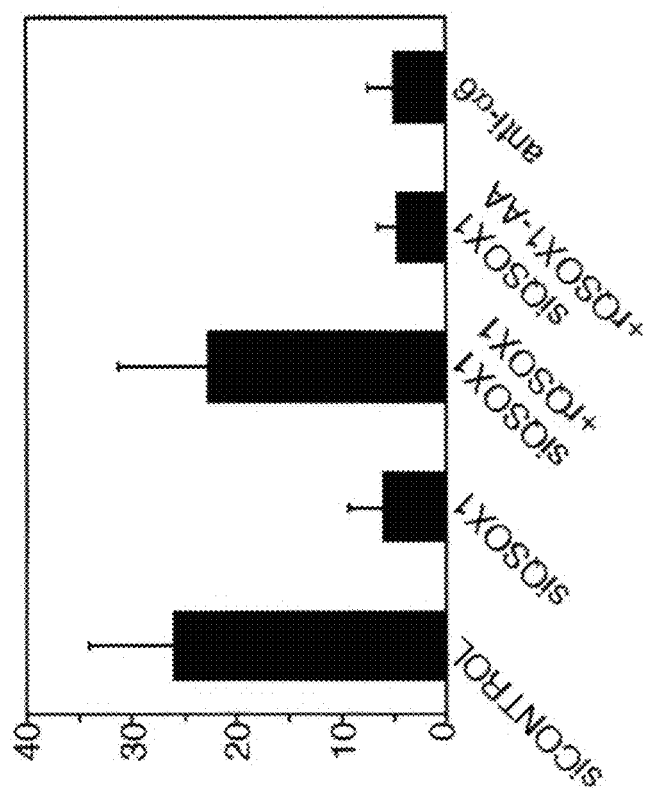

FIG. 14 is a bar graph depicting that QSOX1 produced by pancreatic fibroblasts promotes tumor epithelial cell migration. A quantification of fluorescently labeled BxPC-3 human pancreas cancer cell migration through a pre-formed stromal layer of pancreatic fibroblasts subjected to the indicated treatments.

Figure 15A:
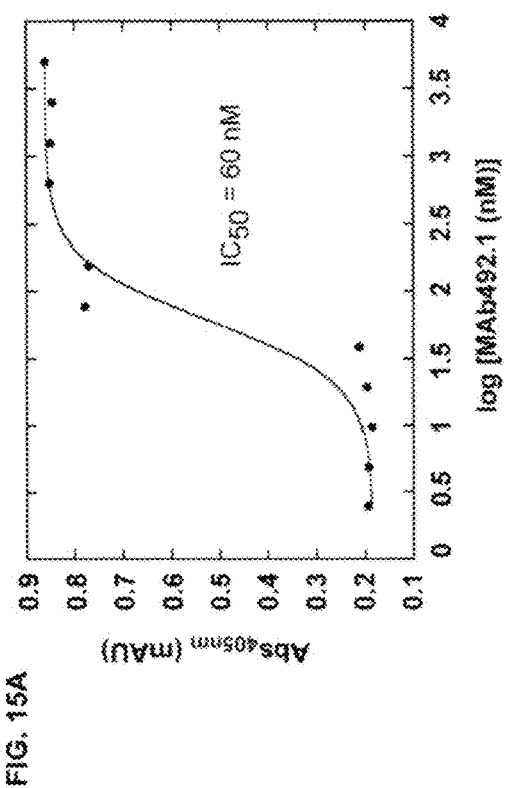
Figure 15B:
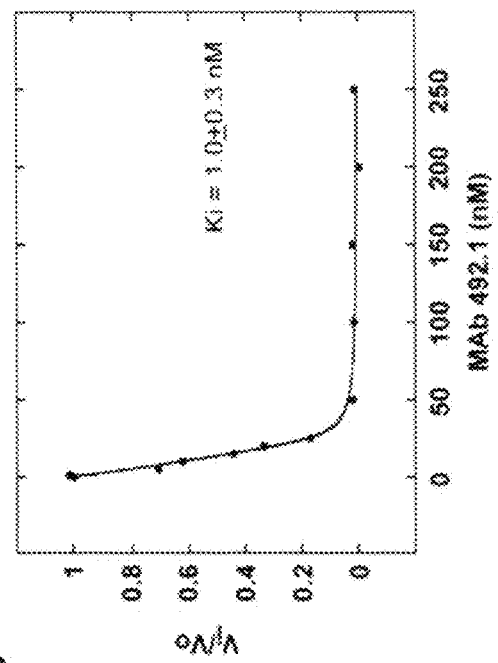
Figure 15D:
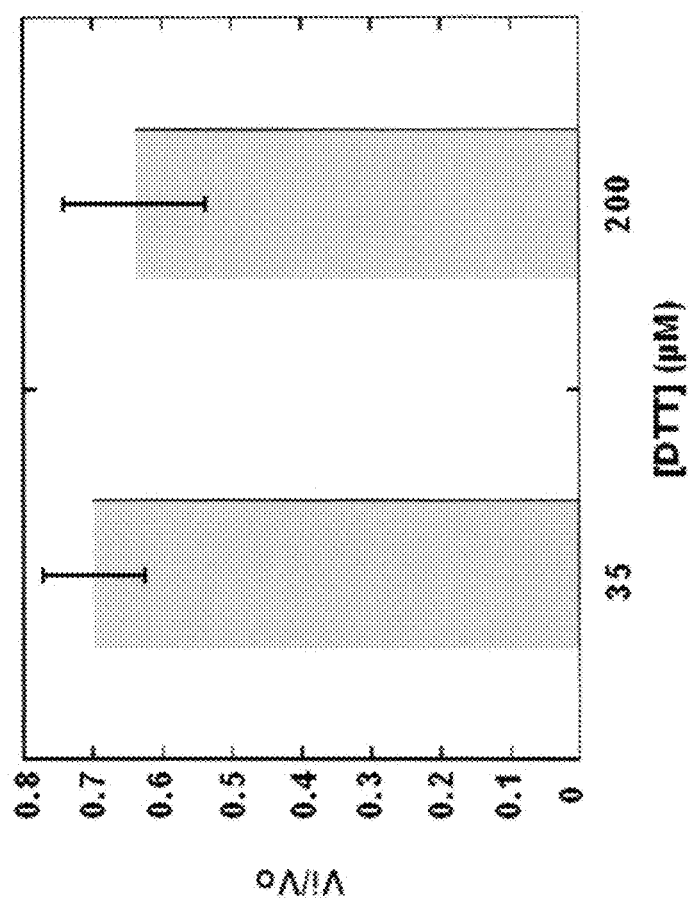

FIGS. 15A-D are line graphs depicting the determination of inhibition constant for MAb492.1. FIG. 15A illustrates a dose response curve of MAb492.1 to 50 nM HsQSOX1, based on results from a colorimetric assay that involves rdRNase oxidation. The inhibitory activity is expressed as absorbance at 405 nm, representing the amount of free thiols that reacted with DTNB, and not oxidized by HsQSOX1. The $IC_{50}$ was determined by nonlinear regression analysis and yielded a value of 60 nM; FIG. 15B illustrates the inhibition curve of MAb492.1 to 25 nM HsQSOX1, based on results from oxygen electrode assays at different MAb492.1 concentrations (ranging from 250 nM to 1 nM). The inhibitory activity is expressed as the ratio of the inhibited rate to the uninhibited rate. The inhibition constant was determined by nonlinear regression analysis and yielded a Ki value of 1.0±0.3 nM; FIG. 15C is a photograph illustrating that 10 nM HsQSOX1 was incubated with or without 250 nM MAb492.1 in the presence of the indicated concentrations of DTT for 10 minutes and quenched by the addition of trichloroacetic acid (TCA). DTT at 200 μM provides a sufficiently high concentration of reducing substrate to obtain initial rates in oxygen consumption assays of HsQSOX1 (the $K_M$ of HsQSOX1 for DTT is approximately 70 μM), but does not lead to antibody reduction and disassembly, and was therefore used in the experiment described in FIG. 15B (see below); and FIG. 15D is a bar graph depicting substrate dependence of MAb492.1 inhibition, based on oxygen consumption assay. The initial velocity of 100 nM HsQSOX1 was measured for two DTT concentrations, 35 μM (0.5 KM) and 200 μM (3 KM), in the absence and presence of 50 nM MAb492.1. The average ratio of three measurements between the initial velocity in the presence of MAb492.1 (vi) to the initial velocity in the absence of MAb492.1 (v0) is displayed for each concentration. Similar ratios at these different concentrations indicate that the inhibition is not substrate-dependent.

FIGS. 16A-D are line graphs depicting that MAb492.1 binds the HsQSOX1 amino-terminal fragment, $HsQSOX1_{Trx}$. FIG. 16A illustrates binding curves of MAb492.1 to full length HsQSOX1, and to its two fragments, based on ELISA binding assay. High absorbance at 630 nm achieved at low target protein concentrations indicates tight binding; and FIGS. 16B-D illustrate migration profiles of full-length HsQSOX1, and its two fragments, obtained from analytical size exclusion chromatography. Gray lines represent the migration profile of MAb492.1 alone. Dashed lines represent the migration profile of HsQSOX1, or one of its fragments, alone. Black lines represent the migration profile of the mixture of MAb492.1 and HsQSOX1 or its fragments.

Figure 17:
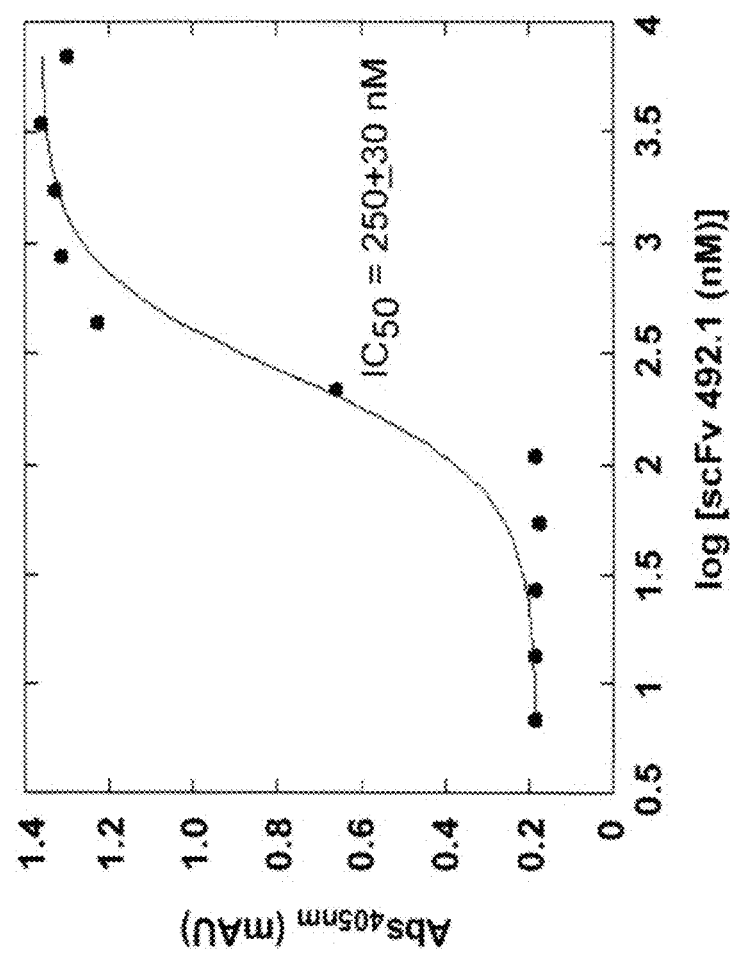

FIG. 17 is a line graph depicting a dose response curve of scFv492.1 to 50 nM HsQSOX1, based on results from a colorimetric assay that involves rdRNase oxidation. The inhibitory activity is expressed as absorbance at 405 nm, representing the amount of free thiols that reacted with DTNB. The $IC_{50}$ was determined by nonlinear regression analysis and yielded a value of 250 nM, five times larger than the $IC_{50}$ value obtained for MAb492.1.

Figure 18:
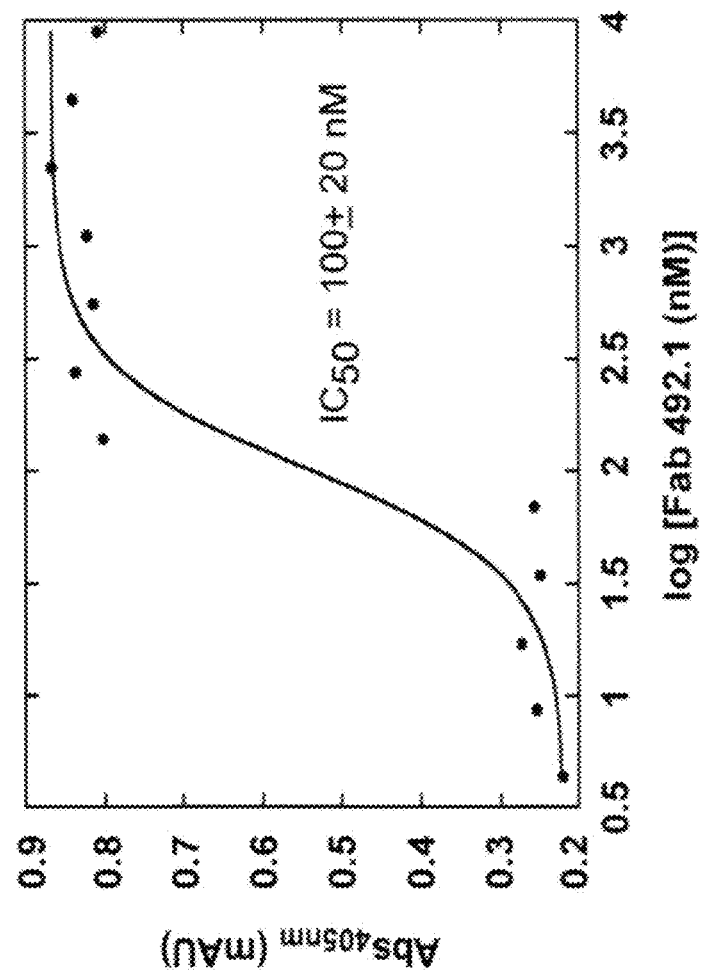

FIG. 18 is a line graph depicting a dose response curve of Fab derived from MAb492.1 to 50 nM HsQSOX1, based on results from a colorimetric assay that involves rdRNase oxidation. The inhibitory activity is expressed as absorbance at 405 nm, representing the amount of free thiols that reacted with DTNB. The $IC_{50}$ was determined by nonlinear regression analysis and yielded a value of 100 nM, twice the $IC_{50}$ value obtained for full length MAb492.1.

Figures 19B, 19C:
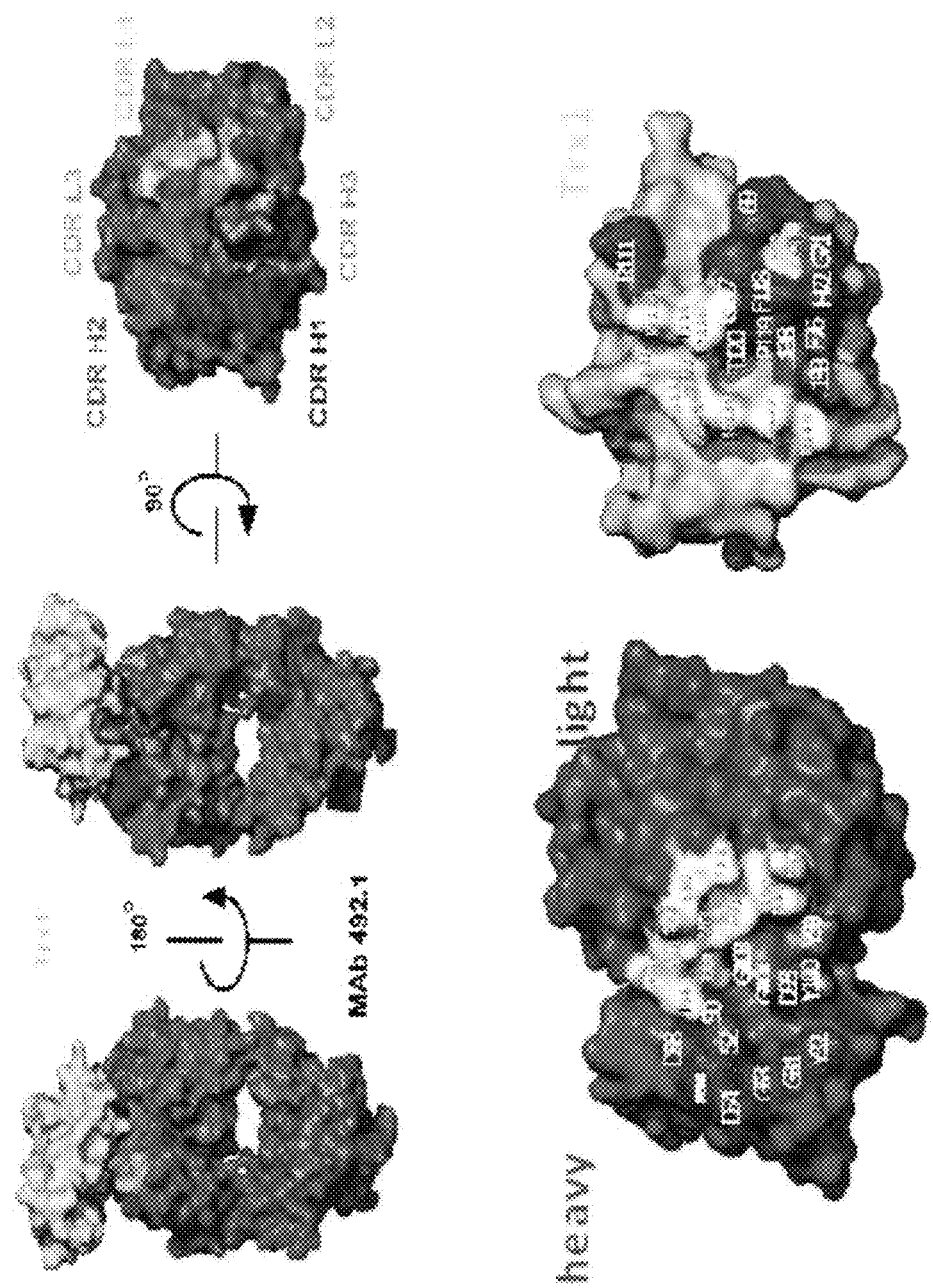

FIGS. 19A-C are schematic illustrations depicting the following: FIG. 19A illustrates the structure of the complex between HsQSOX1$_{Trx}$(Trx1 peach, Trx2 gray, CXXC motif in yellow spheres) and Fab492.1 (heavy chain blue, light chain green). A close up of the binding site is presented with surface presentation; FIG. 19B illustrates a surface presentation of the Fab492.1-HsQSOX1$_{Trx}$ complex and of the CDRs from different angle views. Coloring of Trx1, heavy, and light chains as in A. Labels of CDRs are in colors of the CDRs themselves. On the left Trx1 is shown to have contact with CDR L1, L3, and H2. Rotation of 180° around the y axis shows Trx1 in contact with CDR L2, H1, and H3 (middle). On the right a top view of the surface of all six CDRs; and FIG. 19C illustrates an open book representation of Fab492.1 (left) and Trx1 (right). Trx1 is rotated 180° around a vertical axis relative to Fab492.1. Coloring of Trx1, CXXC motif, heavy, and light chains as in A. Residues from the light chain involved in interactions with Trx1 are in white. Residues from CDR H3 involved in interactions with Trx1 are in raspberry. Residues from CDRs H2 and H1 involved in interactions with Trx1 are in purple. The corresponding interacting residues from Trx1 are in the same colors as the residues from Fab492.1.

FIGS. 20A-B are schematic illustrations depicting Fab492.1-HsQSOX1$_{Trx}$ interface residues from Trx1, from the light chain (FIG. 20A) and heavy chain (FIG. 20B) are presented. Trx1 is shown in white surface, and specific interacting residues are shown in sticks, labeled with black writing. The light chain (green) and heavy chain (blue) are shown in cartoon, and specific interacting residues are shown in sticks. CDRs are labeled. Hydrogen bonds are presented with dashed black lines and their distances are indicated. Cation-π and salt bridges are indicated as well.

FIGS. 21A-O are photographs illustrating fluorescently labeled H460 human lung cancer cells that have migrated through a pre-formed stromal layer of control, untreated WI-38 fibroblasts or WI-38 fibroblasts grown in the presence of MAb492.1 or a control antibody (anti-β actin) in the culture medium. Three representative fields are shown in each case.

Figure 22:
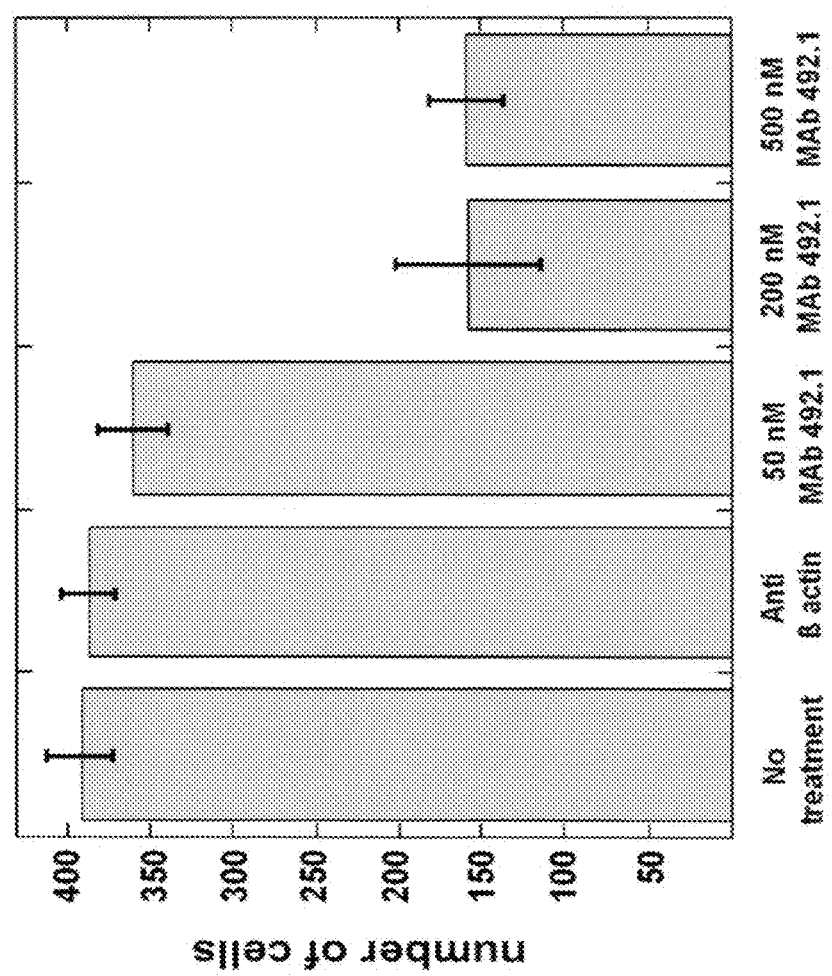

FIG. 22 is a bar graph depicting the inhibition of tumor cell migration by MAb492.1. WI-38 fibroblast cells were grown for four days on a porous membrane and allowed to produce ECM in the presence or absence of different concentration of MAb492.1. Subsequently, fluorescently labeled H460 lung cancer cells were layered onto the fibroblasts. The number of labeled H460 cells that had penetrated the fibroblast layer in each sample after 24 hours is indicated. Of note, this FIG. is a quantification of the panels presented in FIGS. 21A-O.

Figure 23:
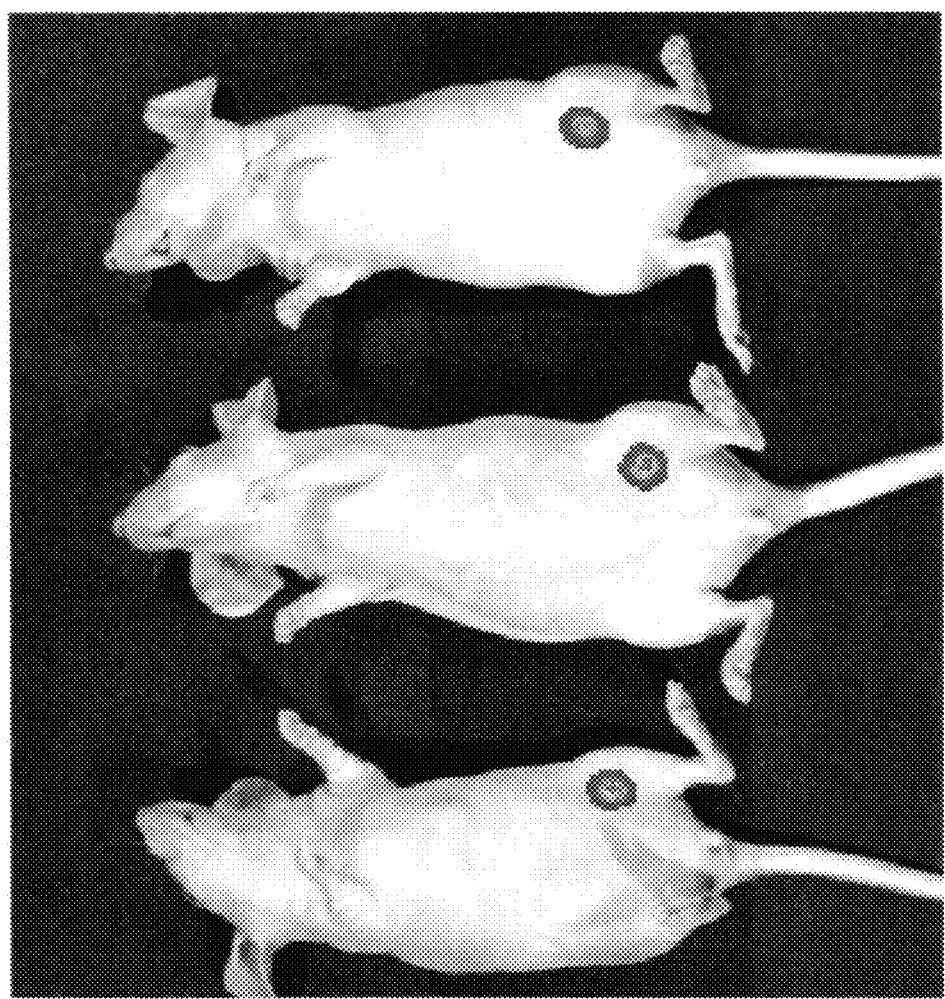

FIG. 23 is an image of bioluminescence emitted from MDA-MB-231 breast cancer cells. The FIG. shows three mice displaying localized tumors one week after co-inoculation of tumor cells and fibroblasts into the mammary fat pad.

Figure 24:
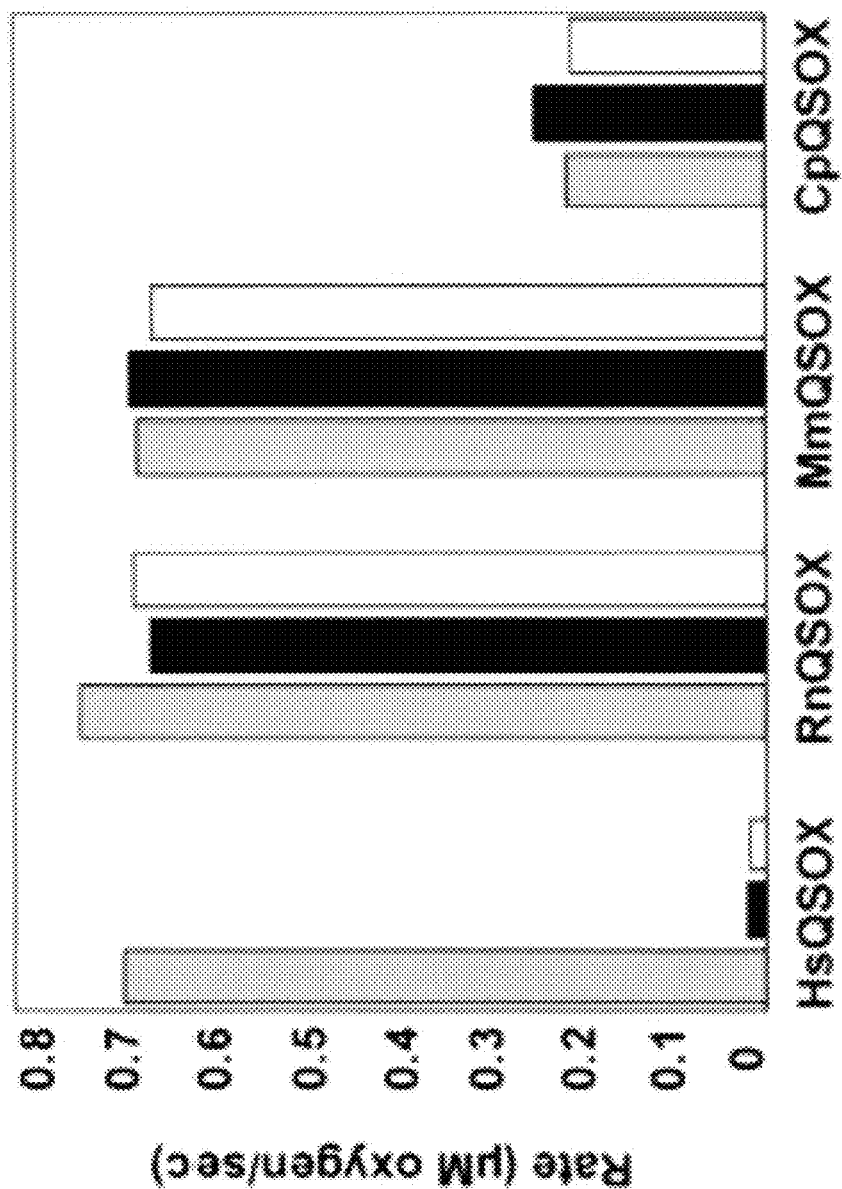

FIG. 24 is a bar graph depicting the activity of various mammalian QSOX1 enzymes in the absence and presence of MAb492.1. The activity rates were evaluated using an oxygen consumption assay. Measurements for each QSOX1 enzyme were conducted in the presence of different MAb492.1 concentrations, and initial slopes (rates) were calculated. Oxygen depletion rates are presented for each QSOX1 enzyme in the absence of MAb492.1 (gray), in the presence of 250 nM MAb492.1 (black), and in the presence of 1 μM MAb492.1 (white). Of note, HsQSOX1 is the only enzyme that was inhibited by MAb492.1 at the MAb492.1 concentrations tested.

FIG. 25 is a sequence alignment of HsQSOX1 to other mammalian QSOX1 enzymes showing the portion of the Trx1 domain that binds MAb492.1, including the active-site CGHC motif and the residues that contact the MAb492.1 light chain and CDR H3. Residues involved in the interactions with MAb492.1 are in bold. Residues from MmQSOX1 (SEQ ID NO: 43), RnQSOX1 (SEQ ID NO: 42), and CpQSOX1 (SEQ ID NO: 41) that differ from the corresponding HsQSOX1 (SEQ ID NO: 3) residues are colored red.

Figure 26:
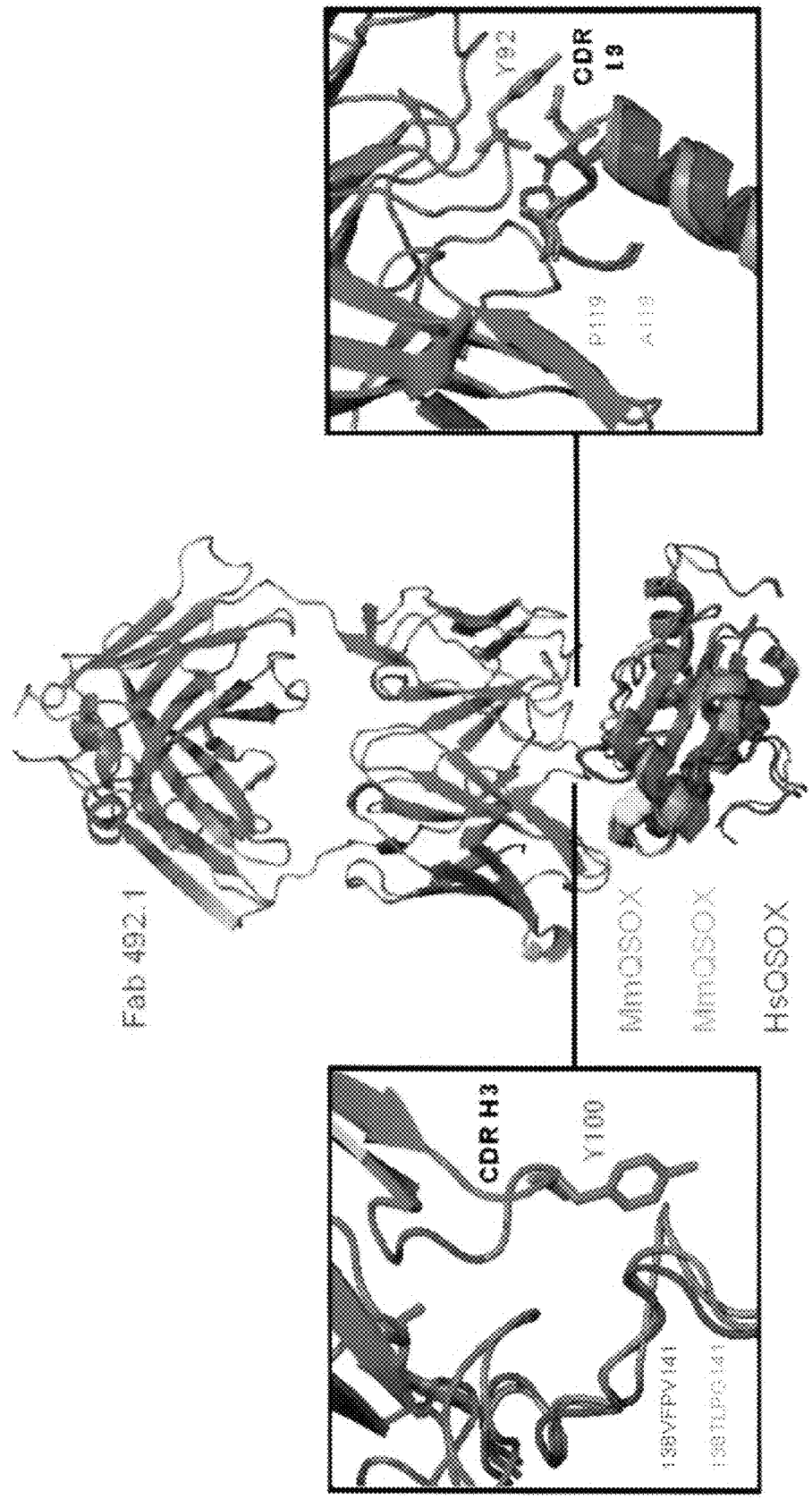

FIG. 26 is a superposition between the structure of the HsQSOX1$_{Trx}$-Fab492.1 complex and the structure of MmQSOX1$_{Trx}$. HsQSOX1$_{Trx}$ is in blue, and the two chains of MmQSOX1$_{Trx}$ from the same asymmetric unit are in green and magenta. The redox-active site cysteines are labeled as two yellow balls. On the right is a close-up of the expected clash between Tyr92 from CDR L3 and Asn117 from MmQSOX1. On the left is a close-up of the expected clash between Tyr100 from CDR H3 and the loop of residues 138-141 from MmQSOX1. Numbering of the HsQSOX1 and MmQSOX1 residues is according to MmQSOX1, for ease of comparison.

Figure 27:
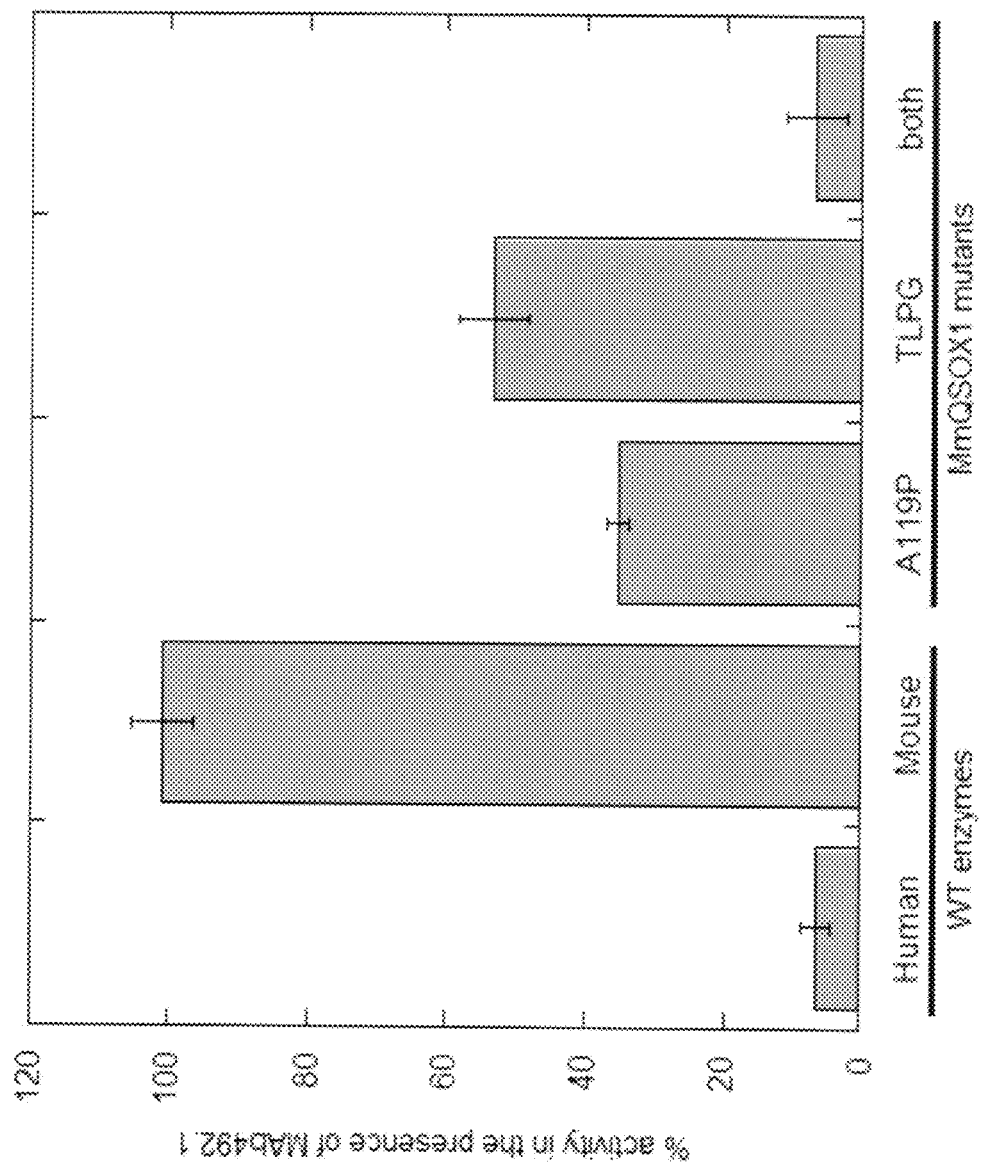

FIG. 27 is a bar graph depicting the percentage activity for different MmQSOX1 mutants in the presence of MAb492.1. Measurements were done three times and averaged. The wild-type MmQSOX1 enzyme is resistant to MAb492.1 inhibition, whereas the TLPG and A119P mutants showed some susceptibility to MAb492.1. MmQSOX1 with both mutations is inhibited to the same degree as HsQSOX1.

DESCRIPTION OF SPECIFIC EMBODIMENTS
OF THE INVENTION

The present invention, in some embodiments thereof, relates to QSOX1 inhibiting agents and, more particularly, but not exclusively, to the use of same for treating laminin-related diseases.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Quiescin sulfhydryl oxidase 1 (QSOX1) is an enzyme that uses a bound flavin adenine dinucleotide (FAD) co-factor to mediate transfer of electrons from pairs of thiol groups in substrate proteins to molecular oxygen, generating hydrogen peroxide as a byproduct. QSOX1 is localized primarily in organelles downstream of the ER in the secretory pathway and undergoes regulated secretion from cells.

Basement membrane (BM) is the layer of extracellular matrix (ECM) at the interface between body cavities or blood vessels and underlying stromal fibroblasts. The BM is composed of laminin, collagen IV, heparin sulfate proteoglycans, entactin, and many other contributing macromolecules. BM is a complex medium for cell adherence and signaling, and its composition and properties profoundly affect the behavior of associated epithelial cells.

While reducing the present invention to practice, the present inventors have uncovered a fundamental role of QSOX1 in assembly of laminin in the basement membrane (BM) and the importance thereof in the interface with tumor cell invasion.

Specifically, the present inventors have illustrated that QSOX1 is required for proper laminin functionality (e.g. assembly and support of cell adhesion and migration) which in turn allows cells and cancer cells in particular to migrate through the basement membrane. The finding of QSOX1 as a primary regulator of the process of laminin assembly points to it as a pivotal target in the metastatic process and cell migration.

While further reducing the present invention to practice, the present inventors were able to produce for the first time inhibitory antibodies to QSOX1 and substantiated its role in laminin assembly and tumor cell migration and, thus, these antibodies may be used for modulation of the basement membrane and as therapeutic agents for inhibition of tumor cell migration.

As is shown hereinbelow and in the Examples section which follows, the present inventors have uncovered that QSOX1 is directly involved in BM assembly (see Example 1 of the Examples section which follows). The BM component most notably affected by QSOX1 is laminin (see FIGS. 12B-Q), with the laminin isoforms most sensitive to the presence of QSOX1 are those containing the α4 chain (see Table 2, hereinbelow). The present inventors observed that depletion of QSOX1 led to the appearance of soluble laminin isoforms in the supernatants of confluent fibroblast cultures (see FIGS. 12B-Q, FIGS. 3A-L and FIG. 4A). The Inventors further observed that BM produced in the absence of QSOX1 failed to support adherence and migration of aggressive tumor epithelial cells (see FIGS. 8A-K).

Moreover, the present inventors generated a monoclonal antibody that binds and inhibits human QSOX1 (HsQSOX1), constructed a recombinant single-chain variable domain version of the antibody, and characterized the antibody binding site on QSOX1 (see Example 2 of the Examples section which follows). The present inventors have illustrated in an in vivo mouse model that treatment with mAb492.1, at a dose of 30 mg/kg, significantly reduced infiltration of breast cancer cells into lymph nodes as compared to mice receiving no treatment (see Tables 6 and 7, hereinbelow).

The present inventors have further shown that HsQSOX1 is comparable to other mammalian QSOX1 orthologs. Alignment of the Trx1 domain sequence of HsQSOX1 with the corresponding region of other QSOX1 enzymes showed that the sequences in the vicinity of the CGHC redox-active motifs are identical (see FIG. 25). However, the region of HsQSOX1 bound by the antibody light chain and CDR H3 sequence (HsQSOX1$_{106-152}$) revealed a few differences compared to other QSOX1 enzymes (see FIG. 25). In particular, Pro 116, which fits well into a cleft between hydrophobic CDR L3 side chains of MAb492.1, is replaced with alanine in other mammalian QSOX1 enzymes. Another region showing sequence differences is $V_{135}$-$V_{138}$ from HsQSOX1, corresponding to Thr$_{138}$-Gly$_{141}$ in MmQSOX1. These discoveries provide the framework for generating antibodies capable of binding mouse QSOX1.

Taken together the present teachings portray a therapeutic value to the QSOX1 inhibiting molecules in the treatment of laminin-associated diseases or conditions such as metastatic tumors.

Thus, according to one aspect of the present invention there is provided a method of inhibiting or preventing laminin assembly in a basement membrane, the method comprising contacting a tissue with an agent which inhibits QSOX1 activity or expression, thereby inhibiting or preventing laminin assembly in the basement membrane.

According to another aspect of the present invention there is provided a method of inhibiting cell migration via a laminin-comprising basement membrane, the method comprising contacting a tissue with an agent which inhibits QSOX1 activity or expression, thereby inhibiting cell migration via the laminin-comprising basement membrane.

As used herein, the term "laminin" refers to a human laminin protein. Typically laminins are trimeric proteins that contain an α-chain, a β-chain, and a γ-chain (found in five, four, and three genetic variants, respectively). Thus, the term laminin as used herein encompasses any type of human laminin, including any of the different chain combinations. The different chains and trimer molecules differ with respect to their tissue distribution apparently reflecting diverse functions in-vivo. Exemplary laminins of the present invention include, but are not limited to, LAMA1, LAMA2, LAMA3, LAMA4, LAMA5, LAMB1, LAMB2, LAMB3, LAMB4, LAMC1, LAMC2 and LAMC3.

According to an embodiment of the present invention, the laminin comprises an alpha 4 chain.

According to a specific embodiment, the laminin is laminin-411 or laminin 421.

As used herein, the term "laminin assembly" refers to the incorporation of laminin proteins into the basal lamina (i.e. one of the layers of the basement membrane).

Typically, laminin is secreted from cells (e.g. fibroblasts, epithelial cells, tumor cells) and is incorporated into cell-associated extracellular matrices where they form independent networks and are associated with type IV collagen networks via entactin, fibronectin and perlecan.

As used herein, the term "basement membrane" or "laminin-comprising basement membrane" refers to the thin layer of fibers which anchors and supports the epithelium and endothelium and comprises the basal lamina (i.e. comprising laminin) As used herein the phrase "inhibiting or preventing laminin assembly" refers to reducing, reversing, attenuating, minimizing, suppressing or halting laminin assembly in a basement membrane. According to one embodiment, inhibiting or preventing laminin assembly is by at least about 10%, by at least about 20%, by at least about 30%, by at least about 40%, by at least about 50%, by at least about 60%, by at least about 70%, by at least about 80%, by at least about 90% or by at least about 100%, as compared laminin assembly in the absence of the QSOX1 inhibitor (as further described hereinbelow). Thus, according to an embodiment of the invention no laminin is incorporated into the basement membrane.

As shown in Example 1 of the Examples section which follows, laminin which is not incorporated into the basal membrane can be found in soluble form (e.g. in the culture medium of in-vitro cultured cells). Thus, monitoring reduction in laminin assembly can be monitored by e.g. immunofluorescence (IF) staining of the extracellular matrix or by Western blotting of the soluble laminin (i.e. that which was not incorporated into the basal membrane).

It will be appreciated that inhibiting or preventing laminin assembly may also be advantageous in situations in which excess connective tissue is produced in a non-structured manner in an organ or tissue in a reparative or reactive process, such as fibrosis. Thus, while further reducing the present invention to practice, inhibition of QSOX1 and subsequently generation of soluble laminin may be therapeutic for fibrotic processes.

It will be appreciated that laminins are an important biologically active part of the basal lamina and basal membrane influencing cell adhesion, signaling, migration, phenotype, differentiation and survival.

As used herein, the term "cell migration" relates to the cell process in which a cell moves from one location to another. An exemplary cell migration of the present invention comprises tumor cell migration leading to metastasis.

Thus, a cell according to the present teachings may comprise, for example, a brain cell, a neuron, a cardiac cell, a muscle cell, a skin cell, a bone cell, a pancreatic cell, a liver cell, a kidney cell, an intestinal cell, a spleen cell, a respiratory cell, a lung cell, a lymphocyte or a monocyte. The cell of the present invention may comprise a healthy cell or may alternately comprise a mutated cell (e.g. a tumor cell).

As used herein the phrase "inhibiting cell migration" refers to reducing, reversing, attenuating, minimizing, suppressing or halting migration of a cell (e.g. tumor cell) via a laminin-comprising basement membrane. According to one embodiment, inhibiting or preventing laminin assembly is by at least about 10%, by at least about 20%, by at least about 30%, by at least about 40%, by at least about 50%, by at least about 60%, by at least about 70%, by at least about 80%, by at least about 90% or by at least about 100%, as compared to cell migration via a laminin-comprising basement membrane in the absence of the QSOX1 inhibitor (as further described hereinbelow). Thus, according to an embodiment of the invention cell migration is completely inhibited through the basement membrane.

As mentioned hereinabove, the methods of the present invention are performed by contacting a tissue with an agent which inhibits QSOX1 activity or expression (also referred to herein as a "QSOX1 inhibitor").

As used herein, the term "QSOX1" relates to the Quiescin Sulfhydryl Oxidase 1 (e.g., human), also called QSCN6. The protein accession number for the long variant of human QSOX1 on the NCBI database is NP_002817 (SEQ ID NO: 1), and the accession number for the short form of human QSOX1 is NP_001004128 (SEQ ID NO: 2). The inhibitors of QSOX1 proteins of the present invention mediate elevation of mis-assembled laminin (i.e. dysfunctional laminin) in the basal membrane.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue and hematopoietic tissue.

According to an embodiment of the present invention, the tissue is a tumor tissue.

According to another embodiment, the tissue comprises fibroblasts.

Downregulation of QSOX1 can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., antagonists, enzymes that cleave the polypeptide and the like, as long as the activity of QSOX1 in mediating proper basement membrane assembly which allows cell migration is inhibited as described above. Specifically, inhibition of basement membrane assembly can be assayed by quantifying the level and localization of soluble laminin as described herein.

According to one embodiment, the agent capable of downregulating a QSOX1 activity is a polypeptide agent.

Exemplary polypeptide agents which may downregulate QSOX1 activity comprise an antibody, an antibody fragment, a peptide, a dominant negative molecule or a natural inhibitor capable of downregulating a QSOX1 activity by specifically binding QSOX1 and interfering with its activity. Preferably, the antibody specifically binds at least one epitope of a QSOX1. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

An exemplary region of QSOX1 which may be targeted for efficient inhibition thereof is the amino-terminal Trx domain (see Example 2 in the Examples section which follows). Specifically, the redox-active disulfide in the Trx1 domain of QSOX1 may be targeted for efficient inhibition.

According to another embodiment, the polypeptide agent may be directed towards amino acid coordinates 34 to 266 of QSOX1 (SEQ ID NOs: 3 and 4).

As described in detail in the Examples section which follows (see Example 2, hereinbelow), the present inventors have generated a monoclonal antibody (mAb) and a single chain antibody (scAb) which specifically target and inhibit QSOX1. Furthermore, the present inventors generated a plasmid, comprising the nucleic acid sequence of human $QSOX1_{33-546}$ (SEQ ID NO: 5) which encodes the recombinant QSOX1 polypeptide (SEQ ID NO: 6) used to elicit antibodies.

Thus, there is provided an isolated polypeptide comprising an amino acid sequence of QSOX1, the peptide being less than 500 amino acids in length.

According to another embodiment, the polypeptide of the present invention may comprise between 50-500 amino acids, between 100-500 amino acids, between 200-500 amino acids, between 300-500 amino acids, between 400-500 amino acids, between 50-100 amino acids, between 100-200 amino acids, between 100-300 amino acids, between 100-400 amino acids, between 200-300 amino acids or between 200-400 amino acids. Preferably, the polypeptide comprises a QSOX1 function in mediating proper basement membrane assembly. The term proper basement membrane assembly is defined as such that supports cell migration.

According to a specific embodiment of the invention, there is provided an isolated polypeptide comprising an amino acid sequence of QSOX1 as set forth in SEQ ID NO: 6.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference). QSOX1 peptides used for immunization may comprise between 50-100 amino acids, between 50-150 amino acids, between 50-200 amino acids, between 50-232 amino acids, between 100-200 amino acids or between 150-232 amino acids.

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (1972)]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains (e.g. [Gly$_4$Ser]$_3$ as taught in Example 2, hereinbelow). Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art.

Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to one embodiment, the antibodies are produced essentially as described hereinbelow. Specifically, mice are first immunized with an emulsion of recombinant human QSOX1 and Complete Freund's adjuvant (e.g. obtained from DifcoLboratories). For instance, mice may be immunized four times at intervals of three weeks. Next, spleen cells from selected mice are fused with myeloma cells (e.g. NSO myeloma cells) using polyethylene glycol. Hybridoma cells are then selected by a selection medium (e.g. HAT medium) and supernatants of the cells are screened for specific binding to human QSOX1 and inhibition thereof. Large scale antibodies may then be produced using, for example, a miniPERM bioreactor (Sarstedt) in serum-free medium (DCCM).

Thus teachings of the present invention provide for an isolated antibody comprising an antigen recognition domain which binds QSOX1 and inhibits a QSOX1 activity in mediating basement membrane assembly that supports cell migration.

According to an embodiment of the invention, the activity is assayed by at least one of an immunofluorescence (IF) staining assay of the extracellular matrix or Western blot assay for soluble laminin (i.e. that which is not incorporated into the basal membrane, as further described in the Examples section which follows).

According to a specific embodiment, the antibody of the present invention is a monoclonal antibody. An exemplary monoclonal antibody which may be used in accordance with the present teachings is MAb492.1 and comprises complementarity determining regions (CDRs) SEQ ID NOs: 29-34. Accordingly, CDRs 1-3 (SEQ ID NOs: 29-31, respectively) are located on the light chain of the antibody and CDRs 1-3 (SEQ ID NOs: 32-34, respectively) are located on the heavy chain of the antibody.

According to another embodiment, the antibody of the present invention is a single chain antibody. An exemplary single chain antibody which may be used in accordance with the present teachings is scFV492.1 and comprises complementarity determining regions (CDRs) SEQ ID NOs: 29-34.

According to another embodiment, an isolated antibody of the present invention comprises the amino acid sequence as set forth in SEQ ID NOs: 7 and 8.

According to another embodiment, an isolated antibody of the present invention comprises the amino acid sequence as set forth in SEQ ID NOs: 27 and 28.

According to one embodiment, the antibody of the present invention may bind a mouse QSOX1 enzyme.

Thus, as described in further detail in the Examples section which follows, human and murine QSOX1 are comparable and comprise a sequence identity of at least 70% (e.g. 79%). Sequence alignment of human and mouse QSOX1 revealed, for example, that Pro 116 of human QSOX1 is replaced with alanine in murine QSOX1 (see FIG. 25). Another region showing sequence differences is $Val_{135}$-$Val_{138}$ from human QSOX1, corresponding to $Thr_{138}$-$Gly_{141}$ in mouse QSOX1 (see FIG. 25). These discoveries provided the framework for generating antibodies capable of binding mouse QSOX1.

According to one embodiment, the antibody of the present invention is a monoclonal anti-mouse QSOX1 antibody.

According to another embodiment, the antibody of the present invention is a single chain anti-mouse QSOX1 antibody.

Possible mutations in MAb492.1 used to generate an antibody that targets mouse QSOX1 are described in Table 8 hereinbelow.

Another agent capable of downregulating QSOX1 is a molecule which binds to and/or cleaves QSOX1. Such molecules can be QSOX1 antagonists, dominant negative molecules of QSOX1 (e.g. part of the peptide or a mutation thereof that competes with effectors), natural inhibitors of QSOX1, or QSOX1 inhibitory peptides.

It will be appreciated that a non-functional analogue of at least a catalytic or binding portion of QSOX1 can be also used as an agent which downregulates QSOX1.

Another agent which can be used along with some embodiments of the invention to downregulate QSOX1 is a molecule which prevents QSOX1 activation or substrate binding.

As mentioned, another agent capable of downregulating expression of QSOX1 is a nucleic acid agent suitable for silencing expression in a targeted manner. Examples of such agents are listed infra.

For example, downregulation of QSOX1 can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., QSOX1) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol. 98, pages 14428-14433. and Diallo et al., Oligonucleotides, Oct. 1, 2003, 13(5): 381-392. doi: 10.1089/154545703322617069.

The invention according to some embodiments thereof also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the QSOX1 mRNA sequence is scanned downstream of the AUG start codon for AA dinucleotide sequences. Occurrence of each AA and the 3' adjacent 19 nucleotides is recorded as potential siRNA target sites.

Preferably, siRNA target sites are selected from the open reading frame, as untranslated regions (UTRs) are richer in regulatory protein binding sites. UTR-binding proteins and/ or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable QSOX1 siRNA can be the siRNA commercially bought from Dharmacon, USA.

It will be appreciated that the RNA silencing agent of some embodiments of the invention need not be limited to those molecules containing only RNA, but further encompasses chemically-modified nucleotides and non-nucleotides.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses(dot)fwdarw(dot) humans) and have been shown to play a role in development, homeostasis, and disease etiology.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Another agent capable of downregulating a QSOX1 is a DNAzyme molecule capable of specifically cleaving an mRNA transcript or DNA sequence of the QSOX1.

DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www(dot)asgt(dot)org). In another application, DNAzymes complementary to bcr-ab 1 oncogenes were successful in inhibiting the oncogenes expression in leukemia cells, and lessening relapse rates in autologous bone marrow transplant in cases of CML and ALL.

Downregulation of a QSOX1 can also be effected by using an antisense polynucleotide capable of specifically hybridizing with an mRNA transcript encoding the QSOX1.

Design of antisense molecules which can be used to efficiently downregulate a QSOX1 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating a QSOX1 is a ribozyme molecule capable of specifically cleaving an mRNA transcript encoding a QSOX1. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

The methods of the present invention (e.g., inhibiting cell migration) may be effected in-vitro, in-vivo or ex-vivo.

The ability to modulate cell migration can be used as a novel therapeutic modality.

Thus, according to another aspect of the present invention there is provided a method of treating a laminin-associated disease or condition in a subject in need thereof the method comprising administering to the subject a therapeutically effective amount of an agent which inhibits QSOX1 activity or expression.

As used herein, the term "laminin-associated disease or condition" refers to a disease or condition in which laminin function is associated with the onset or progression of a disease.

The term "treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" refers to an animal, preferably a mammal, most preferably a human being, including both young and old human beings of both genders who suffer from or are predisposed to a necrosis related disorder or condition.

According to one embodiment, the laminin-associated disease or condition is a tumor.

Examples of tumors include, but are not limited to, carcinoma, blastoma and sarcoma. Particular examples of cancerous diseases but are not limited to: Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletal myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to an embodiment, the tumor is a metastasizing solid tumor.

According to an embodiment, the tumor is an adenocarcinoma.

According to another embodiment, the tumors which may be treated in accordance with the present teachings, include but are not limited to, prostate cancer, lung cancer, breast cancer, cervical cancer, urachus cancer, vaginal cancer, colon cancer, esophagus cancer, pancreatic cancer, throat cancer, stomach cancer and myeloid leukemia.

According to one embodiment, the laminin-associated disease or condition is associated with fibrosis.

The term "fibrosis" refers to a formation or a presence of excess connective tissue in an organ or tissue. It may occur as a repair or replacement response to a stimulus such as tissue injury or inflammation.

Examples of disorders involving fibrosis include, but are not limited to, liver fibrosis, pulmonary fibrosis, renal fibrosis, pancreatic fibrosis, scleroderma, connective tissue diseases, scarring, skin fibrosis, cardiac fibrosis, organ transplant, vascular stenosis, restenosis, arterial fibrosis, arthrofibrosis, breast fibrosis, muscle fibrosis, retroperitoneal fibrosis, thyroid fibrosis, lymph node fibrosis, bladder fibrosis, pleural fibrosis and COPD.

According to one embodiment, the laminin-associated disease or condition is a bacterial disease, a viral disease or a parasitic disease.

An exemplary parasitic disease which may be treated by the teachings of the present invention includes African trypanosomiasis.

According to the present teachings, in order to treat the laminin-associated disease or condition, the subject is administered with an agent which downregulates QSOX1 activity or expression, as further detailed hereinabove.

Each of the downregulating agents described hereinabove can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the QSOX1 downregulating agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (QSOX1 downregulating agent) effective to prevent, alleviate or ameliorate symptoms of a disorder (e.g., laminin-associated disease or condition) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays.

For example, a dose can be formulated in animal models to achieve a desired concentration or titer. Such information can be used to more accurately determine useful doses in humans.

Animal models for laminin-associated diseases include, for example, the murine animal model for liver fibrosis [see e.g. review paper by Hiromitsu Hayashi and Takao Sakail, Amer Journal Physiol—GI (2011) 300(5): G729-G738] and the murine animal model for metastatic breast cancer [Anna Fantozzi and Gerhard Christofori, Breast Cancer Research (2006) 8:212].

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

It will be appreciated that the anti-mouse QSOX1 antibodies of some embodiments of the present invention may be used for preclinical trials to determine the therapeutic effective amount, toxicity and the efficacy of the antibodies for treatment.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that since the isolated polypeptide (e.g. antibody) of the present invention is capable of specifically binding QSOX1, and since QSOX1 levels are elevated in medical conditions associated with laminin (e.g. tumors), such a polypeptide can be used in the diagnosis of a laminin-associated disease or condition.

Thus, according to an aspect of the present invention there is provided a method of diagnosing a laminin-associated disease or condition in a subject comprising: (a) contacting a biological sample of the subject with the isolated polypeptide of the present invention under conditions suitable for immunocomplex formation between the isolated polypeptide and QSOX1 proteins; and (b) detecting formation of the immunocomplex, wherein a presence of the immunocomplex above a predetermined threshold (i.e., the level of the same in a biological sample obtained from a healthy individual) is indicative of the laminin-associated disease.

As used herein the phrase "diagnosing" refers to classifying a laminin-associated disease or condition, determining a severity of the disease, monitoring disease progression, forecasting an outcome of a disease and/or prospects of recovery.

As used herein "biological sample" refers to a sample of tissue or fluid isolated from a subject, including but not limited to, cells (e.g. fibroblast cells, neuronal cells, dendritic cells, epithelial cells, etc.), tissues, organs, various tumors (e.g. tumor biopsy sample) and fluids such as blood, serum, plasma, lymph, bile fluid, urine, saliva, sputum, synovial fluid, semen, tears, cerebrospinal fluid, bronchioalveolar large fluid, ascites fluid, pus, conditioned medium, and also samples of in vivo cell culture constituents. A "biological sample of the subject" may also optionally comprise a sample that has not been physically removed from the subject.

According to an embodiment, the method of the present invention enables diagnosis of a tumor, such as a metastasizing solid tumor (e.g. prostate cancer, pancreatic cancer, breast cancer etc.).

Diagnosis of laminin-associated disease according to the present invention is effected by contacting the biological sample of the subject with the isolated polypeptide of the present invention under conditions suitable for immunocomplex formation between the isolated polypeptide (e.g. antibody) and QSOX1 proteins.

As used herein the term "immunocomplex" refers to a complex formed between an antibody (e.g., the isolated polypeptide of the present invention) and its specific antigen (QSOX1 proteins).

The immunocomplex of the present invention can be formed at a variety of temperatures, salt concentration and pH values which may vary depending on the isolated polypeptide used and the QSOX1 proteins and those of skills in the art are capable of adjusting the conditions suitable for the formation of each immunocomplex.

According to the method of this aspect of the present invention, detection of immunocomplex formation is indicative of a diagnosis of the laminin-associated disease or condition. Various methods can be used to detect the immunocomplex of the present invention and those of skills in the art are capable of determining which method is suitable for each immunocomplex and/or the type of biological sample used for diagnosis.

For example, the immunocomplex can be detected by conventional immunohistochemistry or immunofluorescence, FACS, ELISA, Western blot and RIA analyses, or by a molecular weight-based approach.

It will be appreciated that the isolated polypeptide (e.g. antibody) of some embodiments of the present invention may be attached to a detectable moiety in order to enable detection of the immunocomplex.

Various types of detectable or reporter moieties may be conjugated to the antibody of the invention. These include, but not are limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.].

Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532.

Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimmer or tetramer form of the antibody).

Table 1 provides non-limiting examples of identifiable moieties which can be conjugated to the antibody of the invention.

TABLE 1

| Identifiable Moiety | Amino Acid sequence (GenBank Accession No.) | Nucleic Acid sequence (GenBank Accession No.) |
|---|---|---|
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin lygase tag | LHHILDAQKMVWNHR | |
| orange fluorescent protein | AAL33917 | AF435432 |
| Beta galactosidase | ACH42114 | EU626139 |
| Streptavidin | AAM49066 | AF283893 |

Furthermore, in order to isolate the immunocomplex, the isolated peptide (e.g. antibody) may be immobilized on a solid support. As used herein the phrase "solid support" refers to a non-aqueous matrix to which a reagent of interest (e.g., the isolated polypeptide of this aspect of the present invention) can adhere. Examples of solid supports, include, but are not limited to, solid supports formed partially or entirely of glass (e.g., controlled pore glass), polysaccharides (e.g., agarose), polyacrylamides, polystyrene, polyvinyl alcohol and silicones. In certain embodiments, depending on the context, the solid support can comprise the well of an assay plate; in others it is a purification column (e.g., an affinity chromatography column). This term also includes a discontinuous solid phase of discrete particles, such as those described in U.S. Pat. No. 4,275,149.

The agents described hereinabove for detection of immunocomplex formation may be included in a diagnostic kit/article of manufacture preferably along with appropriate instructions for use and labels indicating FDA approval for use in diagnosing and/or assessing a laminin-associated disease.

Such a kit can include, for example, at least one container including at least one of the above described diagnostic agents (e.g., antibodies) and an imaging reagent packed in another container (e.g., enzymes, secondary antibodies, buffers, chromogenic substrates, fluorogenic material). The kit may also include appropriate buffers and preservatives for improving the shelf-life of the kit.

According to another aspect of the present invention, there is provided a kit for detecting a level of QSOX1 in a biological sample.

As described in detail in the Examples section which follows (see Example 1, hereinbelow), the present inventors have shown that inhibition/depletion of QSOX1 causes laminin assembly defects in the basement membrane.

Thus, according to another aspect of the present invention, there is provided a method of identifying a QSOX1 inhibitor, the method comprising culturing a tissue in the presence or absence of a test agent, wherein a decrease in functional basement membrane following the culturing with the test agent is indicative that the test agent is the QSOX1 inhibitor.

According to an embodiment of the invention, a decrease in functional basement membrane comprises a decrease in laminin assembly in the basement membrane.

As used herein, the phrase "a decrease in functional basement membrane" refers to a decrease of at least about 10%, by at least about 20%, by at least about 30%, by at least about 40%, by at least about 50%, by at least about 60%, by at least about 70%, by at least about 80%, by at least about 90% or by at least about 100%. Thus, preferably no laminin is incorporated into the basement membrane.

According to another embodiment, the decrease in laminin assembly comprises an increase in soluble laminin in the tissue.

According to another embodiment, the tissue comprises a tissue culture.

According to another embodiment, the method is performed in vivo.

According to another embodiment, the method further comprises a decrease in QSOX1 activity or expression level. The decrease in QSOX1 activity or expression level may be of at least about 10%, by at least about 20%, by at least about 30%, by at least about 40%, by at least about 50%, by at least about 60%, by at least about 70%, by at least about 80%, by at least about 90% or by at least about 100%.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

The Disulfide Catalyst QSOX1 Promotes Tumor Cell Migration by Incorporation of Key Basement Membrane Components Materials and Experimental Procedures Cell Lines and Maintenance WI-38 lung fibroblasts (Coriell) were maintained in Minimal Essential Medium (MEM) supplemented with 15% FBS, L-glutamine, and antibiotics as recommended by the supplier. HFF cells and pancreatic fibroblast cells were maintained in MEM supplemented with 10% FBS, L-glutamine, and antibiotics. BxPC-3 and H460 epithelial cells were maintained in DMEM supplemented with 10% FBS, L-glutamine and antibiotics.

siRNA Transfection

QSOX1 specific and scrambled siRNA oligonucleotides were transfected into fibroblasts according to the manufacturer's instructions (Dharmacon). Briefly, cells were seeded at approximately 75% confluence and incubated for 6 hr with 50 nM siRNA and Dharmafect1 transfection buffer in serum-free Opti-MEM media. Following incubation, the transfection mixture was aspirated, and MEM containing 10% FBS was added to the cells.

Immunofluorescence

Cells were grown on glass cover slips in a 24-well plate to desired confluence.

For intracellular staining, cells were fixed for 30 min at RT with 3.7% formaldehyde, followed by permeabilization in 0.1% Triton X-100 for 2 min, and then rinsed 3 times in phosphate buffer saline (PBS) containing 0.1% Tween (PBS-T). Cells were then incubated for one hr with 5% BSA in PBS-T, followed by incubation with primary antibody (20 μg/ml unless specified otherwise by manufacturer) in 5% BSA in PBS for 1 hr at RT or over-night at 4° C., washed in PBS, and incubated with fluorescently-labeled secondary antibody in 5% BSA in PBS-T for 1 hr at RT.

Following an additional 3 washes, coverslips were placed, cells face down, onto a 5 µl drop of ProLong Gold antifade reagent (Invitrogen) on glass slides and were left to dry overnight protected from light. Samples were observed on a DeltaVision imaging system (Applied Precision). For ECM protein labeling, cells and their associated matrix were incubated with 5% BSA in PBS-T and labeled with primary antibody. Samples were then fixed with 3.7% formaldehyde and treated with secondary antibody.

ECM Purification and ThioGlo Staining

Cell cultures were grown in 24 well dishes and transfected as described in the results section (hereinbelow) and figure description (hereinabove). Cells were stripped by treatment with 20 mM $NH_4OH$ for 1 min, followed by 6 washes with 1 mM EDTA/PBS (pH 7.4). After the last wash, positive and negative control ECM samples were treated with 100 mM DTT (in 1 mM EDTA/PBS) or 100 mM NEM (added from a 250 mM stock in 5% acetonitrile), respectively, for 1 hr at 37° C. Samples were then washed 4 times with 1 mM EDTA/PBS, then incubated with 6 µM ThioGlo reagent for 30 min at RT (protected from light). The reaction was terminated by the addition of 2 µl 2 N HCl, and emission was measured using an ELISA plate reader (ex: 379 nm, em: 513 nm).

Oxygen Consumption Assay

A Clarke-type oxygen electrode (Hansatech Instruments Ltd.) was used to monitor changes in dissolved oxygen concentrations as a measure of sulfhydryl oxidase activity. Purified QSOX1 was assayed in 50 mM potassium phosphate buffer, pH 7.5, 65 mM NaCl, 1 mM EDTA. Reactions were started by injection of dithiothreitol (DTT) to a concentration of 5 mM in the electrode reaction chamber. Sulfhydryl oxidase activity in cell culture supernatants was assayed similarly, following injection of 5 mM DTT into the supernatant solution.

Mass Spectrometry Analysis

Gel fragments were treated protease at 37° C. in 50 mM ammonium bicarbonate.

Peptide mixtures were extracted from the gels with 80% $CH_3CN$, 1% $CF_3COOH$, and the organic solvent was evaporated in a vacuum centrifuge. The resulting peptide mixtures were reconstituted in 80% formic acid and immediately diluted 1:10 with Milli-Q water prior to mass spectrometry analysis. Tandem mass spectrometry (LC-MS/MS) was performed using a 15 cm reversed phase spraying fused-silica capillary column (inner diameter 75 µm) made in-house and packed with 3 µm ReproSil-Pur $C_{18}AQ$ media (Ammerbuch-Entringen, Germany) using an UltiMate 3000 Capillary/Nano LC System (LC Packings, Dionex). The LC system was used in conjunction with an LTQ Orbitrap (Thermo Fisher Scientific) operated in the positive ion mode and equipped with a nanoelectrospray ion source. Peptides were separated with a 50 min gradient from 5 to 65% acetonitrile (buffer A: 5% acetonitrile, 0.1% formic acid, 0.005% TFA; buffer B: 90% acetonitrile, 0.2% formic acid, 0.005% TFA). Survey MS scans were acquired in the Orbitrap with the resolution set to a value of 60,000. Up to the six most intense ions per scan were fragmented and analyzed in the linear trap. For the analysis of peptides, survey scans were recorded in the FT-mode followed by data-dependent collision-induced dissociation (CID) of the six most intense ions in the linear ion trap (LTQ). Raw data files were searched with MASCOT (Matrix Science, London, UK) against a Swissprot database.

Invasion Assays

Fibroblasts were seeded in the upper chambers of 24-well BD BioCoat plates with 8.0 µm pore size membrane inserts. Cells were transfected and supplemented with rQSOX1 as described in the results section (hereinbelow) and figure description (hereinabove), and were allowed to grow for 4 days to reach confluence. On the fourth day, $5\times10^4$ epithelial cells, pre-labeled with the cell-tracker dye CSFE (Molecular Probes) according to the manufacturer's instructions, were layered onto the fibroblasts.

The inner chamber was filled with serum-free MEM, and the outer chamber with MEM containing 10% FBS. Epithelial cells were allowed to migrate across the membrane for 24 hr at 37° C. Non-invading cells were manually scraped off the upper face of the membrane and discarded, and invading cells on the lower face were fixed in 3.7% formaldehyde, imaged, and quantified.

Cell Adherence Assay

Fibroblasts were grown in a 24-well plate and were transfected and supplemented with rQSOX1 as described in the results section and figure legends. On day 4 after transfection, fibroblasts were incubated for 1 hr with 5% BSA in PBS, and 1 set of samples was supplemented with α6-antibody. Following washes with PBS-T, $10^5$ epithelial cells, pre-labeled with the cell-tracker dye CSFE, were layered on the fibroblasts and incubated for 1 hr at 37° C. Plates were then sealed with plastic and centrifuged upside-down for 5 min at 50×g to remove cells. Following centrifugation, cells that remained attached to the plates were trypsinized, re-suspended in PBS, and counted by flow cytometry.

Senescence Staining

Cells were transfected as described in the results section and figure legends. Prior to SA-β-Gal staining, cells were fixed with 0.5% glutaraldehyde 15 min at RT, followed by 3 washes with $PBS/MgCl_2$ (pH 6.0). Fresh X-gal solution was then added, and the cells were incubated for 3 hr at 37° C. protected from light. Cells were then washed 3 times with PBS and imaged immediately.

Scanning Electron Microscopy

WI-38 cells were grown on glass cover slips of diameter 13 mm Cells were fixed for 1 hr at RT with 3% paraformaldehyde and 2% glutaraldehyde in 0.1 M cacodylate buffer, pH 7.2, 5 mM $CaCl_2$, 1% sucrose. After rinsing with 0.1 M cacodylate buffer containing 1% sucrose 3 times (5 min each), cells were treated with 1% Os04 in 0.1 M cacodylate buffer, pH 7.2, 5 min $CaCl_2$, 1% sucrose for 1 hr at room temperature. Samples was then washed 5 times with 0.1 M cacodylate buffer, 5 times with water, incubated for 5 min with 1% tannic acid, and washed again 5 times with water. Samples were incubated in 1% uranyl acetate for 30 min and washed again 5 times with water. For dehydration, samples were incubated for 5 min each successively in 25%, 50%, 70%, 96%, and 100% ethanol. Samples were imaged using a FEG-SEM LEO Supra 55 electron microscope.

NF/CAF Isolation

NF and CAF were obtained from a surgically resected lung tumor (CAF) or from a healthy area (NF) of the same specimen. Signed consent, as required by the Institutional Review Board (IRB), was obtained from patients. Tissues were minced and incubated overnight at 37° C. with constant shaking in DMEM containing type 4 collagenase. Cells were then filtered and plated in DMEM containing 20% FBS, 1 mM sodium pyruvate, 2 mM L-glutamine, non-essential amino acids, antibiotics, and 60 µM β-mercaptoethanol for 7-14 days, then moved to medium containing 10% FBS.

Fibroblast identity was confirmed by typical morphology, positive vimentin staining, and negative cytokeratin staining. Cells were frozen in aliquots and thawed 7 days before each experiment. Following thawing, fibroblasts were grown to 70% confluence, and then medium was replaced with either control medium or H460 conditioned medium. Cell harvesting and RNA analysis were performed at 48 hrs.

Conditioned Media

Confluent lung (H460) and pancreas (BxPC-3) epithelial cells were grown in culture plates. Conditioned media was collected after 5 days and centrifuged to eliminate debris.

Real-Time Reverse Transcription-PCR Analysis

Total RNA was extracted using the NucleoSpin kit (Macherey Nagel, Germany). One microgram of RNA was reverse transcribed with Moloney murine leukemia virus reverse transcriptase and random hexamer primers. Quantitative real time PCR was performed using SYBR Green PCR Master Mix on an ABI 7300 instrument (Applied Biosystems). Primers were designed using the Primer Express software, and expression level was normalized by that of the GAPDH housekeeping gene in the same sample.

Histological Immunostaining

Formalin-fixed tissues from breast cancer patients were dehydrated, embedded in paraffin, and sectioned at 4 μm. Slides were warmed to 60° C. for 1 hr, dewaxed in xylene, and dehydrated. An endogenous peroxidase block was performed for 10 min in 3% $H_2O_2$/methanol. After rinses in TBS, sections were incubated one hr at room temperature with a purified antibody to QSOX1 (1:50). Detection was performed with Super Picture POLY HRP Conjugate (Invitrogen). Briefly, sections were incubated for 30 min at room temperature with POLY HRP Conjugate. The antibody binding was visualized with the substrate chromagen AEC. Sections were counterstained with hematoxylin and cover-slipped with an aqueous mounting fluid (Glycergel, Dako). The stained sections were reviewed with a light microscope and analyzed.

Microarray Analysis

For laminin transcript quantification, WI-38 cells were treated with either siCONTROL, siQSOX1, or siQSOX1+ rQSOX1, and total RNA was extracted using the RNeasy mini kit (Qiagen). The quality of the RNA was assessed using the Bioanalyzer 2100 platform (Agilent). The samples were then processed and hybridized to Affymetrix human 2.0 microarrays using the Affymetrix GeneChip system according to manufacturer's instructions.

Atomic Force Microscopy

AFM measurements were made on a Bruker Bioscope with Nanoscope 4 controller, using a colloidal (1 μm radius borosilicate) tip and 0.03 N/m cantilever (Novascan). Force-distance curves were performed at 0.5 Hz without scanning on sample. Elastic moduli were calculated using a Herzian model fit to the ingoing curves. Several dozen force curves were acquired on each of 3 control samples and 2 QSOX1 knockdown samples.

Results

Active QSOX1 is Secreted from Quiescent Fibroblasts

QSOX1 transiently expressed in cultured epithelial cells was previously shown to be localized to the Golgi apparatus [Chakravarthi S. et al. (2007). Biochem. J. 404, 403-411]. Endogenous QSOX1 in neurons and neuroendocrine glands was also previously suggested to be Golgi localized [Tury A. et al. (2004) J. Endocrinol. 183, 353-363]. The present inventors raised polyclonal antibodies and demonstrated localization of endogenous QSOX1 to the Golgi in endothelial and epithelial cells (FIGS. 9A-J). In sub-confluent fibroblasts, QSOX1 was also found in the Golgi (FIGS. 1C-J). Upon reaching confluence, however, the intracellular staining pattern in fibroblasts changed, appearing to correspond to the movement of QSOX1 to secretory vesicles (FIGS. 9A-J).

QSOX1 levels were previously shown to increase in the growth medium of WI-38 fibroblasts as they became confluent and entered quiescence (Coppock et al., 2000, supra). WI-38 cells, derived from lung, a tissue abundant with QSOX1 but not its paralog QSOX2. The present inventors confirmed exclusive QSOX1 transcription and protein secretion to the culture medium of confluent fibroblasts (FIG. 1K). Secreted QSOX1 levels increased over time (FIG. 1L), in correlation with an increase in sulfhydryl oxidase activity, as measured by oxygen consumption assay (FIG. 1M).

QSOX1 activity in confluent cell culture medium was comparable to 40-50 nM wild-type recombinant QSOX1 (rQSOX1) (FIG. 9K). QSOX1 secretion was shown to be a general phenomenon of confluent fibroblasts from various origins. In particular, cancer associated fibroblasts (CAF) from pancreas and lung, normal lung fibroblasts, and human foreskin fibroblasts secreted QSOX1 into the growth media (FIG. 9L). In contrast, the epithelial and endothelial cells tested, though expressing QSOX1 intracellularly, did not secrete the enzyme even a few days after reaching confluence (data not shown).

Western blots of QSOX1 secreted to fibroblast growth media consistently showed a doublet of bands by SDS-PAGE at approximately 80-90 kD (FIG. 1L). The two known splice variants of the QSOX1 transcript encode a soluble protein of calculated molecular weight of approximately 76 kD, including oligosaccharide modifications, and a protein of approximately 92 kD containing a predicted carboxy-terminal transmembrane segment. To determine the source of the two QSOX1 species observed by western blot, the present inventors immunoprecipitated QSOX1 from culture supernatant and subjected the two bands to liquid chromatography tandem mass spectrometry (LC-MS/MS) (FIGS. 10A-D). Peptides recovered from the lower band were derived only from the region common to both splice variants. Some peptides recovered from the upper band, however, were from regions unique to the longer splice variant. No peptide covering the cytosolic tail or transmembrane region of the longer splice variant was observed. One possible explanation for these observations was that the longer splice variant was biosynthesized with its transmembrane region, and the soluble ectodomain was shed upon post-translational cleavage in the secretory pathway or at the cell surface.

Extracellular QSOX1 is Required for Fibroblast Adhesion

QSOX1 was depleted from fibroblasts using small interfering RNA (siRNA). Transfection with QSOX1-specific siRNA lowered QSOX1 mRNA and secreted enzyme below detectable levels, and led to a corresponding drop in extracellular sulfhydryl oxidase activity to background rates (FIG. 11A) Immunofluorescence staining of fibroblasts transfected with QSOX1 siRNA showed very few cells (approximately 5%) retaining detectable levels of intracellular protein. QSOX1 depletion was maintained for at least four days post-transfection (FIG. 11B). The most evident effect of QSOX1 depletion from fibroblasts was a decrease in cell number (FIGS. 2A-E). Four days post-transfection, the QSOX1-depleted cell count was approximately 50% of control cells. Addition of 50 nM rQSOX1 to the culture media of QSOX1-depleted cells 24 hours post-transfection completely restored cell numbers. In contrast, addition of 50 nM catalytically inactive rQSOX1 (rQSOX1-AA), in which the amino-terminal redox-active cysteines (C70 and C73)

were replaced by alanines (FIG. 2F), had no effect. The possibility that hydrogen peroxide, the byproduct of QSOX1-mediated disulfide formation, is required for normal cell proliferation was ruled out by treatment of control cells with catalase, an enzyme that dismutates hydrogen peroxide to oxygen and water, without detectable effect (data not shown). These data establish the importance of catalytically active extracellular QSOX1 and the formation of disulfide bonds for fibroblast proliferation in culture.

Several scenarios could lead to decreased cell numbers following QSOX1 depletion in fibroblasts. In particular, extracellular QSOX1 activity may promote cell proliferation, or lack of QSOX1 may induce apoptosis, quiescence, or senescence.

Annexin V staining indicated that apoptosis was insignificant in QSOX1-knockdown cells (data not shown). Neither did QSOX1 knockdown cause cells to become senescent, according to X-gal staining for senescence-associated β-galactosidase activity (FIGS. 11C-E). Furthermore, staining with propidium iodide on day four after siRNA treatment suggested that QSOX1 depletion did not cause exit from the cell cycle (data not shown). Inventors noted that there was no significant difference in cell numbers between QSOX1 depleted and control cultures up to 48 hours post-transfection. Starting on the third day, however, cell numbers began to diverge, and detached cells began to appear in the culture media of QSOX1 depleted samples (FIGS. 2G-H). Addition of rQSOX1 to the fibroblast culture one day post-transfection prevented cell detachment later on, in addition to restoring cell numbers, as noted above. QSOX1 depletion may exacerbate the reduced adhesion of mitotic cells that is exploited in the "mitotic shake-off" technique, resulting in loss of cells from the monolayer even without intentional agitation.

QSOX1 Depletion Causes Laminin Assembly Defects in Basement Membrane

Inventors next sought to identify the molecular defects that resulted in cell detachment in the absence of extracellular QSOX1. Extracellular matrix (ECM) proteins are major targets for adhesion receptors. It was previously noted that transcripts for a variety of ECM components increased in confluent fibroblasts along with QSOX1 mRNA (Coppock et al., 1993, supra). The present inventors reasoned that if QSOX1 is required for formation of disulfide bonds in collagens or other ECM components, depletion of QSOX1 may result in excess unpaired cysteines in the ECM. Indeed, extracellular matrix isolated from QSOX1-depleted fibroblasts had increased levels of reactive thiols as indicated by labeling with the thiol-specific fluorophore ThioGlo1 (FIG. 12A). Thiol levels were in large part restored by addition of rQSOX1 to the culture media after siRNA transfection, but not by addition of rQSOX1-AA. These data provide the first indication that QSOX1 catalyzes disulfide formation within proteins of the extracellular matrix.

The ECM components produced by WI-38 fibroblasts are those that constitute the basement membrane (BM), the thin fibrous layer that underlies the epithelium and endothelium. Inventors have referred hereinafter to the ECM produced by cultured WI-38 cells as BM, though the matrix is removed from its physiological context relative to body surfaces and cavities. Major constituents of the BM include collagen IV and laminin, which polymerize to form fibrous meshworks, and perlecan, entactin, and agrin, which bridge the collagen IV and laminin scaffolds. To determine if any of these BM constituents are impacted by QSOX1 extracellular activity, immunofluorescence (IF) staining and western blotting were used to analyze, respectively, cells and culture media derived from fibroblasts four days after QSOX1 specific siRNA transfection. In this manner, the present inventors monitored changes in BM morphology and composition, as well as changes in the levels of soluble versions of proteins due to failure of incorporation into the BM. No significant changes were detected in collagen IV by western blot or IF upon QSOX1 depletion (FIGS. 12B-Q). However, major defects in laminin incorporation were observed in the absence of QSOX1. Four days after QSOX1 depletion, soluble laminin could be detected by western blot in culture media, and a 74% reduction in extracellular laminin IF staining was measured compared to control cells (FIGS. 3A-L and 4A). Changes in laminin following QSOX1 depletion were completely reversed by the exogenous addition of rQSOX1 to the culture media after siRNA transfection, but not by addition of rQSOX1-AA, indicating that sulfhydryl oxidase activity is required for laminin incorporation into the BM. Though a decrease in total amount of laminin could be expected in view of the decrease in total cell number upon QSOX1 knockdown, inventors found decreased laminin levels even when equal numbers of cells were imaged (FIG. 13A).

Additionally, cell detachment began on the third day post-transfection, whereas decreased laminin in matrix could be detected already at 48 hours (FIG. 13A), and total content of extracellular protein was by and large equal between control and QSOX1-depleted cells (FIG. 13F). Finally, and most importantly, soluble laminin was detected in the culture media only in the absence of QSOX1 (FIG. 4B), indicating a defect in assembly rather than a mere change in quantity.

To further dissect the role of extracellular QSOX1 in the assembly of laminin into the basement membrane, inventors assessed the concentration and time-dependence of rQSOX1 addition to QSOX1-depleted cells (FIG. 13M). Inventors found that 50 nM rQSOX1 added 24 hour post-transfection repaired the extracellular defects, such as decreased cell adhesion and deficient laminin incorporation into the BM, caused by QSOX1 depletion with siRNA. Higher rQSOX1 concentrations (i.e., 125 nM) did not increase cell numbers or laminin assembly above the levels of control cells or QSOX1 knockdown cells treated with 50 nM rQSOX1, indicating that QSOX1 activity was not limiting above 50 nM. In contrast, 25 nM rQSOX1 was insufficient to completely reverse the effects of QSOX1 depletion. When 50 nM rQSOX1 was added 72 rather than 24 hours post-transfection, the effects of QSOX1 depletion were not reversed (not shown). The time dependence of exogenous enzyme addition suggests that the secretion of QSOX1 and laminin must be temporally correlated, or the window of opportunity for BM incorporation of laminin is lost.

It is expected that perturbation of laminin assembly would also influence laminin binding proteins. Basement membrane is rich in laminin-interacting proteins, including perlecan, entactin, agrin, netrin, and fibronectin. These proteins also interact with the collagen IV network and with cell surface receptors. Inventors observed soluble perlecan, entactin, agrin, and fibronectin in culture media of QSOX1 depleted fibroblasts to a greater extent than in the media of control cells (FIGS. 12C-E).

However, at most a minor decrease in each of these proteins was detected by IF in BM of QSOX1-depleted cells (FIGS. 12G-I, 12K-M). These data are consistent with a defect in the laminin network in the absence of QSOX1 and a consequent impact on laminin-interacting proteins, but suggest that interactions with collagen IV or cell-surface proteins are sufficient to preserve their BM incorporation to a large extent.

QSOX1 Affects Particular Laminin Isoforms

Laminin is secreted from the cell as a cross-shaped heterotrimer consisting of three chains known as α, β, and γ. Five α subunit isoforms, 4 β isoforms, and 3 γ isoforms are known in humans, and 16 different chain combinations, expressed in different tissues and developmental stages, have been discovered to date. According to contemporary nomenclature, these laminin types are designated by their chain composition, e g, laminin-111 contains the α1, β1, and β1 chains. The antibody used to detect changes in laminin above was polyclonal to fragment P1, which is a highly conserved antigenic determinant of laminin trimers. The P1 antibody therefore recognizes multiple laminin isoforms. IF staining for P1 nevertheless hinted at the co-existence of multiple, distinct laminin matrices in BM produced by confluent WI-38 cells. The present inventors noted that a delicate laminin matrix was observed in both control and QSOX1 knockdown samples. However, an additional laminin population, which under standard IF staining procedures appeared as large amorphous patches (FIGS. 13G-H, 13K-L), was found only in control cells. The different appearance of the two laminin populations under the same fixation and staining protocol indicated the existence of two qualitatively different types of laminin, only one of which was sensitive to the presence of QSOX1. Subsequent refinement of the staining protocol (see 'materials and methods section' above) preserved the mesh-like appearance of the QSOX1-dependent laminin network to yield images such as those in FIGS. 3A-L.

Information regarding the laminin isoforms expressed in WI-38 fibroblasts was obtained from RNA microarray analyses of control and QSOX1-depleted cells. inventors found that laminin-411, -421, -221, and -211 are potentially expressed most abundantly in these cells and that, aside from a minor increase in transcripts for the al and α2 chains, QSOX1 depletion did not alter laminin chain mRNA levels significantly (Table 2, below). IF staining with specific antibodies revealed a profound decrease in the α4 chain of laminin in the BM upon QSOX1 depletion, whereas the α2 chain was unchanged (FIGS. 3M-R and 4C). Therefore, incorporation of laminin-411 or laminin-421, but not laminin-221 or laminin-211, is the precise event affected by extracellular QSOX1. Furthermore, laminin-411 or -421 is likely to correspond to the large laminin patches seen using standard IF staining procedures, as described above. Regions of BM rich in α2-chain laminin tended to be rich in α4-chain laminin as well, but the α4-containing matrix extended into regions poor in α2-containing laminin (FIGS. 3M-R).

TABLE 2

Laminin isoform expression levels

| gene | siQ vs. siC | siQ + r vs. siC | siQ + r vs. siQ | Level in siC |
|---|---|---|---|---|
| LAMA1 | 1.6 | 1.5 | −1.1 | 6.7 |
| LAMA2 | 1.5 | 2.5 | 1.7 | 7.8 |
| LAMA3 | ND | ND | ND | ND |
| LAMA4 | −1.0 | −1.2 | −1.2 | 10.3 |
| LAMA5 | ND | ND | ND | ND |
| LAMB1 | 1.1 | −1.0 | −1.1 | 10.8 |
| LAMB2 | −1.3 | −1.3 | −1.1 | 8.1 |
| LAMB3 | ND | ND | ND | ND |
| LAMB4 | ND | ND | ND | ND |
| LAMC1 | 1.1 | 1.0 | −1.0 | 10.7 |
| LAMC2 | ND | ND | ND | ND |
| LAMC3 | ND | ND | ND | ND | mRNA transcript levels in WI-38 fibroblasts treated with control siRNA or QSOX1-specific siRNA, with or without supplementation with rQSOX1, were determined using microarray analysis. Fold changes between the various sample pairs and normalized (relative to a selected set of reference mRNA) levels in control WI-38 cells were given Insight into the ultrastructure of the QSOX1-dependent laminin matrix was obtained using scanning electron microscopy (SEM). SEM revealed an abundance of a clustered filigree-like material in the extracellular environment of control WI-38 cells (FIGS. 5A-F). Material with this appearance was not detected in association with QSOX1 knockdown cells. Taken together, observations made using SEM and IF suggested that QSOX1 is required for proper BM assembly of only particular laminin isoforms displaying a distinctive ultrastructure. Furthermore, the sensitivity to staining protocol suggests that the QSOX1-dependent laminin mesh is naturally less firmly affixed to the cell surface or to other BM components than those laminin networks deposited in the BM independently of QSOX1 activity.

QSOX is Required for Tumor Epithelial Cell Migration

Laminin isoforms promote and support tumor epithelial cell migration during metastasis. The transcripts for both QSOX1 and the laminin α4 chain, encoded by the LAMA4 gene, were previously found to increase significantly in fibroblasts surrounding invasive breast carcinoma compared to normal breast fibroblasts [Finak G. et al. (2008) Nature Med. 14, 518-527]. The present data, demonstrating a specific requirement for QSOX1 in assembly of α4-containing laminins, suggests a mechanistic consequence of LAMA4/QSOX1 co-induction in cancer-associated stroma. To test whether QSOX1 extracellular activity affects the interaction of tumor cells with surrounding stroma, inventors utilized an organotypic invasion assay. This assay monitored the ability of H460 metastatic lung epithelial cells, pre-labeled with a fluorescent cytoplasmic dye, to migrate through a pre-formed layer of WI-38 lung fibroblasts and their associated BM (FIG. 5G). Epithelial cell migration was attenuated by approximately 60% when QSOX1 was depleted during formation of the fibroblast layer (FIGS. 6A-O). When QSOX1-depleted fibroblasts were supplemented with exogenous rQSOX1, tumor cell migration was re-established. However, addition of rQSOX1-AA did not support migration. Similar results were obtained using pancreatic fibroblasts and epithelial cells, indicating the generality of migration inhibition upon QSOX1 depletion (FIG. 14). Similar results were obtained for paired pancreatic fibroblasts and epithelial cells (FIGS. 6R-S), indicating the generality of QSOX1 catalytic activity in construction of pro-migratory ECM. Though QSOX1-depleted fibroblast monolayers were more elastic than controls (FIG. 6T), suggesting greater penetrability, their failure to support migration is consistent with the known role of laminin in integrin-mediated adhesion, a pre-requisite for tumor metastasis.

To exclude the possibility that QSOX1 acts directly on tumor epithelial cells to promote their migration, a migration assay was performed in the absence of the fibroblast layer. H460 migration through Matrigel-coated porous membrane was quantified in the presence or absence of rQSOX1 in the culture media. Addition of rQSOX1 had no detectable effect, demonstrating that QSOX1 does not directly promote tumor cell migration. Additionally, to exclude the possibility that the poor migration of tumor cells on a fibroblast layer lacking QSOX1 is due to decreased epithelial cell viability, H460 cells were layered on WI-38 fibroblasts on a glass cover slip. No difference in uptake of a cell viability tracer was detected between H460 cells on control vs. QSOX1-depleted fibroblasts (data not shown). Taken together, these data support the conclusion that QSOX1 extracellular activity indeed promotes migration of tumor epithelial cells through fibroblast-secreted BM through its effects on the stromal layer.

Epithelial Cells Require QSOX1 for Firm Adhesion to BM During Migration

Defects in fibroblast adhesion correlated with perturbed laminin assembly in QSOX1-deficient mono-cultures as described above. To test whether the compromised ability of epithelial cells to migrate through a QSOX1-depleted fibroblast layer is also due to adhesion defects, inventors assessed epithelial cell adhesion using centrifugation.

Epithelial cells were placed on pre-formed fibroblast layers, and adhesion strengths were compared by applying a controlled force. Upon subjection to an acceleration of 50 g for 5 minutes, H460 epithelial cells detached more readily (44.9% detachment) from QSOX1-depleted WI-38 fibroblasts than from control cells (4.5% detachment). Addition of rQSOX1 to growing cultures of QSOX1-depleted fibroblasts restored adhesion of epithelial cells subsequently layered upon them, whereas addition of rQSOX1-AA did not. Inventors conclude that QSOX1 extracellular catalytic activity facilitates formation of a stromal layer to which tumor cells effectively adhere, with consequent facilitation of tumor cell migration.

Laminins are recognized by cell-surface integrins, which are heterodimers of $\alpha$ and $\beta$ chains that serve as fundamental mediators of cell-cell and cell-matrix adhesion. Integrin $\alpha 6\beta 1$ is a major receptor for laminin on epithelial cells, although $\alpha 6\beta 4$ and $\alpha 3\beta 1$ were also previously shown to bind laminin. If QSOX1 knockdown indeed decreases cell adhesion and migration due to laminin deficiency, inventors would expect direct blocking of laminin receptor to have a comparable effect. Metastatic epithelial cells pre-treated with an $\alpha 6$ blocking antibody for one hour showed decreased migration through the layer of fibroblasts and their associated BM, to a similar extent as observed upon QSOX1 knockdown (FIG. 6P). Decreased adhesion of anti-$\alpha 6$ treated epithelial cells to fibroblast-secreted matrix was also demonstrated in the centrifugation cell adhesion assay (FIG. 6Q). These data are consistent with fewer laminin-integrin interactions underlying the adhesion and migration defects observed upon QSOX1 knockdown.

Cross-Talk Between Tumor Epithelial Cells and Fibroblasts Induces QSOX1 Secretion and Promotes Migration In vivo, fibroblasts embedded in the BM surrounding organs and blood vessels exchange signals with the epithelium and endothelium through secreted factors. The present data shows that QSOX1 secretion promotes cell adhesion, basement membrane assembly, and cell migration, all of which could support tumor cell proliferation and metastasis. Since epithelial cells are not known to secrete QSOX1, inventors next tested whether tumor cells recruit adjacent fibroblasts to induce QSOX1 expression and secretion. To this end, sub-confluent WI-38 cells, which typically express lower levels of QSOX1 and do not detectibly secrete it, were cultured for two days with conditioned media derived from the H460 lung carcinoma cell line. Exposure to conditioned media enhanced secretion of QSOX1 from the fibroblasts (FIG. 7A). This finding was reproduced with fibroblasts and epithelial tumor cells from a pancreatic source (FIG. 7A). Additionally, incubation of fibroblasts with tumor cell-conditioned media facilitated subsequent epithelial cell migration across the matrix to a greater extent than incubation with normal medium (data not shown).

Ex Vivo Analysis of Fibroblasts from Cancer Patients

In the studies described above, inventors knocked down QSOX1 expression in cultured cells and then supplied the culture media with recombinant enzyme to elucidate the role of extracellular QSOX1. Through these perturbations, inventors discovered that QSOX1 contributes to laminin assembly in the BM and to cell adhesion and migration.

To further probe the role of QSOX1 in tumor progression and metastasis development, inventors turned to an ex-vivo experimental system: primary fibroblasts from lung cancer patients. Explanted fibroblasts were purified from cancer associated tissue (CAF, cancer-associated fibroblasts) or adjacent healthy tissue (NF, normal fibroblasts) and maintained as described in the 'materials and experimental procedures' section above. An RNA microarray analysis of cells from one patient showed that QSOX1 transcription in the CAF sample was greater than in the NF sample, and both cell types responded to incubation with tumor derived conditioned media by increasing QSOX1 transcription levels (data not shown). Real-time PCR analysis for three more patients showed that CAF consistently expressed higher levels of QSOX1 than NF (FIG. 7B). Western blot analysis of these ex vivo fibroblasts showed that QSOX1 secretion correlated with transcription; CAF secreted more QSOX1 than NF, and NF showed enhanced secretion following incubation with tumor conditioned media.

Immunohistochemical staining of tumor sections removed from breast cancer patients confirmed the conclusions from ex vivo fibroblasts. Whereas the most prominent QSOX1 staining was evident in epithelial cells of the tumors, fibroblasts adjacent to tumors showed more intense staining of QSOX1 than fibroblasts more distant from the growths (FIGS. 7C-D).

Control of BM Assembly and Tumor Cell Migration by Inhibition of Extracellular QSOX1

The present findings suggest that inhibition of QSOX1 may be a powerful strategy to control BM composition and thereby the tumor microenvironment. The present inventors therefore developed inhibitory monoclonal antibodies against QSOX1 (see Example 2, hereinbelow). When these antibodies were supplied to the growth medium of WI-38 fibroblasts as they approached confluence, fewer cell numbers were observed in the culture monolayer after four days compared to untreated cells or cells treated with a control antibody (FIGS. 8A-K). Furthermore, dramatically diminished staining of the laminin $\alpha 4$ chain was observed in BM produced by cells grown in the presence of the QSOX1 monoclonal antibody (as described in Example 2 below).

Finally, organotypic invasion assays of the type performed on cells treated with QSOX1 siRNA, as described above, showed a major drop in tumor epithelial cell migration through the fibroblast layer when the latter was produced in the presence of the QSOX1 inhibitor. Together these results show that inhibition of QSOX1 produced by cells expressing and secreting the enzyme can be used to modulate the composition and functionality of the BM.

Example 2

An Inhibitory Antibody Targeting the Disulfide Catalyst QSOX1 Perturbs Extracellular Matrix Formation by Blocking the First Step in a Dithiol/Disulfide Relay Materials and Experimental Procedures
Plasmid Construction
Recombinant HsQSOX1 used to elicit antibody production was described previously [Alon et al., (2012) *Nature*

488, 414-418]. ScFv and HsQSOX1 synthetic genes codon-optimized for protein production in *E. coli* (Genescript) were cloned between the NdeI and BamHI sites of the pET-15b vector (Novagen). The amino-terminal and carboxy-terminal HsQSOX1 fragments construction was previously described [Akin et al., (2012) *Nature* 488, 414-418 and Alon et al., (2010) *FEBS Lett.* 584, 1521-1525].

$HsQSOX1_{33-546}$

HsQSOX1 isoform b cDNA clone (ID 4447666) from human kidney mRNA was obtained from Invitrogen in the vector pCMV•SPORT6. The desired construct was amplified by PCR with an N'-terminal forward primer (SEQ ID NO: 39) omitting the signal sequence and incorporating an NdeI restriction site, and a C'-terminal reverse primer (SEQ ID NO: 40) incorporating a stop codon followed by a BamHI site.

The PCR product and the pET15b expression vector were restricted with NdeI and BamHI. The vector was further treated with calf intestinal alkaline phosphatase (CIP) to remove 5' flanking phosphates and prevent re-ligation of the vector. The $His_6$ tag and thrombin cleavage site were replaced with a $His_6$ tag directly connected to the protein. This modification was done by restriction with NcoI and NdeI followed by CIP. Oligonucleotides encoding $His_6$ with flanking nucleotides that create the staggered ends sites compatible with NcoI and NdeI restriction sites were boiled and annealed. Since these oligonucleotides were not restricted but rather designed to mimic the enzymatic restriction, phosphate groups were added enzymatically following annealing, and the primers were then ligated to the vector.

The final expression vector encoded the sequence set forth in SEQ ID NO: 6.

Recombinant HsQSOX1 Expression and Purification

HsQSOX1 injected to mice was expressed and purified as previously described [Alon et al., (2012) *Nature* 488, 414-418]. HsQSOX1 used for other purposes was expressed and purified similarly, only its amino-terminal $His_6$ tag was cleaved after purification on a Ni-NTA column (GE Healthcare). The eluted enzyme was exchanged into 20 mM sodium phosphate buffer, pH 7.4, 100 mM NaCl, 20 mM imidazole using a PD-10 desalting column (GE Healthcare). Thrombin (10 units/mg protein) was added, and was incubated overnight at room temperature for the cleavage reaction. PMSF was added to 1 mM to inhibit the thrombin, and the protein was re-applied to a Ni-NTA column. Further purification was performed by size exclusion chromatography, in 20 mM sodium phosphate buffer, pH 7.5, 200 mM NaCl, 0.5 mM EDTA.

The amino-terminal and carboxy-terminal HsQSOX1 fragments expression and purification were carried out as previously described [Alon et al., (2012) *Nature* 488, 414-418 and Alon et al., (2010) *FEBS Lett.* 584, 1521-1525].

Generation of Mouse Anti HsQSOX1 Monoclonal Antibody

Hybridomas were generated by the Kohler-Milstein method as previously described [Kohler G. and Milstein C. (1974) *Nature* 256, 495-497]. Five BALB/c mice (12 weeks old) were immunized with emulsion of recombinant HsQSOX1 and Complete Freund's adjuvant (DifcoLboratories) four times at intervals of three weeks.

Spleen cells from selected mice were fused with NSO myeloma cells using polyethylene glycol as previously described [Galfre G. et al. (1977) *Nature* 266, 550-552]. Hybridoma cells were selected by HAT medium. Supernatants of the cells were screened for HsQSOX1 binding and inhibition (see below). MAb492.1 was produced in large scale with a miniPERM bioreactor (Sarstedt) in serum-free medium (DCCM).

Monoclonal Antibody Purification

Serum was dialyzed through a 10,000 MW cutoff membrane (Thermo) against 20 mM sodium phosphate buffer, pH 7, and loaded on a protein G column (GE Healthcare). Antibodies were eluted from the column with 100 mM glycine buffer, pH 3, and immediately neutralized with 10% 1 M Tris buffer, pH 8.

ELISA Binding Assay

A 96 well plate (Nunc) was coated with 100 µL of 5 µg/ml recombinant HsQSOX1, or 5% BSA in phosphate buffer saline (PBS) containing 0.1% tween (PBS-T) as a control, for one hr at 37° C. The wells were blocked with 5% BSA in PBS-T at RT for 1 hr. Different mouse anti-HsQSOX1 clones and sub-clones were added to the wells for 1 hr at RT. Wells were washed 3 times with 300 µL PBS-T. Polyclonal goat anti-mouse antibody conjugated to Horseradish peroxidase (HRP) in 5% BSA was added at a 1:2500 dilution and incubated at RT for 30 min. Wells were washed 3 times with 300 µL PBS-T. Absorbance was read at 630 nm in a microplate reader (TECAN) immediately after addition of 100 µL 3,3',5,5'-Tetramethylbenzidine (Millipore).

HsQSOX1 Inhibition Assay

Reactions of 100 µL volume were conducted in 96 well plates (Nunc). Reduced and denatured RNaseA (Sigma) was used as a model substrate and was prepared as follows. Ten mg RNase was dissolved in 1 ml of 20 mM phosphate buffer, pH 6.5, 6 M GuHCl, and 100 mM DTT, and incubated at 37° C. for 1 hr. The protein was desalted on a PD-10 column (GE Healthcare) equilibrated with DDW, and its thiol content was determined by DTNB absorbance at 412 nm. 50 nM recombinant HsQSOX1 and various concentrations of monoclonal antibody clones were incubated for 30 min at RT. Reactions were initiated with the addition of 200 µM RNase thiols and were quenched after 25 min with 1 mM DTNB. Absorbance was measured at 405 nm in a microplate reader.

Variable Region Sequencing

Total RNA was extracted from approximately $11 \times 10^6$ anti HsQSOX1 hybridoma cells using the RNeasy mini kit (Qiagen). Five hundred ng total RNA was reverse transcribed into first-strand cDNA by using polydT primer and 20 units of Moloney murine leukemia virus reverse transcriptase. The variable region of the light chain was amplified using degenerate primers as previously described [Benhar I. and Reiter, Y. (2002) *Curr. Protoc. Immunol., Chapter* 10, unit 10.19B], and the variable region of the heavy chain was amplified using optimized primers for mouse scFv repertoire cloning as previously described [Zhou H. et al. (1994) *Nuc. Acids Res.* 22, 888-889]. PCR products of approximately 300 bp were gel extracted with the HiYield Gel/PCR DNA fragments extraction kit (RBCBioscience), and cloned into pGEM-T easy vector (Promega). The inserts were sequenced using T7 and SP6 primers and analyzed by the IMGT database. Sequences were verified by Tandem mass spectrometry (LC-MS/MS) [Alon et al., (2012) *Nature* 488, 414-418].

Analytical Size Exclusion Chromatography

100 µL of 20 µM HsQSOX1, its fragments, or MAb492.1 were loaded onto a superdex 200 column (GE HealthCare) equilibrated with 20 mM sodium phosphate buffer, pH 7.4, 200 mM NaCl, and 1 mM EDTA at a flow rate of 1 ml/min. The complexes (200 µL) of HsQSOX1, or its fragments, with MAb492.1 were injected after 30 min co-incubation at RT.

ScFv Expression, Purification, and Refolding

ScFv492.1 was produced in the BL21 (DE3) plysS *E. coli* strain grown in LB medium supplemented with 100 μg/ml ampicillin and 30 μg/ml chloramphenicol.

Transformed cells were grown at 37° C., and induction was carried out by addition of IPTG to a concentration of 0.5 mM when cells reached an optical density of 0.5 at 595 nm After induction, cells were grown overnight at 25° C. Cells were harvested by centrifugation for 30 min at 4000 rpm. Cell pellets were suspended in 20 mM sodium phosphate buffer, pH 7.4, 500 mM NaCl, and 20 mM imidazole, supplemented with protease inhibitors. The cell lysate was centrifuged at 40,000×g for 1 hr. Pellets were dissolved in 50 mM Tris buffer, pH 8, 100 mM NaCl, 1 mM EDTA, and 0.5% triton X-100, sonicated 3 times for 30 sec, and centrifuged again for 10 min The supernatant was discarded, and the sonication and centrifugation procedure was repeated 3 times, the last time without triton X-100. Pellets were dissolved 50 mM Tris buffer, pH 7.8, 6 M GuHCl, 10 mM β-mercaptoethanol at 4° C. overnight. The dissolved scFv was purified on a Ni-NTA column in denaturing conditions (6 M GuHCl), and was eluted using a pH gradient between pH 6.9 and pH 3.8. Refolding was performed as previously described [Kouhei, T. et. al. (1998) *J. Immunol. Methods* 219, 119-129].

Inhibitory Constant Determination

A Clarke-type oxygen electrode (Hansatech Instruments) was used to monitor changes in dissolved oxygen concentrations as a measure of HsQSOX1 activity. 25 nM HsQSOX1 and various concentrations (1-250 nM) of purified MAb492.1 were assayed in 50 mM potassium phosphate buffer, pH 7.5, 65 mM NaCl, 1 mM EDTA. Reactions were started by injection of dithiothreitol (DTT) to a concentration of 200 μM in the electrode reaction chamber. Measurements were conducted for different MAb492.1 concentrations, and initial slopes were calculated. The background decrease in oxygen concentration due to the presence of DTT and MAb492.1 was measured three times, averaged, and subtracted from the initial slopes to obtain the velocities of HsQSOX1 activity at various MAb492.1 concentrations. The ratios of the initial rates of HsQSOX1 in the presence and absence of inhibitor were plotted as a function of inhibitor concentration. The resulting curve was fitted to the following equation as previously described [Morrison J. F. (1969) *Biophys. Biochem. Acta* 185, 269-286; Bieth J. G. (1995) *Methods in Enzymology* 248, 59-84] for obtaining Ki for a tight binding inhibitor:

$$\frac{V_i}{V_0} = \frac{1}{2[E_0]}\left(([E_0] - [I_0] - Ki) + \sqrt{(I_0 + Ki - [E_0])^2 + 4Ki[E_0]}\right)$$

Where $v_0$ is the velocity of reaction in the absence of MAb492.1, $v_i$ is the velocity in the presence of different MAb492.1 concentrations, $[E_0]$ is the total enzyme concentration (25 nM), $[I_0]$ is the total MAb492.1 concentration, and Ki is the inhibitory constant to be determined.

The inhibitory constant of scFv492.1 was calculated from the $IC_{50}$ value obtained by the colorimetric assay based on rdRNase oxidation, using the equation for classical competitive inhibition: $Ki=IC_{50}/(1+[S]_0/Km)$.

Where $[S]_0$ is the initial substrate concentration and Km is the Michaelis constant of HsQSOX1 for rdRNase, which is 320±35 μM.

MAb492.1 Fab—HsQSOX1$T_{rx}$ Complex Purification and Crystallization

Purified MAb492.1 concentrated to 1.5 mg/ml in PBS was digested at 37° C. using activated papain in a 1:20 papain: MAb492.1 ratio. Papain (Sigma) was dissolved in PBS, 20 mM EDTA and activated with 20 mM cysteine. Digestion was stopped after four hr using leupeptin as an inhibitor, and the digested antibody was dialyzed against PBS, pH 8. The Fab fragment of MAb492.1 (Fab492.1) was purified by size exclusion chromatography followed by protein G purification. The purified Fab492.1 was incubated for 1 hr at 4° C. with a two-fold excess of HsQSOX1$_{Trx}$, and the complex was isolated using size exclusion chromatography at a concentration of 11 mg/ml. Crystals were grown by hanging-drop vapor diffusion at 293 K over a well solution containing 19% w/v polyethylene glycol (PEG) 4 kD, 0.4 M ammonium phosphate dibasic. Crystals were transferred to a solution containing 20% w/v PEG 4 kD, 25% glycerol, 0.35 M ammonium phosphate dibasic, and flash frozen.

Data Collection

Diffraction data were collected at 100 K, on a RU-H3R generator (Rigaku) equipped with a RaxisIV++ image plate system and Osmic mirrors. Data were collected 2.7 Å resolution from a crystal of space group P6$_1$ with unit cell dimensions a=b=209.311 Å, c=55.265 Å, α=μ=90°, γ=120°. Data were processed and scaled using DENZO and SCALEPACK.

Structure Solution

Structure was determined by molecular replacement (MR) using Phaser. First, the structure of HsQSOX$_{Trx}$ was used for the search and suitable rotation and translation solutions were found. Then the constant region of a Fab structure with 75% sequence identity (PDB code 3OKD), was used as a search model, and finally, the variable region without the CDR loops from the same Fab model were searched. Refinement was performed using CNS, and model rebuilding was done using Coot. Validation of the structures was performed using MOLPROBITY, according to which there were no Ramachandran outliers, and the structure model was rated in the top 95% in its resolution range.

Cell Invasion Assay

WI-38 fibroblasts (Coriell) were seeded in the upper chambers of 24-well BD BioCoat plates with 8.0 μm pore size membrane inserts and allowed to grow for 4 days to reach confluence in the presence of different MAb492.1 concentrations or anti β actin (control antibody). On the fourth day, $5\times10^4$ H460 human lung cancer epithelial cells, pre-labeled with the cell-tracker dye CSFE (Molecular Probes) according to the manufacturer's instructions, were layered onto the fibroblasts. The inner chamber was filled with serum-free minimal essential medium (MEM), and the outer chamber with MEM containing 10% fetal bovine serum. Labeled H460 cells were allowed to migrate across the membrane for 24 hr at 37° C. Non-invading cells were manually scraped off the upper face of the membrane and discarded, and invading cells on the lower face were fixed in 3.7% formaldehyde, imaged, and quantified.

HsQSOX1 Inhibition In Vivo in a Xenograft Experiment

MDA-MB-231-RFP breast cancer tumor cells were grown as previously described [Goldshaid, L. et. al. (2010) *Breast Cancer Research* 12:R29]. GFP-hTert-WI-38 lung fibroblasts were grown in MEM media supplemented with 15 FCS, L-glutamine, Na-pyruvate, and antibiotics.

Twenty-six female, CD-1 nude mice, six weeks old, were separated into six groups (see Table 6, hereinbelow), housed and handled according to the Institutional Animal Care and Use instructions. The experimental procedure was approved by the Institutional Animal Care and Use Committee at the Weizmann Institute of Science (Rehovot, Israel).

To initiate the experiment, three groups of mice were injected in the left bottom mammary fat pad with a mixture of 10⁷ harvested fibroblasts and 10⁶ harvested tumor cells suspended in 50 µL PBS. Two other groups were injected similarly with tumor cells only. Four days post injection, treatment with MAb492.1 was initiated. Various dosages of MAb492.1 (see Table 6, hereinbelow) were prepared in 200 µL PBS and administered twice a week intravenously (IV). One week after injection of cells the mice were imaged in the In Vivo Optical Imaging System (IVISR100/XFO-12, Xenogen Corp., Alameda, Calif., USA), to verify the formation of localized tumors, using luciferin bioluminescence. Before imaging, mice were given an intraperitoneal (IP) injection of 1.5 mg D-luciferin and anesthetized by injection of a 50 µL mixture of 85:15 ketamine:xylazine. Five weeks after injection of cells the mice were anesthetized as described, and imaged under a fluorescent microscope to identify metastasis in the popliteal and axillary lymph nodes. Animals were sacrificed with pentobarbital five weeks after the beginning of the experiment.

MAb492.1 Specificity Assay

The mammalian QSOX1 enzymes MmQSOX1 (wild-type and the three mutants), CpQSOX1, and RnQSOX1 were cloned, expressed, and purified as for HsQSOX1 (as described above). The activities of these enzymes at 50 nM were evaluated using an oxygen consumption assay (as described above) and 200 µM DTT as a substrate. The activity in the presence of 250 nM or 1 µM MAb492.1 was measured as well, and compared to the activity in the absence of MAb492.1.

MmQSOX1 $T_{Trx}$ Purification and Crystallization

MmQSOX1$_{Trx}$ was cloned and expressed as for HsQSOX1. The purification was done similarly to HsQSOX1 purification, except that the Ni-NTA chromatography was done in 20 mM Tris buffer, pH 8.5, 500 mM NaCl, 20 mM imidazole for binding, and 250 mM imidazole for elution. The eluted enzyme was loaded immediately onto a size exclusion chromatography column and purified in 10 mM Tris buffer, pH 8.5, 100 mM NaCl. Crystals were grown by hanging-drop vapor diffusion at 293 K over a well solution containing 7% w/v PEG monomethyl-ether 2 kD, 0.1 M sodium acetate pH 4.6, 5% DMSO. The protein concentration in the drop was 13 mg/ml, and it was supplemented with 1 unit of thrombin per 0.4 mg protein. Crystals were transferred to a solution containing 15% w/v PEG monomethyl-ether 2 kD, 25% glycerol, 0.1 M sodium acetate pH 4.6, and flash frozen.

MmQSOX1$_{Trx}$ Data Collection and Structure Solution

Diffraction data were collected at 100 K on a RU-H3R generator (Rigaku) equipped with a RaxisIV++ image plate system and Osmic mirrors. Data were collected to 2.05 Å resolution from a crystal of space group P2₁ with unit cell dimensions a=42.48 Å, b=116.38 Å, c=50.02 Å, α=γ=90°, β=103.1°. Data were processed and scaled using DENZO and SCALEPACK. The structure of MmQSOX1$_{Trx}$ was determined by MR using the structure of HsQSOX1$_{Trx}$ as a search model. Refinement was performed using CNS, and model rebuilding was done using Coot. Validation of the structures was performed using MOLPROBITY, according to which there were no Ramachandran outliers, and the structure model was rated in the top 70% in its resolution range.

Results

Selection of Antibody Clones that Bind and Inhibit HsQSOX1

Recombinant human QSOX1 (hereafter referred to as HsQSOX1) produced in bacteria [Akin et al., (2012) Nature 488, 414-418] was used to elicit antibody production in mice, and hybridomas were generated. Hybridoma supernatants were screened for binding of HsQSOX1 using a standard ELISA assay. Of approximately 500 clones that were screened, five top binders were chosen for sub-cloning. Each of the sub-clones was tested for binding by ELISA. Approximately 30 sub-clones were chosen for inhibition assays.

Inhibition was tested using an in vitro sulfhydryl oxidase activity assay. To avoid reduction of antibodies, a mild reducing substrate, reduced and denatured RNase A (rdRNase), was initially chosen. The rdRNase was subjected to oxidation by HsQSOX1 in the presence of high concentrations of various purified antibody sub-clones, and thiol groups remaining after a period of time were quantified by reaction with 5,5'-dithiobis-(2-nitrobenzoic acid) (DTNB). High DTNB reactivity signified the presence of a high concentration of thiol groups in solution at the end of the reaction, which was taken to indicate HsQSOX1 inhibition. Antibody sub-clones derived from one particular clone showed good HsQSOX1 inhibition in this assay. One sub-clone, MAb492.1, classified to be of the IgG1 isotype, was selected for further study.

Determination of Inhibitory Constant

HsQSOX1 inhibition was tested at various concentrations of MAb492.1. When the DTNB assay was first employed with 250 nM HsQSOX1, an IC$_{50}$ of 240±30 nM was observed. As this value corresponds closely to the enzyme concentration in the assay, it suggested near-stoichiometric binding of HsQSOX1 by MAb492.1 and effective inhibition under the conditions of the assay. When the HsQSOX1 concentration was lowered to 50 nM, an IC$_{50}$ of 60±10 nM was observed (FIG. 15A). Again, this value is approximately equal to the enzyme concentration, further supporting tight binding and effective inhibition. Lower enzyme and antibody concentrations were explored using an oxygen consumption assay, which monitors the rate of decrease of dissolved oxygen as it is reduced by HsQSOX1 to hydrogen peroxide. This assay allows direct determination of initial velocities and not just degree of activity. Although a strong reducing agent, dithiothreitol (DTT), was used as an electron donor in this experiment, a DTT concentration was chosen that preserved antibody integrity (FIG. 15C). Reaction rates were calculated from experiments using 25 nM HsQSOX1 and various concentrations of MAb492.1. Fitting the results to a model for a tight-binding inhibitor yielded an apparent inhibitory constant of 1.0±0.3 nM (FIG. 15B). MAb492.1 binds HsQSOX1 at the amino-terminal, Trx1 domain (FIG. 1A), and prevents substrate access to the active site of the redox-active di-cysteine motif, indicating that MAb492.1 is a competitive inhibitor. Reaction rates in the presence of competitive inhibitors typically vary with substrate concentration, and thus the apparent Ki does not necessarily represent the actual Ki. Nevertheless, the MAb492.1 inhibition was independent of the substrate concentration (FIG. 15D), implying that the dissociation of the MAb492.1-HsQSOX1 complex is slow relative to the time frame of the experiment and is not induced by substrate. Under these conditions, the apparent inhibitory constant becomes the actual inhibitory constant.

Determination of the Antibody Binding Site on HsQSOX1

It was previously observed that limited proteolysis of avian QSOX produces two stable fragments. Similar observations were made for mammalian QSOX1 enzymes, and the structures of the two fragments of human QSOX1, HsQSOX1$_{Trx}$ and HsQSOX1$_{Erv}$ (FIGS. 1A-B), have been previously determined using X-ray crystallography [Akin A. et al. (2010) FEBS Lett. 584, 1521-1525; Alon et al. (2012) Nature 488, 414-418]. To determine whether the binding site for MAb492.1 resides in HsQSOX1$T_{rx}$ or HsQSOX1$_{Erv}$, inventors produced each of the two fragments in bacteria and performed two complementary binding assays. In the first assay, binding of MAb492.1 to HsQSOX1$_T$ or HsQSOX1$_{Erv}$ was compared with binding to full-length HsQSOX1 by ELISA. HsQSOX1$_{Erv}$, containing the Trx1 and Trx2 domains, bound MAb492.1 to the same extent as did full-length HsQSOX1 (FIG. 16A). HsQSOX1$_{Erv}$, on the other hand, did not bind MAb492.1 at any concentration tested. The second binding assay used size exclusion chromatography. The migration profiles of HsQSOX1, HsQSOX1$_{Trx}$, and HsQSOX1$_{Erv}$ were measured in the presence and absence of MAb492.1. The migration profiles of both HsQSOX1 and HsQSOX1$_{Trx}$ were shifted following incubation with MAb492.1, but the migration of HsQSOX1$_{Erv}$ was unaffected (FIGS. 16B-D), confirming the conclusion that MAb492.1 binds to the amino-terminal portion of HsQSOX1.

Sequencing of the MAb492.1 Antibody Clone and Construction of a Single-Chain Variable Fragment The sequence of MAb492.1 was determined by reverse-transcription and PCR from the hybridoma clone. The variable region of the light chain was amplified with a relatively small set of degenerate primers. In contrast, the variable region of the heavy chain could not be amplified using a comparable primer mix, consistent with the relative difficulty of amplifying heavy chains observed previously. Therefore, the MAb492.1 heavy chain was amplified using optimized primers for mouse scFv repertoire cloning. Each amplified fragment was cloned into the pGEM-T Easy vector and sequenced. These sequences (see Table 3, below) were analyzed using tools associated with the ImMunoGeneTics (IMGT) database as previously described [Lefranc M. P. et al. (2004) Nuc. Acids Res. 33, 593-597] and were confirmed to be productively rearranged sequences. The variable regions showed over 94% identity to database entries for variable regions of antibodies produced in mice. The sequences were also confirmed by tandem mass spectrometry (LC-MS/MS) of purified MAb492.1 (see Table 3, below).

TABLE 3

MAb492.1 variable region amino acid sequences

| Sequence | Chain |
| --- | --- |
| DVVMTQTHKFMSTSVGDRVSITCKASQDVSTAVAWYQQKSGQSPKLLIHSAS YRYTGVPDRFTGSGSGTDFTFTISSVQAEDLAVYYCQQHYSIPLTFGAGTKL ELK (SEQ ID NO: 7) | Light |
| QVQLKQSGPGLVAPSQSLSITCTVSGFSLTGYGVNWVRQSPGKGLEWLGMI WGDGRTDYKSALKSRLSITKDNSKSQVFLKMNSLQTDDTARYFCASDYYGS GSFAYWGQGTLVTVSA (SEQ ID NO: 8) | Heavy |

| Mr(calc) | Mr(exp) | Peptide | Enzyme | Chain |
| --- | --- | --- | --- | --- |
| 2037.9612 | 2037.9634 | DVVMTQTHKFMSTSVGDR (SEQ ID NO: 9) | trypsin | Light |
| 2742.3140 | 2742.3148 | DVVMTQTHKFMSTSVGDRVST ICK (SEQ ID NO: 10) | | |
| 1686.8069 | 1686.8076 | FMSTSVGDRVSITCK (SEQ ID NO: 11) | | |
| 1680.8107 | 1680.8110 | ASQDVSTAVAWYQQK (SEQ ID NO: 12) | | |
| 1058.5873 | 1058.5880 | LLIHSASYR (SEQ ID NO: 13) | | |
| 1766.8332 | 1766.8344 | DVVMTQTHKFMSTSVG (SEQ ID NO: 14) | chymotrypsin/ Asp-N | |
| 1841.8612 | 1841.8642 | MSTSVGDRVSITCKASQ (SEQ ID NO: 15) | | |
| 1870.9901 | 1870.9938 | QQKSGQSPKLLIHSASY (SEQ ID NO: 16) | | |
| 1075.4459 | 1075.4468 | TGSGSGTDETF (SEQ ID NO: 17) | | |
| 1203.6863 | 1203.6886 | SIPLTFGAGTKL (SEQ ID NO: 18) | | |
| 995.4713 | 995.4732 | SLTGYGVNW (SEQ ID NO: 19) | chymotrypsin/ Asp-N | Heavy |
| 1711.8794 | 1711.8808 | GVNWVRQSPGKGLEW (SEQ ID NO: 20) | | |
| 1179.6611 | 1179.6637 | DYKSALKSRL (SEQ ID NO: 21) | | |
| 1837.0057 | 1837.0096 | KSRLSITKDNSKSQVF (SEQ ID NO: 22) | | |
| 1985.9782 | 1985.9824 | QSPGKGLEWLGMIWGDGR (SEQ ID NO: 23) | trypsin | |
| 1488.7184 | 1488.7206 | GLEWLGMIWGDGR (SEQ ID NO: 24) | | |
| 1995.9513 | 1995.9510 | GLEWLGMIWGDGRTDYK (SEQ ID NO: 25) | | |

TABLE 3-continued

MAb492.1 variable region amino acid sequences

| 1250.5561 | 1250.5576 | MNSLQTDDTAR (SEQ ID NO: 26) |
|---|---|---|

Light and heavy chain sequences of MAb492.1 were obtained as described in the 'Materials and Experimental Procedures' section above. MAb492.1 after treatment with DTT displayed two bands in SDS-PAGE, an upper band corresponding to the heavy chain, and a lower band corresponding to the light chain. Bands were digested in-gel with trypsin or chymotrypsin and AspN. The table displays representative peptides detected by LC-MS/MS at least once, after cleavage with trypsin or with chymotrypsin and AspN.

The variable regions that were identified from MAb492.1 were used to construct a single chain antibody fragment (scFv). The scFv was composed of the heavy chain variable domain at the amino terminus, the light chain variable domain at the carboxy terminus, and a linker of $[Gly_4Ser]_3$ connecting them. The sequence encoding the scFv was optimized for expression in *E. coli* and cloned into an expression vector with a thrombin-cleavable $His_6$-tag at the amino terminus. The purified scFv, designated scFv492.1, was obtained from inclusion bodies after production in bacteria and was refolded to obtain functional material. Refolded scFv492.1 was tested in the colorimetric assay based on rdRNase oxidation and shown to inhibit 50 nM HsQSOX1 with an $IC_{50}$ of 250±30 nM (FIG. 17). An inhibitory constant of 130+20 nM could be calculated directly from this $IC_{50}$ value, since scFv492.1 is a competitive inhibitor. scFv492.1 most likely binds HsQSOX1 at the same site as MAb492.1, preventing substrate oxidation, but cannot be considered as a tight binding inhibitor because a five-fold excess is needed to inhibit HsQSOX1 under the same experimental conditions.

Determination of the Antibody Binding Site on HsQSOX1

A Fab fragment derived from MAb492.1 was prepared for co-crystallization with $HsQSOX1_{Trx}$. The Fab was produced from purified MAb492.1 by papain digestion. The ability of the Fab to bind and inhibit HsQSOX1 was tested through a colorimetric assay based on rdRNase oxidation. Fab492.1 was found to inhibit 50 nM HsQSOX1 with an $IC_{50}$ of 100±20 nM (FIG. 18), twice the $IC_{50}$ value found for full-length MAb492.1. The avidity of MAb492.1 was twice the avidity of the Fab fragment, indicating that Fab492.1 maintains the tight binding behavior.

The structure of the $HsQSOX1_{Trx}$ Fab492.1 complex was determined to 2.7 Å resolution (Table 4, below). The crystal structure revealed that Fab492.1 recognizes the amino terminal domain, Trx1 (FIG. 19A). In particular, Fab492.1 binds the active site, burying the CXXC motif and a large surface area surrounding it. The interface area was calculated to be 948.7 $Å^2$. All six CDRs participate in binding (FIG. 19B). The heavy chain is responsible for most of the interactions (FIG. 20B and table 5, below), including burial of the CXXC motif using all three CDRs. The light chain, responsible for 40% of the $HsQSOX1_{Trx}$-Fab492.1 interface (407.6 $Å^2$), binds a large surface area away from the active site (FIG. 19C), at the loop that connects the beta sheet with the c-terminal helix of the Trx1 domain. This region creates a continuous surface with the surface bound by the heavy chain that contains the active site. The light chain binds Trx1 through hydrophobic interactions and a network of hydrogen bonds (FIG. 20A and table 5, below), presumably stabilizing the orientation of the heavy chain relative to the active site. The structure of $HsQSOX1_{Trx}$ in complex with Fab492.1 showed few deviations from the structure of uncomplexed $HsQSOX1_{Trx}$, indicating that MAb492.1 does not disrupt the $HsQSOX1_{Trx}$ structure, but simply blocks substrate access to the active site.

TABLE 4

Data collection and refinement statistics

Data Collection

| | |
|---|---|
| Space group | $P6_1$ |
| Cell dimensions | |
| a, b, c (Å) | 209.311, 209.311, 55.265 |
| α, β, γ (°) | 90, 90, 120 |
| Wavelength (Å) | 1.5418 |
| Resolution (Å) | 50-2.7 (2.75-2.70) |
| $R_{sym}{}^a$ | 9.2 (36.3) |
| I/σ | 14.35 (1.96) |
| Completeness | 97.3 (91.9) |
| Redundancy | 5.1 (3.8) |

Refinement

| | |
|---|---|
| Resolution (Å) | 50-2.70 |
| No. reflections/test | 34719/2622 |
| $R_{work}/R_{free}{}^b$ | 20.0/23.5 |

No. atoms

| | |
|---|---|
| Protein | 5155 |
| Phosphate | 10 |
| Water | 350 |

R.m.s deviations

| | |
|---|---|
| Bond lengths (Å) | 0.006 |
| Bond angles (°) | 1.4 |

Values in parentheses are for the highest-resolution shell $^a R_{sym} = \Sigma_{hkl}\Sigma_i |I_i(hkl) - <I(hkl)>|/\Sigma_{hkl}\Sigma_i I_i(hkl)$, where $I_i(hkl)$ is the observed intensity and $<I(hkl)>$ is the average intensity for i observations.

$^b R_{work}, R_{free} = \Sigma ||F_{obs}| - |F_{calc}||/\Sigma |F_{obs}|$, where $F_{obs}$ and $F_{calc}$ are the observed and calculated structure factors, respectively. A set of reflections (6.8%) were excluded from refinement and used to calculate $R_{free}$.

TABLE 5

Fab492.1 - $HsQSOX1_{Trx}$ interactions

| | Fab492.1 | $HsQSOX1_{Trx}$ | | |
|---|---|---|---|---|
| CDR | Residue | Residue | Type of interaction | Distance |
| L1 | Ser30 | Val135 | Hydrogen bond | 2.9 Å |
| L1 | Ala32 | Val135 | Hydrophobic | <5 Å |
| Framework 3 (light chain) | Tyr53 | Pro137 | Hydrophobic | <5 Å |
| Framework 3 (light chain) | Tyr53 | Arg149 | cation-π | 4.86 Å |
| L3 | Tyr92 | Arg122 | cation-π | 4 Å |
| L3 | Tyr92 | Arg122 | Hydrogen bond | 3.2 Å |
| L3 | Tyr92 | Ser132 | Hydrogen bond | 3.4 Å |
| L3 | Tyr92 | Gly133 | Hydrogen bond | 2.6 Å |
| L3 | Tyr92 | Val135 | Hydrophobic | <5 Å |
| L3 | Ile94 | Asn114 | Hydrogen bonds | 2.6 Å, 3.5 Å |
| L3 | Ile94 | Pro116 | Hydrophobic | <5 Å |
| L3 | Leu96 | Pro116 | Hydrophobic | <5 Å |
| H1 | Gly31 | Gly71 | Hydrogen bond | 2.9 Å |
| H2 | Trp52 | Trp69 | Hydrophobic | <5 Å |
| H2 | Trp52 | Trp69 | Aromatic-aromatic | 6.9 Å |
| H2 | Trp52 | Phe118 | Hydrophobic | <5 Å |
| H2 | Trp52 | Phe118 | Aromatic-aromatic | 5 Å |

TABLE 5-continued

Fab492.1 - HsQSOX1$_{Trx}$ interactions

| Fab492.1 | | HsQSOX1$_{Trx}$ | | |
|---|---|---|---|---|
| CDR | Residue | Residue | Type of interaction | Distance |
| Frame work 3 (heavy chain) | Asp58 | Arg111 | Salt bridge | 6.9 Å |
| H3 | Asp98 | His72 | Salt bridge | 6.9 Å |
| H3 | Tyr99 | Ala139 | Hydrophobic | <5 Å |
| H3 | Tyr100 | His72 | Hydrogen bond | 3.4 Å |
| H3 | Tyr100 | Phe76 | Hydrophobic | <5 Å |
| H3 | Tyr100 | Phe76 | Aromatic-aromatic | 6.1 Å |
| H3 | Tyr100 | Pro119 | Hydrophobic | <5 Å |
| H3 | Tyr100 | Val138 | Hydrophobic | <5 Å |
| H3 | Tyr100 | Ala139 | Hydrophobic | <5 Å |
| H3 | Gly101 | Thr120 | Hydrogen bond | 3.4 Å |

HsQSOX1 Inhibition in Co-Culture Assays for Tumor Cell Migration Through Stroma

MAb492.1 was tested for its ability to inhibit fibroblast production of an ECM layer that supports tumor cell invasion. An organotypic invasion assay was conducted by first allowing WI-38 fibroblasts to become confluent and accumulate ECM over four days in the presence of different MAb492.1 concentrations. For control, an antibody for β actin was added. Then, fluorescently labeled H460 lung tumor cells were placed onto the fibroblasts. After 24 hours, the cells that had penetrated the fibroblast layer and associated ECM in each sample were counted (FIGS. 21A-O and 22). Samples treated with 250 nM and 500 nM MAb492.1 showed less tumor cell invasion than the untreated sample, demonstrating that MAb492.1 can block tumor cell migration in cell culture. Samples treated with 50 nM MAb492.1 didn't show a difference in tumor cell invasion, indicating that the HsQSOX1 concentration in the assay was around 50 nM or lower, based on the inhibitory constant determined.

HsQSOX1 Inhibition In-Vivo in a Xenograft Experiment for Metastasis Prevention or Reduction To demonstrate that HsQSOX1 inhibition in vivo can modulate BM composition and can prevent, slow down, or eliminate tumor cell migration, an animal model that incorporates both tumor cells and tumor-associated fibroblasts was required.

MAb492.1 shows great specificity towards HsQSOX1 (data not shown), eliminating the option to study QSOX1 inhibition in vivo when QSOX1 is secreted from animal fibroblasts. To overcome this obstacle, a xenograft assay which involves transplantation of living cells from one species to another, was performed on nude mice (mice with an inhibited immune system due to an absent or flawed thymus). Different compositions of cell injections and different treatments (summarized in Table 6, hereinbelow) were given to six groups comprising 3-5 female nude mice each.

A mixture of human breast cancer cells together with human fibroblasts was injected to the mammary fat pad of three groups of mice. Two groups received only breast cancer cells, to confirm that the metastatic growth is supported by secreted HsQSOX1 and not by intracellular HsQSOX1 localized to the tumor itself. The last group was not transplanted with any human cells, to test the effect of MAb492.1 on healthy animals. The human immortalized fibroblasts used were GFP-hTERT-WI-38 fibroblasts. MDA-MB-231 breast cancer cells containing red fluorescent protein (RFP) and luciferase were used as the tumor cells. The expression of luciferase, acting on luciferin to generate light, permits monitoring tumor cell migration by bioluminescence imaging during the course of the experiment Importantly, bioluminescence imaging has large signal-to-noise ratios in tissues, and the emitted signal can be detected in living animals noninvasively. The formation of a tumor localized to the mammary fat pad after one week was verified using luciferin bioluminescence (FIG. 23). Four days following inoculation of cells, several groups of mice (see Table 6, hereinbelow) began receiving a treatment of MAb492.1 in different dosages. Five weeks post injection of cells, metastasis progression to the axillary and popliteal lymph nodes was evaluated by the fluorescence emitted from the cancerous cells (see Table 6, hereinbelow).

The remaining animals displayed two main trends. First, animals that received MDA-MB-231 cancer cells together with human fibroblasts developed larger tumors producing more metastases than did animals receiving only MDA-MB-231 cells. This observation strengthened the already established idea that stromal components secreted from tumor-associated fibroblasts are fundamental for cancer progression. The second effect observed was that among the animals that received both fibroblasts and MDA-MB-231 cells, the ones treated with the higher MAb492.1 dosage (i.e. 30 mg/kg) had fewer lymph node infiltrations by cancerous cells compared to animals that received no treatment or a lower dosage (see Table 7, hereinbelow). The dosages and dosing regimens of MAb492.1 may be further optimized.

Importantly, the three animals that received MAb492.1 injections but no cells showed no abnormal behavior during the experiment, and no indication of inflammation was seen in the autopsy. As expected, MAb492.1 had no observable side effects.

TABLE 6 xenograft experiment

| Type of cells injected | Treatment | Tumor size and properties (viewed externally) | Metastasis location (according to RFP imaging) |
|---|---|---|---|
| Human breast cancer cells and immortalized human fibroblasts | 5 mg/kg MAb492.1 twice a week IV | Huge, with a gangrene | Cells are spread all over, localized tumor not formed |
| | | Medium | In all four lymph nodes |
| | | Huge, with a gangrene | In the collateral popliteal lymph node |
| | | Not visible | None |
| | | Huge, with a gangrene | In the collateral popliteal lymph node and in the axillary lymph node, on the same side of the tumor |

TABLE 6-continued xenograft experiment

| Type of cells injected | Treatment | Tumor size and properties (viewed externally) | Metastasis location (according to RFP imaging) |
|---|---|---|---|
| Human breast cancer cells and immortalized human fibroblasts | 30 mg/kg MAb492.1 twice a week IV | Medium | In the popliteal lymph node close to the tumor |
| | | Big and red | In the popliteal lymph node close to the tumor |
| | | Big and red | Cells are spread all over, localized tumor not formed |
| | | Medium | In the popliteal lymph node close to the tumor |
| Human breast cancer cells and immortalized human fibroblasts | none | Huge, with a gangrene | In the collateral popliteal lymph node |
| | | Not visible | None |
| | | Medium, close to the tail | Cells are spread all over, localized tumor not formed |
| | | big | In the collateral popliteal lymph node |
| Human breast cancer cells | none | small | None |
| | | Huge + gangrene | In the popliteal lymph node close to the tumor |
| | | Small | None |
| | | big | Cells are spread all over, localized tumor not formed |
| | | Not visible | None |
| Human breast cancer cells | 30 mg/Kg MAb492.1 twice a week IV | Big | Cells are spread all over, localized tumor not formed |
| | | medium | Cells are spread all over, localized tumor not formed |
| | | Not visible | None |
| | | Big and red | In the popliteal and the axillary lymph nodes, on the same side of the tumor |
| | | Big + gangrene Tail with gangrene | Cells are spread all over, localized tumor not formed |
| No human cells | 30 mg/Kg MAb492.1 twice a week IV | None None None | None None None |

TABLE 7 xenograft experiment summary

| Type of cells injected | Treatment | Number of animals included | % of animals with metastases in distal lymph nodes |
|---|---|---|---|
| Human breast cancer cells and immortalized human fibroblasts | 5 mg/kg MAb492.1 twice a week IV | 3 | 100% |
| Human breast cancer cells and immortalized human fibroblasts | 30 mg/kg MAb492.1 twice a week IV | 3 | 0% |
| Human breast cancer cells and immortalized human fibroblasts | none | 3 | 66% |
| Human breast cancer cells | none | 3 | 0% |
| Human breast cancer cells | 30 mg/kg MAb492.1 twice a week IV | 1 | 0% |

MAb492.1 Specificity Towards HsQSOX1

The inhibitory activity of MAb492.1 was tested on other mammalian QSOX1 enzymes to examine its specificity. The recombinant *Mus musculus* QSOX1, MmQSOX1, has a sequence identity of 79% to the recombinant HsQSOX1. Oxygen consumption assays showed that MAb492.1 had no effect on MmQSOX1, even at micromolar concentrations (FIG. 24). QSOX1 from *Rattus norvegicus*, RnQSOX1, and from *Cavia porcellus*, CpQSOX1, both have sequence identities of 79% to HsQSOX1, and their activity was not influenced by MAb492.1 either (FIG. 24).

Alignment of the Trx1 domain sequence of HsQSOX1 with the corresponding region of other QSOX1 enzymes shows that the sequences in the vicinity of the CGHC redox-active motifs are identical (FIG. 25). However, the region of HsQSOX1 bound by the antibody light chain and CDR H3 sequence (HsQSOX1$_{106-152}$) reveals a few differences compared to other QSOX1 enzymes (FIG. 25). In particular, Pro 116, which fits well into a cleft between hydrophobic CDR L3 side chains of MAb492.1, is replaced with alanine in other mammalian QSOX1 enzymes. Another region showing sequence differences is $V_{135}$-$V_{138}$ from HsQSOX1, corresponding to $Thr_{138}$-$Gly_{141}$ in MmQSOX1.

To determine how these differences in amino acid sequence affect the structures of QSOX1 orthologs, MmQSOX1$_{Trx}$ was crystallized, and its structure was solved. Two MmQSOX1$_{Trx}$ molecules were present in the asymmetric unit. Comparison of the HsQSOX1$_{Trx}$-Fab492.1 complex structure to the structure of MmQSOX1$_{Trx}$ (FIG. 26) in the vicinity of Pro116 shows that the alanine residue that replaces Pro116 cannot fill the hydrophobic cleft in a hypothetical complex between MmQSOX1 and Fab492.1 as well as Pro116 does. In addition, the replacement of proline with alanine affects the position of the backbone nearby and the rotamer of Asn117 from MmQSOX1 (corresponding to Asn114 from HsQSOX1). Thus, a clash is expected between MmQSOX1 Asn117 and Tyr92 from CDR L3 (FIG. 26, right). In addition, the $Thr_{138}$-$Gly_{141}$ loop from one of the MmQSOX1 molecules is closer to Tyr100 from CDR H3, than is the corresponding $V_{135}$-$V_{138}$ loop from HsQSOX1 (FIG. 26, left).

Three MmQSOX1 mutants that mimic HsQSOX1 in distinct positions were constructed based on the above observations. MAb492.1 inhibition was tested on these mutants to identify the residues that interfere with MAb492.1-MmQSOX1 complex formation. The activity of the first mutant, MmQSOX1 A119P, showed about 40% activity in the presence of MAb492.1 (FIG. 27). The second mutant, MmQSOX1 TLPG(138-141)VFPV (hereafter named TLPG mutant) showed about 50% activity in the presence of MAb492.1, and the third mutant, which comprises both mutations mentioned, was inhibited by MAb492.1, to the same extent as HsQSOX1. These results confirm that only a few residues (up to four which were mutated) determine the specificity of MAb492.1 towards HsQSOX1 compared to MmQSOX1.

Based on these observations, generation of MAb492.1 variants that inhibits MmQSOX1 and potentially other mammalian QSOX1 orthologs is possible based on a few mutations of the antibody CDRs or surrounding regions. Suggestions for mutations in MAb492.1 that may produce an antibody that inhibits MmQSOX1 (are listed in Table 8, below). Combinations of these mutations might also be employed.

TABLE 8 possible mutations in MAb492.1 to generate an antibody that targets MmQSOX1

| CDR | Possible mutations |
|---|---|
| H3 | Tyr100Asn |
| H3 | Tyr100Asp |
| H3 | Tyr100Gly |
| H3 | Tyr100Ser |
| H3 | Ala101Gly |
| L3 | Tyr92Asn |
| L3 | Tyr92Asp |
| L3 | Ser93Gly |
| L3 | Ser93Ala |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated monoclonal antibody comprising an antigen recognition domain comprising complementary determining regions (CDRs) sequences of SEQ ID NOs: 29-34.

2. The isolated antibody of claim 1, wherein said antibody is a single chain antibody.

3. A pharmaceutical composition comprising as an active ingredient the isolated antibody of claim 1 and a pharmaceutically acceptable carrier.

* * * * *